(12) United States Patent
Field et al.

(10) Patent No.: US 10,837,012 B2
(45) Date of Patent: Nov. 17, 2020

(54) COMPOSITIONS AND METHODS FOR POLYNUCLEOTIDE ASSEMBLY

(71) Applicant: LABGENIUS LTD, London (GB)

(72) Inventors: James Edward John Field, London (GB); Harrison Frederick Rickerby, London (GB)

(73) Assignee: LABGENIUS LTD, London (GB)

( * ) Notice: Subject to any disclaimer, the term of this patent is extended or adjusted under 35 U.S.C. 154(b) by 202 days.

(21) Appl. No.: 15/754,466

(22) PCT Filed: Sep. 15, 2016

(86) PCT No.: PCT/GB2016/052886
§ 371 (c)(1),
(2) Date: Feb. 22, 2018

(87) PCT Pub. No.: WO2017/046594
PCT Pub. Date: Mar. 23, 2017

(65) Prior Publication Data
US 2018/0230455 A1    Aug. 16, 2018

(30) Foreign Application Priority Data

Sep. 15, 2015 (GB) .................. 1516348.8

(51) Int. Cl.
*C12N 15/10* (2006.01)
*C12N 15/66* (2006.01)
*C12N 15/64* (2006.01)

(52) U.S. Cl.
CPC ......... *C12N 15/1031* (2013.01); *C12N 15/10* (2013.01); *C12N 15/1027* (2013.01);
(Continued)

(58) Field of Classification Search
None
See application file for complete search history.

(56) References Cited

U.S. PATENT DOCUMENTS

2013/0130249 A1* 5/2013 Klinnasauskas et al. ...................
C12Q 1/6846
435/6.11
2014/0303036 A1  10/2014 Roubos et al.
(Continued)

FOREIGN PATENT DOCUMENTS

GB     2465986 A      6/2010
WO   1993/018175 A1   9/1993
(Continued)

OTHER PUBLICATIONS

Geu-Flores et al., "USER fusion: a rapid and efficient method for simultaneous fusion and cloning of multiple PCR products," Nucleic Acids Res. 2007, 35(7):e55. (Year: 2007).*
Oliner et al. "In vivo cloning of PCR products in *E. coli*." Nucleic Acids Research 21(22):5192-5197 (1993).
Bitinaite et al., "USER™ friendly DNA engineering and cloning method by uracil excision." Nucleic Acids Research 35(6):1992-2002 (2007).
(Continued)

*Primary Examiner* — Kaijiang Zhang
(74) *Attorney, Agent, or Firm* — Nixon Peabody LLP; David S. Resnick; Nicole D. Kling

(57) ABSTRACT

Methods are provided for assembly of a target polynucleotide sequence comprising at least a first double stranded polynucleotide (DSP) and at least second DSP, and optionally further DSPs. The method comprises an assembly reaction comprising steps including providing a first single stranded polynucleotide (SSP) comprising the polynucleotide sequence of one strand of the first DSP, and a second SSP comprising the polynucleotide sequence of one strand of the second DSP and converting the SSPs to double stranded form via a primer and polymerase-mediated extension reaction. The DSPs comprise polynucleotide sequences that are complementary to other polynucleotide sequences within the assembly reaction such that the ordering and directionality of each of the first and second, and further DSPs is determined by unique overhang pairing. Nucleic
(Continued)

acid libraries and methods of making such libraries are also provided.

20 Claims, 18 Drawing Sheets

Specification includes a Sequence Listing.

(52) U.S. Cl.
CPC .............. *C12N 15/64* (2013.01); *C12N 15/66* (2013.01); *G01N 2333/90206* (2013.01)

(56) References Cited

U.S. PATENT DOCUMENTS

| | | |
|---|---|---|
| 2014/0309119 A1 | 10/2014 | Jacobson et al. |
| 2015/0203839 A1 | 7/2015 | Jacobson et al. |

FOREIGN PATENT DOCUMENTS

| | | | |
|---|---|---|---|
| WO | WO-9318175 A1 * | 9/1993 | ........... C12N 15/102 |
| WO | 1997/020078 A1 | 6/1997 | |
| WO | 2000/040715 A2 | 7/2000 | |
| WO | 2002/008408 A2 | 1/2002 | |
| WO | 2003/087301 A2 | 10/2003 | |
| WO | 2007/135354 A1 | 11/2007 | |
| WO | 2008/024176 A2 | 2/2008 | |
| WO | 2009/103027 A2 | 8/2009 | |
| WO | 2011/056872 A2 | 5/2011 | |
| WO | 2014/088693 A1 | 6/2014 | |

OTHER PUBLICATIONS

Coljee et al., "Seamless gene engineering using RNA-and DNA-overhang cloning." Nature Biotechnology 18 (7):789-791 (2000).

Gal et al., "Directional cloning of native PCR products with preformed sticky ends (Autosticky PCR)." Molecular and General Genetics MGG 260(6):569-573 (1999).

Geu-Flores et al., "USER fusion: a rapid and efficient method for simultaneous fusion and cloning of multiple PCR products." Nucleic Acids Research 35(7):e55 (2007).

Kuijpers et al., "A versatile, efficient strategy for assembly of multi-fragment expression vectors in *Saccharomyces cerevisiae* using 60 bp synthetic recombination sequences." Microbial Cell Factories 12(1):47 (2013).

New England Biolabs Inc "User Friendly Cloning Kit" Retrieved from the Internet: URL: [http://www.neb.com/nebecomm/ManualFiles/manualE5500.pdf] Retrieved on Jul. 11, 2007.

Nour-Eldin et al., "Advancing uracil-excision based cloning towards an ideal technique for cloning PCR fragments." Nucleic Acids Research 34(18):E122-E129 (2006).

Nour-Eldin et al., "USER cloning and USER fusion: the ideal cloning techniques for small and big laboratories." Methods in Molecular Biology 643:185-200 (2010).

Olsen et al., "PHUSER (Primer Help for USER): a novel tool for USER fusion primer design." Nucleic Acids Research 39(2):W61-W67 (2011).

Rashtchian et al., "Uracil DNA glycosylase-mediated cloning of polymerasechain reaction-amplified DNA: Application to genomic and cDNA cloning." Analytical Biochemistry 206(1):91-97 (1992).

* cited by examiner

20

SEQUENCE LISTING

```
<160> NUMBER OF SEQ ID NOS: 40

<210> SEQ ID NO 1
<211> LENGTH: 38
<212> TYPE: DNA
<213> ORGANISM: Artificial Sequence
<220> FEATURE:
<223> OTHER INFORMATION: Description of Artificial Sequence: Synthetic
```

```
                                    oligonucleotide
<220> FEATURE:
<223> OTHER INFORMATION: Sequence of SSP in Figure 3

<400> SEQUENCE: 1
ccctgactga cgatgagata agggctatga ttagaaag                              38

<210> SEQ ID NO 2
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Insert Sequence A of Example 2

<400> SEQUENCE: 2
atgtctccta ttctgggata ttggaagatc aaaggccttg tgcagcccac ccgtcttctt       60
ctggagtatc tcgaagagaa atatgaggaa cacctatacg agcgcgatga aggtgataaa      120
tggcggaaca agaagtttga gctcgggcta                                       150

<210> SEQ ID NO 3
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Insert Sequence B of Example 2

<400> SEQUENCE: 3
atgtcgccaa ttctaggtta ttggaagatc aaaggtctgg tacaacctac tcgtctgctt       60
cttgaatacc tgtaagaaaa gtacgaggaa catctttatg aacgcgatga agggacaag       120 tggcgaaata agaagtttga actcggtctt                                       150

<210> SEQ ID NO 4
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Insert Sequence C of Example 2

<400> SEQUENCE: 4
atgtcgccaa tcctggggta ttggaagata aaaggccttg tccagcccac gcgactacta       60
ctcgaatacc tggaggagaa atatgaagaa caccttacg agcgtgatga aggtgacaag       120
tggcgtaaca agaaatttga gcttgggcta                                       150

<210> SEQ ID NO 5
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Insert Sequence D of Example 2

<400> SEQUENCE: 5
atgtctccaa tactgggata ttggaaaata aaagggcttg ttcaaccaac ccgcctactt       60
```
ctggaatatc tggaagagaa gtatgaagag catctttatg aacgggatga gggtgacaaa    120
tggcgtaata agaagtttga acttggtctt                                    150

<210> SEQ ID NO 6
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Insert Sequence E of Example 2

<400> SEQUENCE: 6
atgtcaccaa tactcgggta ctggaaaatt aaaggcctcg tacagcctac ccgactgctt    60
ctagagtacc ttgaagaaaa gtatgaagag catctttatg agcgtgatga ggggacaaa    120 tggcgaaata aaaagtttga gcttgggctg                                    150

<210> SEQ ID NO 7
<211> LENGTH: 149
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Insert Sequence F of Example 2

<400> SEQUENCE: 7
atgtctcctt acttggatac tggaagatta agggactcgt tcaacctacg cgtcttctgc    60
tcgagtatct cgaggagaaa tacgaagaac atctctatga acgggacgag ggcgataaat    120
ggcgcaacaa gaagtttgaa ctggggctg                                     149

<210> SEQ ID NO 8
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Insert Sequence G of Example 2

<400> SEQUENCE: 8
atgtccccga tcctcggcta ctggaaaatt aagggctcg ttcagcctac ccgtctgcta     60
ctcgaatacc tggaagaaaa atatgaggaa catctatatg aacgcgacga aggggacaag    120
tggcgaaata agaagttcga actagggctg                                    150

<210> SEQ ID NO 9
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Insert Sequence H of Example 2

<400> SEQUENCE: 9
atgtctccta ttctcgggta ttggaagatc aaagggctgg tccagcctac tcggctactt    60
ctggaatatc ttgaggaaaa atatgaggaa cacctgtatg aacgtgacga aggagataag    120
tggcgtaaca agaaattcga gctgggccta                                    150

```
<210> SEQ ID NO 10
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Target Protein Sequence of Example 2

<400> SEQUENCE: 10
```

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu
    50

```
<210> SEQ ID NO 11
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Protein expressed by colony G in Example 2

<400> SEQUENCE: 11
```

Met Ser Pro Ile Leu Gly Tyr Trp Lys Ile Lys Gly Leu Val Gln Pro
1               5                   10                  15

Thr Arg Leu Leu Leu Glu Tyr Leu
            20

```
<210> SEQ ID NO 12
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Proetin sequence expressed by colony F in
      Example 2

<400> SEQUENCE: 12
```

Met Ser Pro Tyr Leu Asp Thr Gly Arg Leu Arg Asp Ser Phe Asn Leu
1               5                   10                  15

Arg Val Phe Cys Ser Ser Ile Ser Arg Arg Asn Thr Lys Asn Ile Ser
            20                  25                  30

Met Asn Gly Thr Arg Ala Ile Asn Gly Ala Thr Arg Ser Leu Asn Trp
        35                  40                  45

Gly

```
<210> SEQ ID NO 13
<211> LENGTH: 2000
<212> TYPE: DNA
<213> ORGANISM: Mytilus californianus

<400> SEQUENCE: 13
```

```
atggagggaa tcaaattaaa tctgtgcctc ctgtgcatat tttcttgtga cgtctttgct      60
ctttcaaatg gtttcataca caacgcatat ggctcagctt atgcaggtgc aagcgctggg     120
gcttacaagc cattacccgg ttcatacgga tcaaagcatg taccagtata taaacctatg     180
aataagattc caacatcata tatatccaag aaaagttatc cggcacccta taaaccgaaa     240
ggctatcatc ctacgaatag ttatcagcca acatatggat caaagacaaa ctatccgcca     300
atatataagc cagttgcaaa gaagctatca tcatacaaag ctattaagac aacgtatctg     360
gtctataaag caaagacaag ttatccacca gtttataaac ataagataac taatcctcca     420
acatataaac ctaagattac ttatccccca acatataaac caaagccaag ttatcctcca     480
acatataaac caaagccaag ttatcctcca acatataaag caaagaaaac ttatccttca     540
acatataaac caaagccaag ttatcctcca acatataaac ctaagataac ttatcctcca     600
acatataaac caaagccaag ttatccgcct tcatataagg caaagaaatc atatccttca     660
acatataaac caaagccaag ttatcctcca acatataaag caaagaaaac ttatccttca     720
acatataaac caaagccaag ttatcctcca acatataaac ctaagataac ttatcctcca     780
acatataaac caaagccaag ttatccgcct tcatataagg caaagaaatc atatccttca     840
acatataaac caaagccaag ttatcctcct acatataaac ctaagataac ttatcctcca     900
acatataaac caaagccaag ttatcctcca acatataaag caaagaaaac ttatcctcca     960
acatataaac ctaagataac ttatcctcca acatataaac caaagccaag ttatcccact    1020
tcatataaat ctaagaaaac ttatcctcca acatataaac ctaaaataac ttatccacca    1080
acatataaac caaagccaag ttatccacca tcatataaac ctaagattac ttatcctcca    1140
acttataaac ctaagaaaag ttatcctcca gcatacaaat ctaaggcaag ttatccccct    1200
tcttatcaac ccaagaaaac ttatctgcca tcatataaac ctaagaaaac ttatcctcca    1260
acatataaac gtaagataag ttatccacca acgtataaaa caaagccaag ttatccatca    1320
tcttataaac gtaaaacaag ttatccatca acatataaac gtaagactag ttatcctcca    1380
acatataaac ctaagataag ttatccttca acttataaaa caaagccaag ttatccacca    1440
acgtataaag caaagaaaac ttatcctcca acatataaac ctaagataac ttatcctcca    1500
acatataaac caaagccaag ttatcccact tcatataaat ctaagaaaac ttatcctcca    1560
acatataaac ctaaaataac ttatccacca acatataaac caaagccaag ttatccacca    1620
tcatataaac ctaagattac ttatcctcca acttataaac ctaagaaaag ttatcctcca    1680
gcatacaaat ctaaggcaag ttatccccct tcttatcaac ccaagaaaac ttatctgcca    1740
tcatataaac ctaagaaaac ttatcctcca acatataaac gtaagataag ttatccacca    1800
acgtataaaa caaagccaag ttatccagca tcttataaac gtaaaacaag ttatccatca    1860
acatataaac gtaagacaag ttatcctcca acatataaac ctaagataag ttatccttca    1920
acttataaaa caaagccaag ttatccacca acgtataaac caaaaccaag ttatgcatca    1980
tcatataaac ctaagatacg                                                2000
```

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer

```
<220> FEATURE:
<223> OTHER INFORMATION: Primer for Fragment 1 in Example 3

<400> SEQUENCE: 14
atgaugttgg aatcttattc atagg                                          25

<210> SEQ ID NO 15
<211> LENGTH: 199
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Fragment 1 in Example 3

<400> SEQUENCE: 15
atggagggaa tcaaattaaa tctgtgcctc ctgtgcatat tttcttgtga cgtctttgct    60
ctttcaaatg gtttcataca caacgcatat ggctcagctt atgcaggtgc aagcgctggg   120
gcttacaagc cattacccgg ttcatacgga tcaaagcatg taccagtata taaacctatg   180
aataagattc caacatcat                                                199

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<223> OTHER INFORMATION: Primer for Fragment 2 in Example 3

<400> SEQUENCE: 16
aaacuggtgg ataacttgtc tttgc                                          25

<210> SEQ ID NO 17
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide
<220> FEATURE:
<223> OTHER INFORMATION: Fragment 2 in Example 3

<400> SEQUENCE: 17
atcauatata tccaagaaaa gttatccggc accctataaa ccgaaaggct atcatcctac    60
gaatagttat cagccaacat atggatcaaa gacaaactat ccgccaatat ataagccagt   120
tgcaaagaag ctatcatcat acaaagctat taagacaacg tatctggtct ataaagcaaa   180
gacaagttat ccaccagttt                                               200

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
```

```
<223> OTHER INFORMATION: Description of Combined DNA/RNA Molecule:
      Synthetic primer
<220> FEATURE:
<223> OTHER INFORMATION: Primer for Fragment 3 in Example 3

<400> SEQUENCE: 18
atctuaggtt tatatgttgg aggataac                                          28

<210> SEQ ID NO 19
<211> LENGTH: 198
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide
<220> FEATURE:
<223> OTHER INFORMATION: Fragment 3 in Example 3

<400> SEQUENCE: 19
agttuataaa cataagataa ctaatcctcc aacatataaa cctaagatta cttatccccc       60
aacatataaa ccaaagccaa gttatcctcc aacatataaa ccaaagccaa gttatcctcc      120
aacatataaa gcaaagaaaa cttatccttc aacatataaa ccaaagccaa gttatcctcc      180
aacatataaa cctaagat                                                    198

<210> SEQ ID NO 20
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<223> OTHER INFORMATION: Primer for Fragment 4 in Example 3

<400> SEQUENCE: 20
aggauaagtt atcttaggtt tatatgttg                                         29

<210> SEQ ID NO 21
<211> LENGTH: 195
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide
<220> FEATURE:
<223> OTHER INFORMATION: Fragment 4 in Example 3

<400> SEQUENCE: 21
aagauaactt atcctccaac atataaacca aagccaagtt atccgccttc atataaggca       60
aagaaatcat atccttcaac atataaacca aagccaagtt atcctccaac atataaagca      120
aagaaaactt atccttcaac atataaacca agccaagtt atcctccaac atataaacct       180
aagataactt atcct                                                       195

<210> SEQ ID NO 22
<211> LENGTH: 28
<212> TYPE: DNA
```

```
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<223> OTHER INFORMATION: Primer for Fragment 5 in Example 3

<400> SEQUENCE: 22
aggtutatat gttggaggat aagtttttc                                       28

<210> SEQ ID NO 23
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide
<220> FEATURE:
<223> OTHER INFORMATION: Fragment 5 in Example 3

<400> SEQUENCE: 23
atccuccaac atataaacca aagccaagtt atccgccttc atataaggca aagaaatcat       60
atccttcaac atataaacca aagccaagtt atcctcctac atataaacct aagataactt      120
atcctccaac atataaacca aagccaagtt atcctccaac atataaagca aagaaaactt      180
atcctccaac atataaacct                                                  200

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<223> OTHER INFORMATION: Primer for Fragment 6 in Example 3

<400> SEQUENCE: 24
aggataacut ttcttaggtt tataagttg                                        29

<210> SEQ ID NO 25
<211> LENGTH: 200
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide
<220> FEATURE:
<223> OTHER INFORMATION: Fragment 6 in Example 3

<400> SEQUENCE: 25
aaccuaagat aacttatcct ccaacatata aaccaaagcc aagttatccc acttcatata       60
aatctaagaa aacttatcct ccaacatata aacctaaaat aacttatcca ccaacatata      120
aaccaaagcc aagttatcca ccatcatata aacctaagat tacttatcct ccaacttata      180
aacctaagaa aagttatcct                                                  200
```

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: Primer for Fragment 7 in Example 3

<400> SEQUENCE: 26
atatgutgat ggataacttg ttttacg                                27

<210> SEQ ID NO 27
<211> LENGTH: 198
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Description of Combined DNA/RNA Molecule: Synthetic polynucleotide
<220> FEATURE:
<223> OTHER INFORMATION: Fragment 7 in Example 3

<400> SEQUENCE: 27
agttatccuc cagcatacaa atctaaggca agttatcccc cttcttatca acccaagaaa    60
acttatctgc catcatataa acctaagaaa acttatcctc caacatataa acgtaagata   120
agttatccac caacgtataa aacaaagcca agttatccat catcttataa acgtaaaaca   180
agttatccat caacatat                                                 198

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence: Synthetic primer
<220> FEATURE:
<223> OTHER INFORMATION: Description of Combined DNA/RNA Molecule: Synthetic primer
<220> FEATURE:
<223> OTHER INFORMATION: Primer for Fragment 8 in Example 3

<400> SEQUENCE: 28
agatutatat gaagtgggat aacttgg                                27

<210> SEQ ID NO 29
<211> LENGTH: 192
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: Description of Combined DNA/RNA Molecule: Synthetic polynucleotide
<220> FEATURE:
<223> OTHER INFORMATION: Fragment 8 in Example 3

<400> SEQUENCE: 29
acatauaaac gtaagactag ttatcctcca acatataaac ctaagataag ttatccttca    60

```
acttataaaa caaagccaag ttatccacca acgtataaag caaagaaaac ttatcctcca    120
acatataaac ctaagataac ttatcctcca acatataaac caaagccaag ttatcccact    180
tcatataaat ct                                                        192

<210> SEQ ID NO 30
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<223> OTHER INFORMATION: Primer for Fragment 9 in Example 3

<400> SEQUENCE: 30
agataagutt tcttgggttg ataagaag                                       28

<210> SEQ ID NO 31
<211> LENGTH: 199
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide
<220> FEATURE:
<223> OTHER INFORMATION: Fragment 9 in Example 3

<400> SEQUENCE: 31
aatcuaagaa aacttatcct ccaacatata aacctaaaat aacttatcca ccaacatata     60
aaccaaagcc aagttatcca ccatcatata aacctaagat tacttatcct ccaacttata    120
aacctaagaa aagttatcct ccagcataca aatctaaggc aagttatccc ccttcttatc    180
aacccaagaa aacttatct                                                 199

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<223> OTHER INFORMATION: Primer for Fragment 10 in Example 3

<400> SEQUENCE: 32
ataagtugaa ggataactta tcttagg                                        27

<210> SEQ ID NO 33
<211> LENGTH: 198
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide
<220> FEATURE:
<223> OTHER INFORMATION: Fragment 10 in Example 3
```

<400> SEQUENCE: 33
acttatcugc catcatataa acctaagaaa acttatcctc caacatataa acgtaagata        60
agttatccac caacgtataa aacaaagcca agttatccag catcttataa acgtaaaaca       120
agttatccat caacatataa acgtaagaca agttatcctc caacatataa acctaagata       180
agttatcctt caacttat                                                     198

<210> SEQ ID NO 34
<211> LENGTH: 28
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<223> OTHER INFORMATION: Primer for Fragment 11 in Example 3

<400> SEQUENCE: 34
atcttaggut tatatgatga tgcataac                                           28

<210> SEQ ID NO 35
<211> LENGTH: 78
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: Fragment 11 in Example 3

<400> SEQUENCE: 35
aacttauaaa acaaagccaa gttatccacc aacgtataaa ccaaaaccaa gttatgcatc        60
atcatataaa cctaagat                                                     78

<210> SEQ ID NO 36
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Degenerate Sequence 1 Example 4
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (4)..(5)
<223> OTHER INFORMATION: a, c, t, g, unknown or other
<220> FEATURE:
<221> NAME/KEY: modified_base
<222> LOCATION: (7)..(8)
<223> OTHER INFORMATION: a, c, t, g, unknown or other
<220> FEATURE:
<221> NAME/KEY: modified_base
<222> LOCATION: (10)..(11)
<223> OTHER INFORMATION: a, c, t, g, unknown or other

<400> SEQUENCE: 36
nnbnnbnnbn nb                                                            12

```
<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Degenerate Sequence 2 Example 4
<220> FEATURE:
<221> NAME/KEY: modified_base
<222> LOCATION: (1)..(2)
<223> OTHER INFORMATION: a, c, t, g, unknown or other
<220> FEATURE:
<221> NAME/KEY: modified_base
<222> LOCATION: (4)..(5)
<223> OTHER INFORMATION: a, c, t, g, unknown or other
<220> FEATURE:
<221> NAME/KEY: modified_base
<222> LOCATION: (7)..(8)
<223> OTHER INFORMATION: a, c, t, g, unknown or other
<220> FEATURE:
<221> NAME/KEY: modified_base
<222> LOCATION: (10)..(11)
<223> OTHER INFORMATION: a, c, t, g, unknown or other
<220> FEATURE:
<221> NAME/KEY: modified_base
<222> LOCATION: (13)..(14)
<223> OTHER INFORMATION: a, c, t, g, unknown or other
<220> FEATURE:
<221> NAME/KEY: modified_base
<222> LOCATION: (16)..(17)
<223> OTHER INFORMATION: a, c, t, g, unknown or other
<220> FEATURE:
<221> NAME/KEY: modified_base
<222> LOCATION: (19)..(20)
<223> OTHER INFORMATION: a, c, t, g, unknown or other
<220> FEATURE:
<221> NAME/KEY: modified_base
<222> LOCATION: (22)..(23)
<223> OTHER INFORMATION: a, c, t, g, unknown or other
<220> FEATURE:
<221> NAME/KEY: modified_base
<222> LOCATION: (25)..(26)
<223> OTHER INFORMATION: a, c, t, g, unknown or other
<220> FEATURE:
<221> NAME/KEY: modified_base
<222> LOCATION: (28)..(29)
<223> OTHER INFORMATION: a, c, t, g, unknown or other

<400> SEQUENCE: 37
nnbnnbnnbn nbnnbnnbnn bnnbnnbnnb                                          30

<210> SEQ ID NO 38
<211> LENGTH: 152
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: Description of Combined DNA/RNA Molecule:
      Synthetic polynucleotide
<220> FEATURE:
<223> OTHER INFORMATION: SSP design Example 5

<400> SEQUENCE: 38
cagcauttga cggctagctc agtcctaggt acagtgctag ctaatacgac tcactatagg         60
gagatactag agaccgtcga gtacctttac agctagctca gtcctaggta ttatgctagc        120
uactcacgtt agtgagtagc tagcauaata cc                                      152
```

```
<210> SEQ ID NO 39
<211> LENGTH: 33
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<223> OTHER INFORMATION: Forward vector linearisation primer Example 5

<400> SEQUENCE: 39
atgctagcug agaaatcaaa ttaaggaggt aag                              33

<210> SEQ ID NO 40
<211> LENGTH: 26
<212> TYPE: DNA
<213> ORGANISM: Artificial Sequence
<220> FEATURE:
<223> OTHER INFORMATION: Description of Artificial Sequence: Synthetic
      primer
<220> FEATURE:
<223> OTHER INFORMATION: Description of Combined DNA/RNA Molecule:
      Synthetic primer
<220> FEATURE:
<223> OTHER INFORMATION: Reverse vector linearisation primer Example 5

<400> SEQUENCE: 40
atgctgucca gaaatcatcc ttagcg                                     26
```

COMPOSITIONS AND METHODS FOR POLYNUCLEOTIDE ASSEMBLY

CROSS-REFERENCE TO RELATED APPLICATIONS

This application is a 35 U.S.C. § 371 National Phase Entry Application of International Application No. PCT/GB2016/052886 filed Sep. 15, 2016, which designates the U.S. and claims benefit under 35 U.S.C. § 119(a) of Provisional Application No. 1516348.8 filed Sep. 15, 2015, the contents of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on May 7, 2018, is named 051039-090830-US_SL and is 21,807 bytes in size.

FIELD OF THE INVENTION

The invention relates to the field of polynucleotide assembly and nucleic acid library generation.

BACKGROUND

Synthesis of long double stranded polynucleotides (e.g. gene sequences) is currently conducted by a method that involves providing a plurality of relatively short single stranded oligonucleotides corresponding to fragments of each strand of the target double stranded polynucleotide sequence and annealing a portion of each fragment of the first strand, to a portion of a fragment of the second strand.

This results in a partially double stranded sequence comprising fragmented first and second strands. The resulting gaps between the fragments of each strand are then filled in using a polymerase enzyme (as shown in FIG. 1). This method relies on the efficient and specific annealing of single stranded oligonucleotides. Using this approach, it is difficult to accurately assemble certain polynucleotide designs, especially those that contain:

Repetitive motifs
High or low GC contents
Secondary structures (caused by motifs such as inverted motifs)
Degeneracy (e.g. libraries).

For sequences that contain one or more of the above features, the efficient and specific annealing of single stranded oligonucleotides (which is required for traditional polynucleotide assembly methods) is inhibited by off-target annealing and secondary structure formation. The present invention provides a new approach that is less susceptible to the problems caused by off-target annealing and secondary structure formation. As a result, this novel methodology can be used to produce certain polynucleotide sequences or libraries of polynucleotide sequences either more easily or with a greater fidelity than current approaches.

SUMMARY OF THE INVENTION

In accordance with the present invention, a first aspect provides an in vitro method of assembling a target polynucleotide sequence comprising at least a first double stranded polynucleotide (DSP) and a second DSP, the method comprising an assembly reaction comprising the steps of:

(i) providing a first single stranded polynucleotide (SSP) comprising the polynucleotide sequence of one strand of the first DSP, and a second SSP comprising the polynucleotide sequence of one strand of the second DSP, (ii) providing a first primer that binds at a terminus of the first SSP and a second primer that binds at a terminus of the second SSP and converting the first SSP to the first DSP and the second SSP to the second DSP through a polymerase-mediated extension of the first and second primers, wherein the first DSP comprises a polynucleotide sequence that is complementary to a polynucleotide sequence of the second DSP, (iii) generating a region of single stranded polynucleotide on each of the first and second DSP by forming a 3' or 5' overhang which comprises at least a portion of the complementary polynucleotide sequence; and (iv) assembling the target polynucleotide sequence by joining the first DSP to the second DSP via annealing of the complementary overhangs, wherein the ordering and directionality of each of the first and second DSP is determined by unique overhang pairing.

In embodiments, the method comprises at least a third DSP. In such embodiments, the method comprises:

(i) providing a first single stranded polynucleotide (SSP) comprising the polynucleotide sequence of one strand of the first DSP, a second SSP comprising the polynucleotide sequence of one strand of the second DSP, and at least a third SSP comprising the polynucleotide sequence of one strand of the third DSP;

(ii) providing a first primer that binds at a terminus of the first SSP, a second primer that binds at a terminus of the second SSP and a third primer that binds at a terminus of the third DSP, and converting the first SSP to the first DSP, the second SSP to the second DSP and the third SSP to the third DSP through a polymerase-mediated extension of the first, second, and third primers,
wherein the first DSP comprises a first complementary polynucleotide sequence (CPS1) that is complementary to a polynucleotide sequence of the second DSP, the second DSP comprises a second complementary polynucleotide sequence (CPS2) that is complementary to CPS1 of the first DSP as well as a third complementary polynucleotide sequence (CPS3) that is complementary to a polynucleotide sequence of the third DSP, and the third DSP comprises a fourth complementary polynucleotide sequence (CPS4) that is complementary to CPS3 of the second DSP;

(iii) generating a region of single stranded polynucleotide on each of the first, second and third DSPs by forming a 3' or 5' overhang which comprises at least a portion of the first to fourth complementary polynucleotide sequences (CPS1-4); and (iv) assembling the target polynucleotide sequence by joining the first DSP to the second DSP, and the second DSP to the third DSP via annealing of the complementary overhangs, wherein the ordering and directionality of each of the first, second and third DSPs is determined by unique overhang pairing within the first to fourth complementary polynucleotide sequences (CPS1-4).

In embodiments, the method may comprise no fewer than four DSPs, wherein the ordering and directionality of each of the no fewer than four DSPs is determined by unique overhang pairing within the respective complementary polynucleotide sequences. Alternatively, the method may comprise a plurality of DSPs, wherein the ordering and directionality of each of the plurality of DSPs is determined by unique overhang pairing within the respective complementary polynucleotide sequences. The method may in embodiments comprise no fewer than 8 DSPs, wherein the ordering and directionality of each of the no fewer than 8 DSPs is determined by unique overhang pairing within the respective complementary polynucleotide sequences.

In any of the embodiments of the methods of the invention, steps (i) to (iii) may occur in separate reaction vessels. In some embodiments, step (iv) occurs in a single reaction vessel.

Advantageously, each complementary polynucleotide sequence may be different and only permit annealing to one other complementary sequence within the assembly reaction. In particular, each complementary polynucleotide sequence may form a unique binding pair with one other complementary polynucleotide sequence within the assembly reaction, and the total number of unique binding pairs within the assembly reaction may be one less than the total number of DSPs in the assembly reaction.

In some embodiments, the primer comprises at least one uridine nucleotide. In embodiments, the SSP comprises at least one uridine nucleotide, and the uridine nucleotide is comprised within the complementary polynucleotide sequence. In some embodiments, at least one primer comprises at least one uridine nucleotide and at least one SSP comprises at least one uridine nucleotide within the complementary polynucleotide sequence.

In any embodiments in which a primer and/or SSP comprises at least one uridine nucleotide, the step (iii) of generating a region of single stranded polynucleotide may occur by exposing the DSPs to a mixture of Uracil DNA glycosylase (UDG) and a DNA glycosylase-lyase Endonuclease VIII, with these enzymes mediating deoxyuridine excision and backbone cleavage reaction.

Optionally, the step (iv) joining of the DSPs by via annealing of the complementary overhangs may comprise a ligation reaction. In embodiments, the ligation reaction is catalysed by a DNA ligase.

In some embodiments, the complementary polynucleotide sequence is not more than 15 bases in length, optionally not more than 12 bases in length, suitably not more than 8 bases in length. In embodiments, the complementary polynucleotide sequence may be not less than 4 bases in length, optionally not less than 6 bases in length, suitably not less than 8 bases in length.

In a specific embodiment, generating overhangs further comprises generating overhangs at the terminus of the first and last DSP that do not anneal to another DSP, such that the assembled target polynucleotide sequence comprises overhangs at both termini. In such embodiments, the assembled target polynucleotide sequence may have overhangs comprising sequences that are complementary to sequences in overhangs of a linearised vector. Advantageously, the linearised vector may be created by polymerase-mediated extension of the circular vector using primers containing at least one uridine nucleotide, followed by digestion into a linear vector and Uracil-Specific Excision Reagent (USER) mediated uridine excision and backbone cleavage reaction to generate the overhangs.

A second aspect of the invention provides an in vitro method of assembling a target polynucleotide sequence wherein the method comprises a first flanking double stranded polynucleotide (DSP), a second flanking DSP and at least one intervening DSP, the method comprising an assembly reaction comprising the steps of:

(i) providing a first flanking single stranded polynucleotide (SSP) comprising the polynucleotide sequence of one strand of the first flanking DSP, a second flanking SSP comprising the polynucleotide sequence of one strand of the second flanking DSP, and at least a further SSP comprising the polynucleotide sequence of one strand of the at least one intervening DSP;

(ii) providing a first primer that binds at a terminus of the first flanking SSP, a second primer that binds at a terminus of the second flanking SSP and a third primer that binds at a terminus of the intervening DSP, and converting the first flanking SSP to the first flanking DSP, the second flanking SSP to the second flanking DSP and the intervening SSP to the intervening DSP through a polymerase-mediated extension of the first, second, and third primers,
wherein the first flanking DSP comprises a first complementary polynucleotide sequence (CPS1) that is complementary to a polynucleotide sequence of the intervening DSP, the intervening DSP comprises a second complementary polynucleotide sequence (CPS2) that is complementary to CPS1 of the first flanking DSP as well as a third complementary polynucleotide sequence (CPS3) that is complementary to a polynucleotide sequence of the second flanking DSP, and the second flanking DSP comprises a fourth complementary polynucleotide sequence (CPS4) that is complementary to CPS3 of the intervening DSP;

(iii) generating a region of single stranded polynucleotide on each of the DSPs by forming a 3' or 5' overhang which comprises at least a portion of the first to fourth complementary polynucleotide sequences (CPS1-4); and (iv) assembling the target polynucleotide sequence by joining the first flanking DSP to the intervening DSP, and the intervening to the second flanking DSP via annealing of the complementary overhangs, wherein the ordering and directionality of each of the first flanking, intervening and second flanking DSPs is determined by unique overhang pairing within the first to fourth complementary polynucleotide sequences (CPS1-4).

In embodiments, the method comprises a plurality of intervening DSPs, wherein the ordering and directionality of each of the plurality of intervening DSPs both relative to each other and relative to the first flanking and second flanking DSPs is determined by unique overhang pairing within the respective complementary polynucleotide sequences.

In advantageous embodiments, each complementary polynucleotide sequence is different and only permits annealing to one other complementary sequence within the assembly reaction. In such embodiments, each complementary polynucleotide sequence may form a unique binding pair with one other complementary polynucleotide sequence within the assembly reaction, and the total number of unique binding pairs within the assembly reaction may be one less than the total number of DSPs in the assembly reaction.

In some embodiments, the first primer that binds at a terminus of the first flanking SSP comprises at least one deoxyuridine nucleotide. In such and other embodiments of the method according to the second aspect, the primer(s) that binds at a terminus of the at least one intervening SSP may comprise at least one deoxyuridine nucleotide. In embodiments, the at least one intervening SSP comprises at least one deoxyuridine nucleotide, and the deoxyuridine nucleotide is comprised within the complementary polynucleotide sequence. In yet another embodiment, the second flanking SSP comprises at least one deoxyuridine nucleotide, and the deoxyuridine nucleotide is comprised within the complementary polynucleotide sequence. In some embodiments where an intervening SSP and/or the second flanking SSP comprise a deoxyuridine nucleotide, the at least one deoxyuridine nucleotide is located no more than fifteen bases from the 5' terminus of the SSP.

In any embodiments wherein a primer and/or an SSP comprises a deoxyuridine nucleotide, the step (iii) of generating a region of single stranded polynucleotide may occur by exposing the DSPs to a Uracil-Specific Excision Reagent (USER) mediated deoxyuridine excision and backbone cleavage reaction. In such embodiments, exposing the DSPs to a USER mediated deoxyuridine excision may comprise exposing the DSPs to a mixture of Uracil DNA glycosylase (UDG) and a DNA glycosylase-lyase Endonuclease VIII.

In any embodiments of the method according to the second aspect of the invention, the first and/or second flanking DSP may comprise a vector sequence.

In some embodiments, the first and/or second flanking DSP comprises one or more of a DNA sequence encoding any one or more of antibiotic resistance markers, fluorescent proteins, regulatory proteins, antibody frameworks or proteins used for the display of binding proteins or peptides. Regulatory proteins may comprise transcription factors. In embodiments, the first and/or second flanking DSP comprises a DNA sequence encoding for a surface protein of a phage, yeast or bacteria. Such embodiments are advantageously suited for use as part of a phage display, yeast display or *E. coli* display protocol.

In embodiments of any of the methods of the invention, at least one of the DSPs comprised within the assembly reaction comprises a degenerate polynucleotide sequence.

In particular embodiments of the methods according to the first or second aspect above, one or more SSPs is/are covalently linked to a polynucleotide sequence comprising the primer binding at a terminus of the SSP.

In a third aspect, the disclosure provides a method of creating a library comprising a plurality of DNA fragments wherein each DNA fragment comprises a target polynucleotide sequence assembled according to the method of any embodiment of the first and second aspect above.

A fourth aspect of the invention provides a library comprising a plurality of DNA fragments, wherein the library has been created using the method of the third aspect above.

The methods of the invention are particularly useful for the construction of polynucleotide sequences that are difficult to produce using existing methods. Two problems encountered with existing polynucleotide construction methods include low yields of the target polynucleotide sequence and the accumulation of side reaction products (e.g. non-target polynucleotide sequences). Both of these problems are either caused or exacerbated by single stranded polynucleotide sequences participating in disadvantageous intra and inter-molecular interactions. Here we term disadvantageous intra and inter-molecular interactions, in the context of single stranded polynucleotide sequences, as "off-target annealing". The methods of the invention overcome the problem of off-target annealing associated with current assembly methods. This is in-part achieved by converting the single stranded polynucleotide sequences to a double stranded state prior to assembly. Locking the parts of a polynucleotide sequence that are not required for DSP joining in the double stranded state reduces the likelihood with which off-target interactions can occur when attempting to anneal portions of single stranded oligonucleotides. The invention therefore enables the production of synthetic polynucleotide sequences that cannot currently be made using existing gene synthesis techniques, such as for example highly repetitive sequences and large libraries (particularly library designs that contain degeneracy at a large number of nucleotide positions. The invention additionally enables target polynucleotide sequences to be assembled more efficiently (e.g. greater yields, lower levels of side reaction products, greater fidelity etc.) than existing methods allow.

DRAWINGS

DETAILED DESCRIPTION

Figure 1:
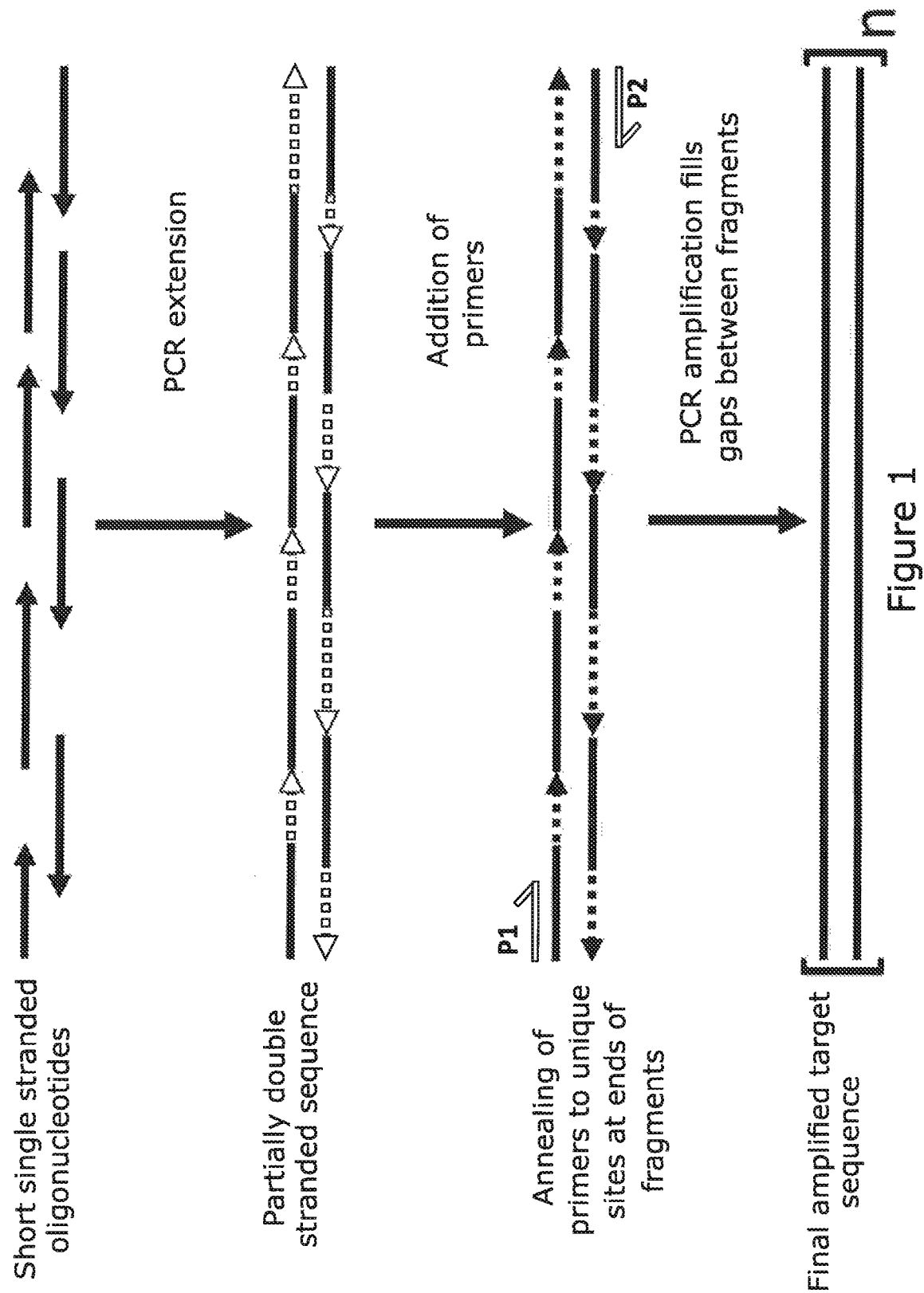
FIG. 1 shows an existing method of producing a double stranded polynucleotide.

Prior to setting forth the invention, a number of definitions are provided that will assist in the understanding of the invention. All references cited herein are incorporated by reference in their entirety. Unless otherwise defined, all technical and scientific terms used herein have the same meaning as commonly understood by one of ordinary skill in the art to which this invention belongs.

As used herein, the term "comprising" means any of the recited elements are necessarily included and other elements may optionally be included as well. "Consisting essentially of" means any recited elements are necessarily included, elements that would materially affect the basic and novel characteristics of the listed elements are excluded, and other elements may optionally be included. "Consisting of" means that all elements other than those listed are excluded. Embodiments defined by each of these terms are within the scope of this invention.

A 'polynucleotide' is a single or double stranded covalently-linked sequence of nucleotides in which the 3' and 5' ends on each nucleotide are joined by phosphodiester bonds. The polynucleotide may be made up of deoxyribonucleotide bases or ribonucleotide bases. Polynucleotides include DNA and RNA, and may be manufactured synthetically in vitro or isolated from natural sources. Sizes of polynucleotides are typically expressed as the number of base pairs (bp) for double stranded polynucleotides, or in the case of single stranded polynucleotides as the number of nucleotides (nt). One thousand bp or nt equal a kilobase (kb). Polynucleotides of less than around 40 nucleotides in length are typically called 'oligonucleotides'. The polynucleotide may be made up of deoxyribonucleotide bases or ribonucleotide base and may be manufactured synthetically in vitro or isolated from natural sources. Polynucleotides may further include modified DNA or RNA, for example DNA or RNA that has been methylated, or RNA that has been subject to post-translational modification, for example 5'-capping with 7-methylguanosine, 3'-processing such as cleavage and polyadenylation, and splicing. Polynucleotides of the invention may also include synthetic nucleic acids (XNA), such as hexitol nucleic acid (HNA), cyclohexene nucleic acid (CeNA), threose nucleic acid (TNA), glycerol nucleic acid (GNA), locked nucleic acid (LNA) and peptide nucleic acid (PNA).

Sizes of nucleic acids, also referred to herein as "polynucleotides" are typically expressed as the number of base pairs (bp) for double stranded polynucleotides, or in the case of single stranded polynucleotides as the number of nucleotides (nt). One thousand bp or nt equal a kilobase (kb). Polynucleotides of less than around 100 nucleotides in length are typically called "oligonucleotides" and may comprise primers for use in manipulation of DNA such as via polymerase chain reaction (PCR).

The term "target polynucleotide sequence" includes double stranded polynucleotide sequences that are constructed using the methods of the invention.

As used herein, the terms "3'" ("3 prime") and "5'" ("5 prime") take their usual meanings in the art, i.e. to distinguish the ends of polynucleotides. A polynucleotide has a 5' and a 3' end and polynucleotide sequences are conventionally written in a 5' to 3' direction.

The term "double stranded polynucleotide" includes both (i) fully double stranded polynucleotides having blunt ends and no regions of single stranded polynucleotide, and (ii) double stranded polynucleotides having a 5' and/or 3' overhang. The overhang or overhangs may be on either strand or both strands of the double stranded polynucleotide sequence.

As used herein, the term "overhang" means a stretch of unpaired nucleotides at the end of a double stranded (or partially double stranded) polynucleotide sequence.

When a feature of a polynucleotide sequence (such as a primer annealing site or a complementary sequence) is described as being "at the terminus" or "at one or both termini" of a polynucleotide sequence, this means either (i) that the feature is at the very terminus of the sequence i.e. it includes the final nucleotide in the sequence, or (ii) that the feature is in the region of the terminus i.e. towards the 5' or 3' end of a polynucleotide sequence, but does not include the final nucleotide and may not include a greater number of 5' or 3' terminal nucleotides e.g. 2, 3, 4, 5, 10, 15, 20, 25, 30, 35, 40 nucleotides.

As used herein, the term "fidelity" refers to the percentage of final products of an assembly method (e.g. sequenced clones following assembly and transformation of the construct into bacteria) which match the target sequence.

As used herein, the term "representation" refers to the rate at which each base appears at a mixed position in a degenerate sequence. For example, for a standard 'N' position (i.e. a position where each of A, C, T, G are expected with equal probability), each base should appear with equal frequency—25% adenine (A), 25% guanine (G), 25% thymine (T), 25% cytosine (C).

The invention provides a method of assembling a target double stranded polynucleotide (DSP) sequence. The target polynucleotide sequence can be any double stranded polynucleotide. The target polynucleotide sequence is assembled by joining together at least a first DSP and a second DSP. At least one of the DSPs that is incorporated into the target polynucleotide sequence is produced from a single stranded polynucleotide (SSP) in step (ii) of the method by annealing a primer to the SSP and extending the primer via the action of a polymerase enzyme. The second DSP may also have been generated from an SSP using this method. Alternatively, the second DSP may be provided separately, for example in the form of a vector or chromosome. For example, a vector may be provided in linearised form with one or both termini comprising regions which are complementary with regions located at one or both termini of the first DSP. The target polynucleotide sequence may be assembled from more than two DSPs, for example at least 3, 4, 5, 6, 7, 8, 9 or 10 DSPs. The target polynucleotide sequence could be assembled from tens of DSPs, hundreds of DSPs or even thousands of DSPs.

In some embodiments, the target polynucleotide sequence is assembled from a population of DSPs generated in step (ii). All DSPs in the population of DSPs are generated from a population of SSPs provided in step (i) by polymerase-mediated primer extension. The second DSP may or may not be a DSP of the population generated in step (ii). When a target polynucleotide sequence is assembled from a population of DSPs, one or more additional DSPs which are not part of the population of DSPs generated in step (ii) may also be incorporated into the target polynucleotide sequence. Population and non-population DSPs can be assembled in any desired order to generate a target polynucleotide sequence. For example, the population of DSPs could be joined together as a continuous sequence and a non-population DSP could be joined to one end or both ends of the resulting sequence to form the target polynucleotide sequence. Alternatively, for example, population DSPs could be joined at both termini to non-population DSPs to form a target polynucleotide sequence comprising population DSPs interspersed with non-population DSPs. In one embodiment, one or more target polynucleotide sequences are constructed from one or more DSPs of the population joined to at least one other DSP of the population. In one embodiment, one or more target polynucleotide sequences are constructed from one or more DSPs of the population joined to at least one other DSP that is not a DSP of the population.

In one embodiment, the population of DSPs consists of a number of DSPs "n", and n−2 DSPs are joined to two other DSPs of the population in step (iii) of the method. The remaining two DSPs may each be joined to one other DSP in the population and optionally to another DSP that is not from the population. In this way, a continuous sequence comprising the DSPs of the population could be inserted into a non-population DSP such as a vector. The DSPs assemble in the correct order and direction by virtue of their complementary regions. This is discussed in more detail below.

Advantageously, the method of the present invention can be used to assemble multiple identical target polynucleotide sequences simultaneously and/or assemble multiple different target polynucleotide sequences simultaneously. This is done by providing an SSP or a population of SSPs corresponding to each target polynucleotide sequence, and carrying out the method steps for each starting SSP or population of SSPs simultaneously. The correct assembly of each target polynucleotide sequence is made possible by virtue of specific complementarity between the DSPs corresponding to that target polynucleotide sequence.

The method of the invention can be used to assemble libraries of target polynucleotide sequences. Here, the term library is used to describe a plurality of unique polynucleotide sequence designs that can each be mapped back to a single degenerate polynucleotide sequence design. A polynucleotide sequence design is termed degenerate if it can be used to described a plurality of unique polynucleotide sequences.

For example, in one embodiment, a degenerate target polynucleotide design may be described using a well-known nucleotide notation developed by the International Union of Pure and Applied Chemistry (IUPAC). The notation is described in the table below.

| IUPAC Notation | Corresponding nucleotide base(s) | Notation type |
| --- | --- | --- |
| A | A | Non-degenerate |
| C | C | Non-degenerate |
| G | G | Non-degenerate |
| T | T | Non-degenerate |
| U | U | Non-degenerate |
| R | A or G | Degenerate |
| T | C or T | Degenerate |
| S | G or C | Degenerate |
| W | A or T | Degenerate |
| K | G or T | Degenerate |
| M | A or C | Degenerate |
| D | A or G or T | Degenerate |
| H | A or C or T | Degenerate |
| V | A or C or G | Degenerate |
| N | A or C or G or T | Degenerate |

For example, in the context of an IUPAC-described polynucleotide sequence, the symbol "W" can be mapped to both "A" and "T". Therefore, the degenerate polynucleotide sequence design "WAT" has two possible physical manifestations—"AAT" and "TAT". The polynucleotide sequence design "ANC" has four physical manifestations "ATC", "AAC", "AGC" and "ACC". The polynucleotide sequence design "NNN" has 64 (4^3) potential physical manifestations. Alternatively, other notations may be employed to describe degenerate sequence designs that cannot be adequately described using the the IUPAC notation.

In one embodiment, the method of the invention is used to assemble one or more target polynucleotide sequences that can each be mapped back to one or more degenerate polynucleotide sequence designs. This population of assembled target polynucleotide sequences may comprise the entire repertoire of designs described by the degenerate polynucleotide sequence design or designs. Alternatively, the population of assembled target polynucleotide sequences may comprise a subset of the entire repertoire of designs described by the degenerate polynucleotide sequence design or designs.

Thus, in one aspect, the invention provides a method for the preparation of a library of target polynucleotide sequences, the method comprising simultaneously producing a plurality of different target polynucleotide sequences using the method of the first aspect of the invention. The library of polynucleotide sequences may correspond to one or more degenerate polynucleotide sequence designs.

Once the target polynucleotide sequence or plurality of target polynucleotide sequences have been generated, these may be subjected to one or more further processing steps. For example, target polynucleotide sequences can be amplified using PCR, subjected to sequence verification, and/or transformed into a host cell using any suitable technique known in the art.

Generation of DSPs

An SSP is converted into a DSP in step (ii) by annealing a primer to the SSP and extending the primer by the action of a polymerase enzyme. The SSPs comprise at least one primer annealing site. A primer annealing site may be provided at one or both termini of the SSP. Preferably, each SSP comprises a single primer annealing site and is converted to a DSP using a single primer extension reaction whereby a single primer is annealed to the SSP and extended by the action of a polymerase enzyme.

In one embodiment (see FIG. 2), a primer may be covalently joined to its corresponding SSP. The covalent attachment of the primer to the SSP may be achieved during SSP synthesis. Covalently linked primer sequences may additionally comprise a hairpin motif that, through the formation of an intramolecular secondary structure, permits the annealing of the primer to the SSP. Once annealed, the primer may be extended via the action of a polymerase to yield a DSP. The hairpin motif may include one or more cleavable sites (e.g. uracil bases) that allow its subsequent removal. These cleavable hairpin primers may be added to either one or both ends of the DSP. The cleavable sites may be positioned such that an overhang of a predetermined design is formed after cleavage has take place. In some embodiments, this process may be conducted when one or more nucleotide bases in the SSP are immobilised onto a solid support. There are several advantages associated with this embodiment. Firstly, covalently linking the primer to the SSP increases the probability that the SSP will be converted into a DSP. Secondly, with the primer covalently bound to the SSP, there is a reduced probability of side reaction products being formed through mis-annealing of the primer. Thirdly, it enables the scarless removal of the DSP's primer annealing site. As a consequence of this, it is possible to assemble target polynucleotide designs that contain higher levels of degeneracy. A further advantage of this embodiment is that by positioning uracil sites at particular positions within the hairpin primer is possible to conduct the polymerase-mediated primer extension reaction with a polymerase variant that would otherwise stall at uracil sites.

The primer annealing site may be a region of the SSP that is derived from the target polynucleotide sequence. Where a population of SSPs are used, some or all of the SSPs in the population may comprise a universal primer annealing site, such that the same primer sequence can be used to convert the SSPs to DSPs. The primer annealing site and one or more bases surrounding it may be removed after conversion of the SSP to DSP. The primer will comprise the reverse complement sequence of the primer annealing site. A primer may additionally comprise nucleotides at its 5' terminus which do not anneal to the SSP. Primers can be ordered from a number of commercial suppliers (e.g. Thermo Fisher, Eurofins MWG Operon, Sigma-Aldrich, Integrated DNA Technologies (IDT)). Typically, the primer annealing temperature will be in the region of about 50° C. to about 72° C. with the annealing temperature depending on a number of factors, including sequence-specific parameters such as the primer's GC content and length as well as factors such as the buffer in which the PCR reaction will take place. An optimum temperature for a particular primer/SSP combination can be predicted computationally or determined empirically by assessing DSP yield at a range of annealing temperatures. The yield of DSP reduces at higher annealing temperatures because less primer will anneal to the SSPs. However, it is preferable to use the highest annealing temperature possible before the DSP yield drops to minimise non-specific primer annealing. There are a number of methods that may be used to interrogate the quality of an SSP to DSP conversion reaction. For example, reaction products may be sized by methods such gel electrophoresis, mass spectroscopy or capillary electrophoresis. The presence of heteroduplexes in the reaction product may be detected using kits such as a the SURVEYOR Mutation Detection Kit (IDT).

Extension of the primer is carried out by a polymerase enzyme. Examples of suitable polymerases include, but are not limited to, Pfu polymerase (Stratagene), PfuTurboCx Hotstart DNA polymerase (PfuCx) (Stratagene), Hotmaster Taq (Eppendorf), Taq (Invitrogen), Phusion (Finnzymes), Pwo (Roche) and Q5 polymerase (NEB). Any standard reagents such as buffers, DMSO and dNTPs can be used in the conversion step and reaction conditions are defined by the chosen polymerase in line with the accepted manufacturer's guidelines.

Amplification, for example using PCR, is preferably not used to generate DSPs from SSPs. There are several advantages to avoiding DSP amplification prior to assembly of the target polynucleotide sequence. For example, DSPs produced by single primer extension (as opposed to amplification) will have greater fidelity due to (i) reduced levels of heteroduplex formation, (ii) reduced levels of incorrect base incorporation and (iii) the avoidance of PCR side reactions caused by off-target annealing.

In an SSP to DSP conversion reaction, using single primer extension (rather than PCR) is particularly advantageous in the context of library creation. For example, when a population of SSPs is converted into a population of DSPs using PCR, one SSP may give rise to multiple DSPs. Where PCR results in differential SSP enrichment, some designs may be over or under represented in the resulting DSP population. In contrast, in the single primer extension approach one SSP is converted into one DSP. Therefore the resulting population of DSPs should comprise a less biased sampling of the corresponding SSP population. In contexts where high DSP diversity is desirable (e.g. in library creation), a large population of unique SSP designs can be converted to a corresponding population of unique DSP designs using the single primer extension method. Single primer extension may also be advantageous when producing highly repetitive sequences. Exposing these sequences to multiple rounds of melting and annealing increases the likelihood of mis-annealing of primers and heteroduplex formation between SSPs, with subsequent polymerase extension. The resulting side reaction products may (i) inhibit the SSP to DSP conversion reaction, (ii) interfere with target polynucleotide sequence assembly and (iii) give rise to non-target polynucleotide sequences. If the target polynucleotide sequence is to be transformed into a cell, the presence of non-target polynucleotide sequences in the reaction product can give rise to a population of cells that contain both target and non-target polynucleotide sequences which is particularly disadvantageous.

Once generated, DSPs may be subjected to one or more error removal steps and/or purified to remove undesirable reaction components or side reaction products. For example, an error removal step may comprise the removal of DSPs that contain mismatches and therefore comprise heteroduplexes. Such DSPs may be removed using mismatch-binding agents (e.g. MutS) or alternatively by exploiting differences in electrophoretic mobility. Alternatively, a heteroduplex-specific nuclease may be used to cleave heteroduplexes in the DSP population. Cleaved heteroduplexes may then be removed using one or more physical separation techniques. Such separation techniques may comprise electrophoretic preparative techniques (e.g. PAGE) or HPLC. Analytical-scale techniques (e.g. mass spectroscopy or HPLC) may be used to subsequently evaluate the success of the aforementioned heteroduplex removal processes. In addition, a DSP sample may be subjected to a buffer-exchange reaction to confer compatibility with a downstream reaction step.

Figure 3:
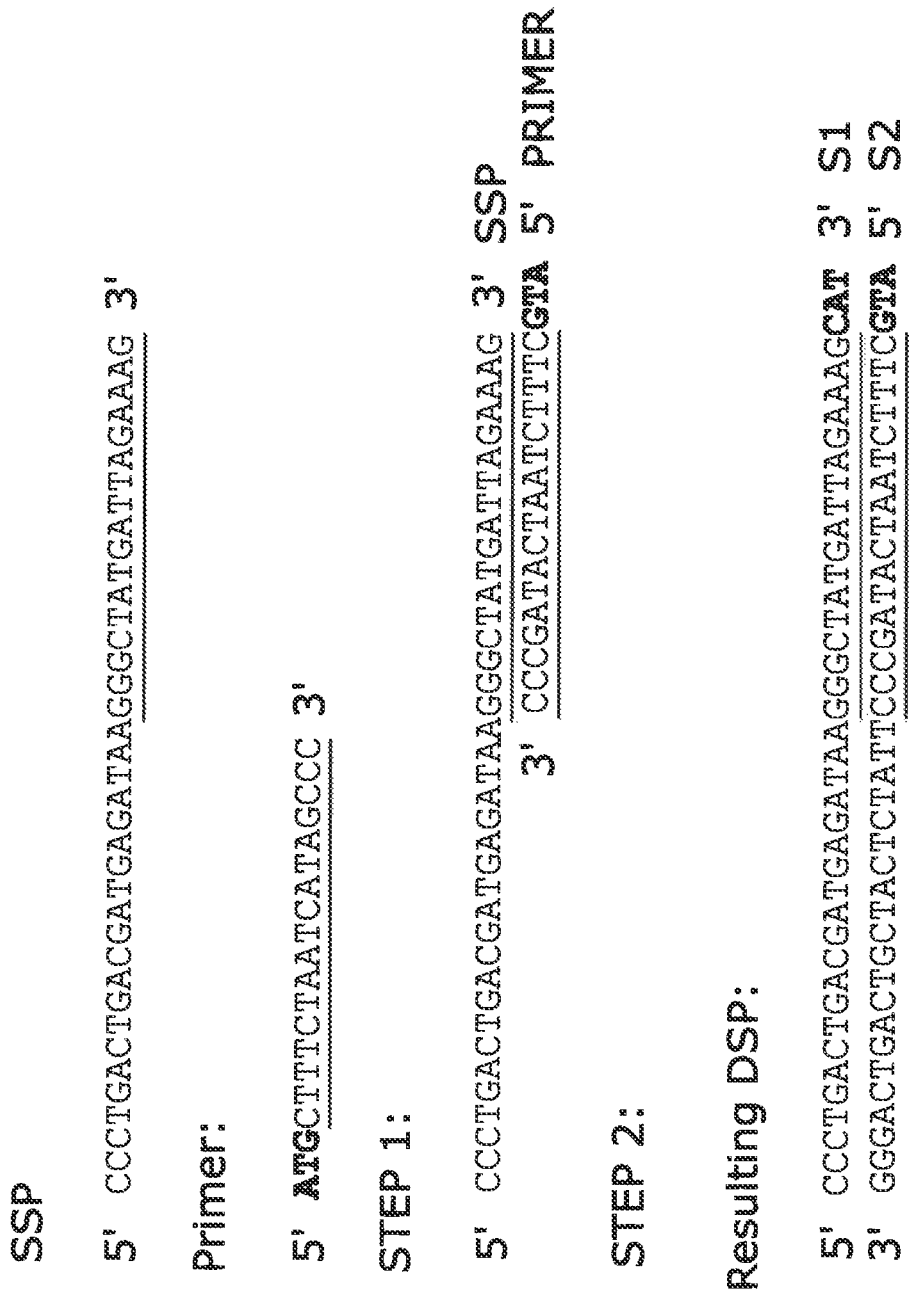
FIG. 3 shows an embodiment in which a primer comprises an annealing sequence and an overhang sequence which does not anneal to an SSP.

An SSP may comprise or consist of the polynucleotide sequence of one strand of the DSP into which that SSP is converted. In some embodiments the DSP comprises additional polynucleotide sequence and therefore, in such embodiments, the SSP will not comprise the full polynucleotide sequence of one strand of the DSP into which it is converted. For example, the SSP may comprise at least 70%, at least 80%, at least 90%, at least 95%, at least 96%, at least 97%, at least 98%, or at least 99% of the polynucleotide sequence of one strand of the DSP into which that SSP is converted in step (ii). Additional polynucleotide sequence forming a strand of the DSP that is not derived from the SSP may be derived from the primer. In such embodiments, the primer may comprise an annealing sequence and an overhang sequence. The annealing sequence anneals to the SSP and the overhang sequences does not anneal to the SSP and generates an overhang. One exemplary embodiment of this is shown in FIG. 3. In this embodiment, the SSP has a primer binding site (underlined). The primer has a sequence (also underlined) which is the reverse complement of the primer binding site and an additional sequence (in bold) at its 5' end which does not anneal to the SSP and forms an overhang once the primer is annealed to the SSP.

In this example, the primer contains a 5' overhang. This overhang, comprises a region (ATG) that is not complementary to the 3' region of the SSP. In a first step (step 1), the primer anneals to the SSP. In a second step (step 2), the primer is extended by a polymerase in the SSP to DSP conversion reaction. The resulting strands are termed S1 (derived from the SSP) and S2 (derived from the primer). The S1 strand is also extended by polymerase in the 5'-3' direction which adds the sequences CAT to the S1 strand at its 3' end. CAT is the reverse complement sequence of the non-complementary region of the primer. The sequence S1 comprises CCCTGACTGACGATGAGATAAGGGCTAT-GATTAGAAAG (SEQ ID_NO:1)+CAT. Therefore S1 comprises the SSP and the reverse complement of the 5' non-complementary sequence of the primer. Thus, in one embodiment, one strand of a DSP formed from an SSP in step (ii) comprises the SSP and the reverse complement of any 5' region of the SSP's corresponding primer that does not anneal to the SSP.

As illustrated by the above example, step (ii) of the method of the invention may include polymerase mediated extension of the SSP in the 5' to 3' direction in addition to extension of the primer. Extension of the primer and the SSP may occur simultaneously.

Figure 4:
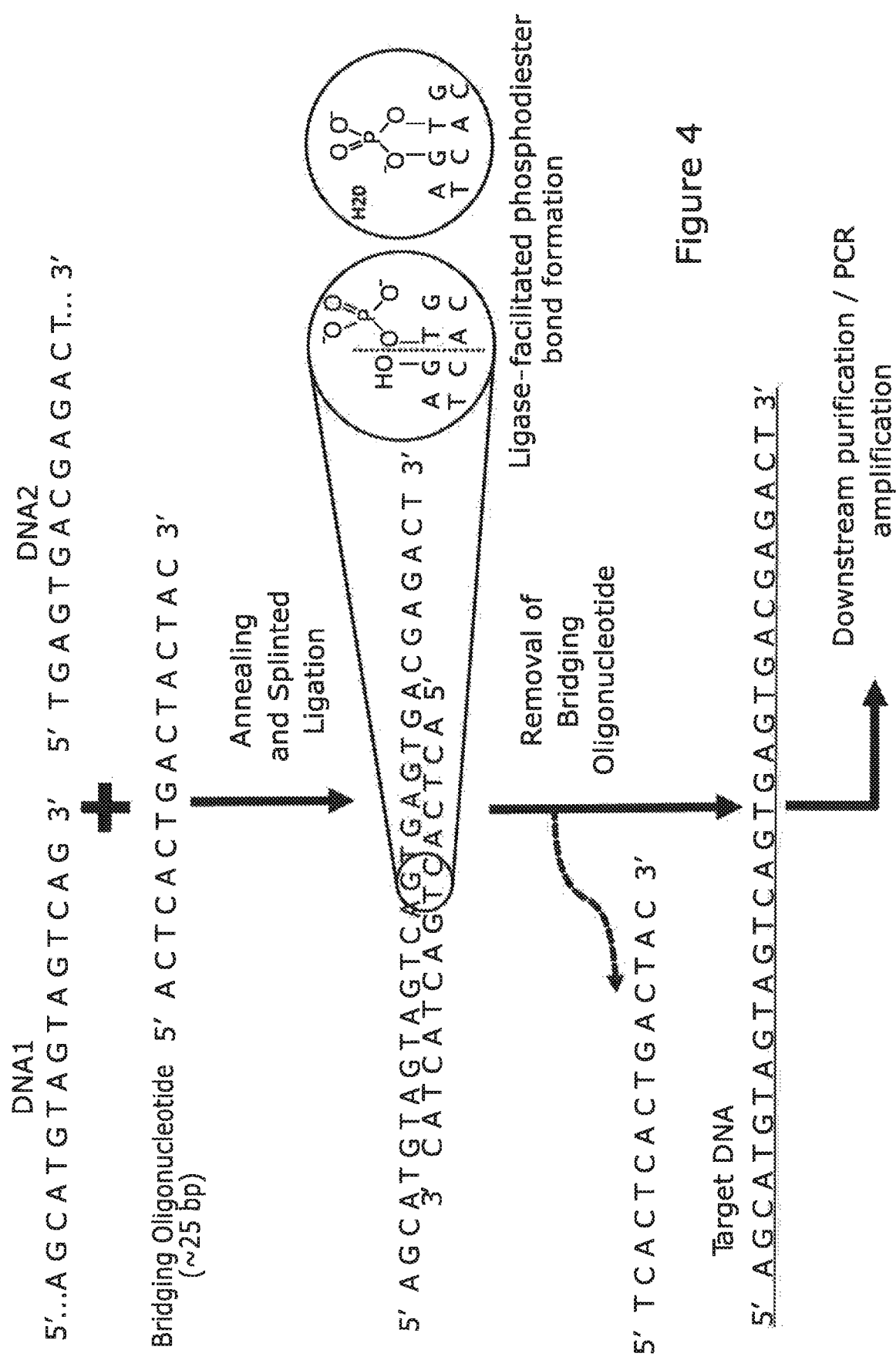
FIG. 4 shows an oligonucleotide ligation method.

The SSPs can be produced by chemical synthesis methods known in the art. Chemically synthesised SSPs having desired sequences can be ordered from a range of commercial suppliers (e.g. IDT, Bio-Synthesis Inc). With present techniques, commercial suppliers typically offer SSPs up to a length of 200-400 bases. Should longer SSPs be required, these can be produced using an established technique called oligonucleotide ligation. This is described with reference to FIG. 4 in which the two oligonucleotides to be joined together are labelled as DNA1 and DNA2. A splinted ligation reaction can be used to join two oligonucleotides together to form a longer polynucleotide sequence. One of the oligonucleotides must be unmodified at its 3' end and possess a 3' hydroxyl group, and the other must have a 5' phosphate group attached. The ligation reaction is catalysed by the enzyme DNA ligase and requires DNA1 and DNA2 to be brought together by simultaneous hybridization to a complementary bridging oligonucleotide. The ligation reaction is sometimes used to assemble genes from long oligonucleotides or PCR products (a 5'-phosphate group can be introduced into a PCR product simply by using a 5'-phosphate-labelled PCR primer). DNA1 and DNA2 can be any length, e.g. 100 mer synthetic oligonucleotides or 500 mer PCR products, whereas the bridging oligonucleotides need only be a short oligonucleotide of around 25 bases in length. Multiple ligation reactions can be carried out simultaneously using a mixture of DNA fragments and bridging oligonucleotides in order to assemble a long piece of DNA from several fragments.

The SSPs to be used in the method of the invention may have a length of anywhere from about 30 bases to about 1000 bases or more, for example at least 30, 40, 50, 100, 200, 300, 400, 500, 600, 700, 800, 900 or 1,000 bases long.

Where a population of SSPs is converted into a population of DSPs, the SSPs may be spatially separated from one another for the conversion step. For example, the SSPs may be immobilised on a solid support. SSPs, which are fixed to a solid support, may additionally comprise a cleavable linkage that allows the release of the DSP. For example, one or more SSPs may be fixed to a solid support via photocleavable linkages. In this example, a radiation source (e.g. laser) may be used to release the resulting DSPs from the solid support. This may be achieved in a highly controlled, precise and programmable manner by moving the laser (and therefore the site of irradiation) relative to the solid support. The advantage of this approach is that it allows different DSPs to be selectively released from a population of immobilised DSPs. Once released, from the solid support the DSPs free to particulate in a DSP-joining reaction via their complementary regions. Alternatively, spatial separation may be achieved by compartmentalisation. For example, each SSP could be converted to a DSP in a separate reaction vessel. Alternatively, spatial separation may be achieved by microdroplet handling. Such techniques may be employed to produce target sequences in a scalable and high throughput fashion.

Joining of the DSPs Via Complementary Sequences

The target polynucleotide sequence is assembled by joining together at least two DSPs in the correct order and orientation in a process termed "directional assembly". The directional assembly of multiple DSP subparts to form a target polynucleotide sequence is facilitated via the careful design of one or both terminal regions of each DSP. A first DSP can be joined to a second DSP via the interaction of terminally-located complementary sequences. For this interaction to take place, a terminally-located sequence on one DSP must be free to interact with a complementary terminally-located sequence on the second DSP. Preferably, no other components such as single stranded bridging oligonucleotides are required to facilitate assembly of the target polynucleotide sequence. Preferably, only DSPs that are to be joined together directly will comprise sequences that are complementary to one another. However, in some cases, DSPs that are not to be joined together (directly) may comprise complementary sequences. In such circumstances, the complementary sequences will not be capable of binding one another during the assembly step e.g. complementary sequences may be sequestered in a non-accessible state in a non-terminal region of the DSP. In some embodiments, DSPs that are not to be joined together directly will not comprise sequences that are complementary to one another. Multiple identical target sequences may be assembled simultaneously and hence there will be a pool of identical DSPs for each position in the target polynucleotide sequence. For example, if the target polynucleotide sequence is linear and comprises, in sequence, DSP1, DSP2, and DSP3, there may be a pool of identical DSP1 fragments, a pool of identical DSP2 fragments and a pool of identical DSP3 fragments. Any of the DSP1 fragments can join to any of the DSP2 fragments via complementary sequences but DSP1 fragments cannot join to DSP3 fragments because they do not comprise sequences that are complementary to one another. The DSPs are thus designed to include specific complementary sequences that will ensure that a given DSP can only join to the appropriate DSP or DSPs in order to form the target sequence.

A complementary sequence may be about 1 to about 50 bases in length, more preferably about 3 to about 25 bases in length. For example a complementary sequence may be at least about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 bases in length. Each terminally-located complementary sequence of non-identical DSPs should be unique and may differ from complementary sequences of other DSPs by at least 1, 2, 3, 4, 5 or more bases. This is to ensure that DSPs can only join to the correct partner DSP or DSPs during the assembly of the target polynucleotide sequence. As mentioned above, pools of identical DSPs may be present when multiple identical target polynucleotide sequences are assembled. In this case identical DSPs will have identical complementary regions but this does not matter as identical DSPs can be substituted for one another.

In one embodiment, a DSP generated in step (ii) of the method is assembled into a linearised vector, wherein the junctions between the DSP and the vector are determined by their respective complementary regions. Multiple DSPs may be inserted into a linearised vector in this way. For example, a population of DSPs generated in step (ii) of the method is assembled into a linearised vector, wherein one end of the vector joins to a first DSP in the population and the other end of the vector joins to a second DSP in the population. Any number of additional DSPs may be incorporated into the target polynucleotide sequence between the two ends of the linearised vector.

Figure 5:
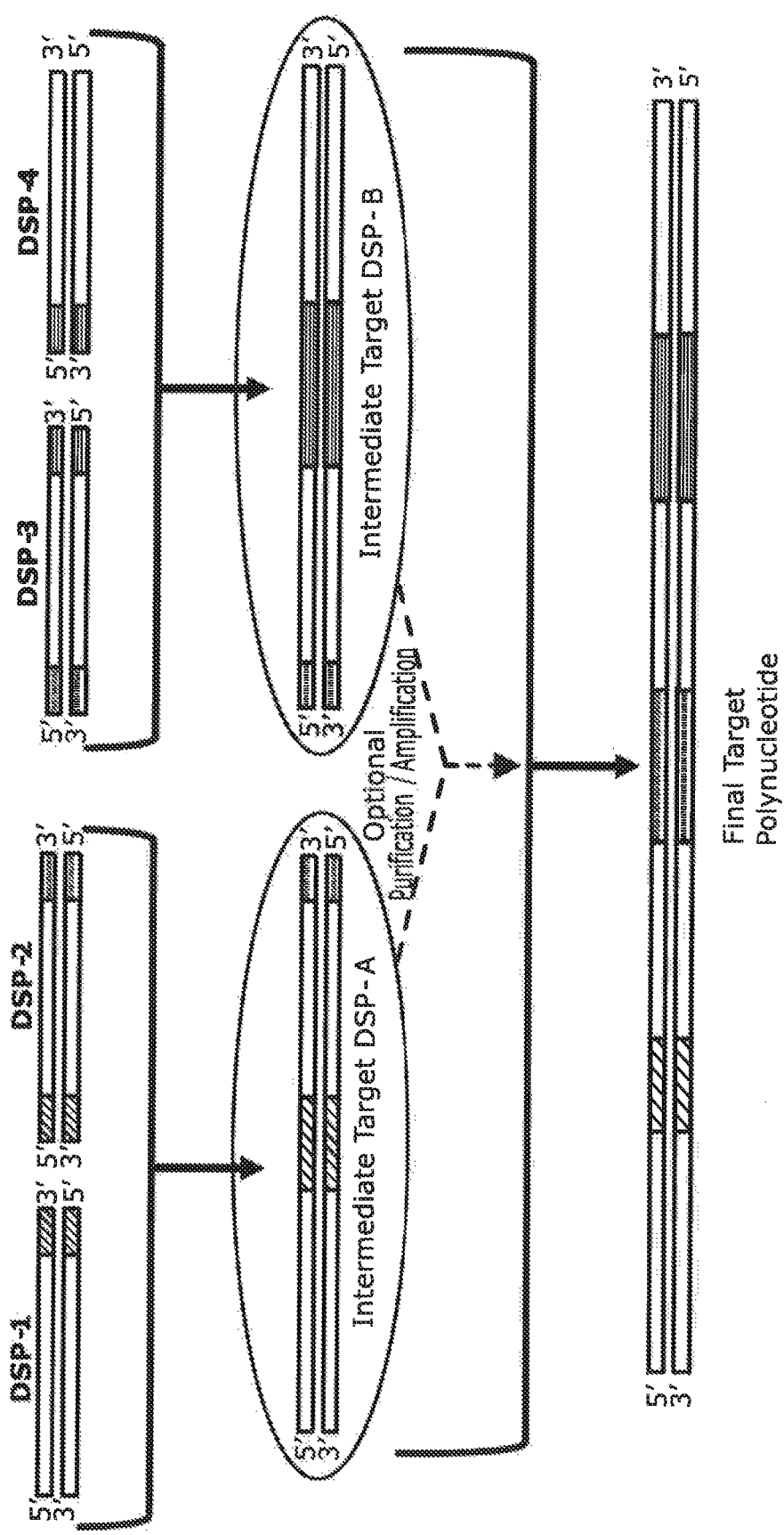
FIG. 5 shows a hierarchical assembly method for producing a target polynucleotide sequence via intermediate target DSPs.

In one embodiment, a target polynucleotide sequence is assembled via the hierarchical assembly of multiple DSPs. Here the term 'hierarchical assembly' is used to describe a process wherein a final target polynucleotide sequence is assembled via the sequential assembly of one or more intermediate target sequences. For example, as shown in FIG. 5, in a first step, two different DSP pairs could be used to build two intermediate target polynucleotide sequences. These intermediate target polynucleotide sequences, which comprise DSPs, could then be joined in a second step to produce the final target polynucleotide sequence. The intermediate target polynucleotide sequences may optionally be amplified and/or purified prior to being joined to another DSP in the hierarchical assembly process.

Complementary regions may be provided as single stranded overhangs of either strand of the DSP. Thus, a single stranded overhang may be about 1 to about 50 bases in length, more preferably about 3 to about 25 bases in length, for example at least about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 bases in length. Single stranded overhangs of non-identical DSPs should be unique and may differ from single stranded overhangs of other DSPs by at least 1, 2, 3, 4, 5 or more bases. Each DSP may have an overhang at one or both termini and may have any combination of 5' and 3' overhangs.

An overhang may be generated using the enzymatic removal of a portion of one strand of the double stranded sequence after the DSP has been generated. If overhangs are to be generated, the SSPs may be designed such that the DSPs into which they are converted are targeted at a specific site to expose a desired overhang. Overhangs can be generated using a number of known enzymes and reagents. Examples include USER™ (Uracil-Specific Excision Reagent) enzyme mix, Type IIS restriction enzymes, and exonucleases. In a preferred embodiment, overhangs are generated with a mixture of enzymes containing a uracil DNA glycosylase (UDG) (e.g. *E. coli* G/U mismatch-specific DNA glycosylase (EC:3.2.2.28)) and a DNA glycosylase-lyase endonuclease (e.g. *E. coli* Endonuclease 8) hereafter termed a "USER enzyme mix". UDG catalyses the excision of a uracil base, forming an abasic (apyrimidinic) site while leaving the phosphodiester backbone intact. The lyase activity of Endonuclease VIII breaks the phosphodiester backbone at the 3' and 5' sides of the abasic site so that base-free deoxyribose is released. USER enzyme mixes are available from commercial suppliers (e.g. USER™ Enzyme from New England Biolabs (NEB)). The USER™ Enzyme mix contains Uracil DNA glycosylase (UDG) and the DNA glycosylase-lyase Endonuclease VIII.

Polynucleotide assembly conducted using a USER enzyme mix is termed "USER cloning". USER cloning relies on the presence of a uracil base at a position in a double stranded DSP. This may be introduced into the SSP design and/or into the primer design as described in Example 2. The uracil and all polynucleotide residues that are 5' of the uracil are removed by the USER enzymes, thereby generating an overhang. An example of a protocol for USER cloning is as follows. USER enzyme mix can be added to a reaction mix comprising equimolar DSPs to be assembled and the entire reaction mix may be incubated at 37° C. for 20 minutes to allow generation of overhangs by the USER enzyme mix and 21° C. for 20 minutes to allow the overhangs to anneal. Different temperatures may be required for the USER excision step and the annealing step. For example, if larger amounts of DSPs were included in the reaction mix, additional time may be required for the USER enzymes to generate the overhangs. Further information on USER cloning can be found in Bitinaite, J. et al. USER friendly DNA engineering and cloning method by uracil excision. Nucleic Acids Res. 35, 1992-2002 (2007), and Methods in Molecular Biology 643, Chapter 13 USER Cloning and USER Fusion: The Ideal Cloning Techniques for Small and Big Laboratories, Hussam H. Nour-Eldin, Fernando Geu-Flores, and Barbara A. Halkier.

Type IIS restriction enzyme cloning methods employ the enzyme's action of cutting outside its recognition site to allow scarless polynucleotide assembly. When applied to the methods disclosed herein, SSPs are synthesised with primer binding sites present at the 3' end to allow DSP formation, and enzyme recognition sites with adjacent terminal complementary sequences, at one or both termini, to allow assembly after restriction enzyme digestion. This process can be applied to more than two component DSPs. This can be achieved by including Type IIS restriction sites at both termini of an SSP. Since the overlaps are not contingent on the recognition sequence of the enzyme (which is removed upon restriction), each junction overhang can be designed to have specific complementarity to the adjacent DSPs that form the complete target polynucleotide sequence. Once the SSPs have been converted to DSPs, the entire target polynucleotide sequence can be assembled in one pot by adding the Type IIS restriction enzyme, to expose the specific overhangs. T4 ligase may optionally be added to join the parts together. An advantage of adding T4 ligase into the reaction is that it can increase yields of the target sequence. This is because two ligated DSPs will lack the Type IIS recognition sequence and therefore cannot be cut. In contrast, if the cleaved strand is re-ligated to its parent DSP, the Type IIS recognition sequence is re-formed and the resulting polynucleotide sequence can be re-cut by the restriction enzyme.

Figure 6:
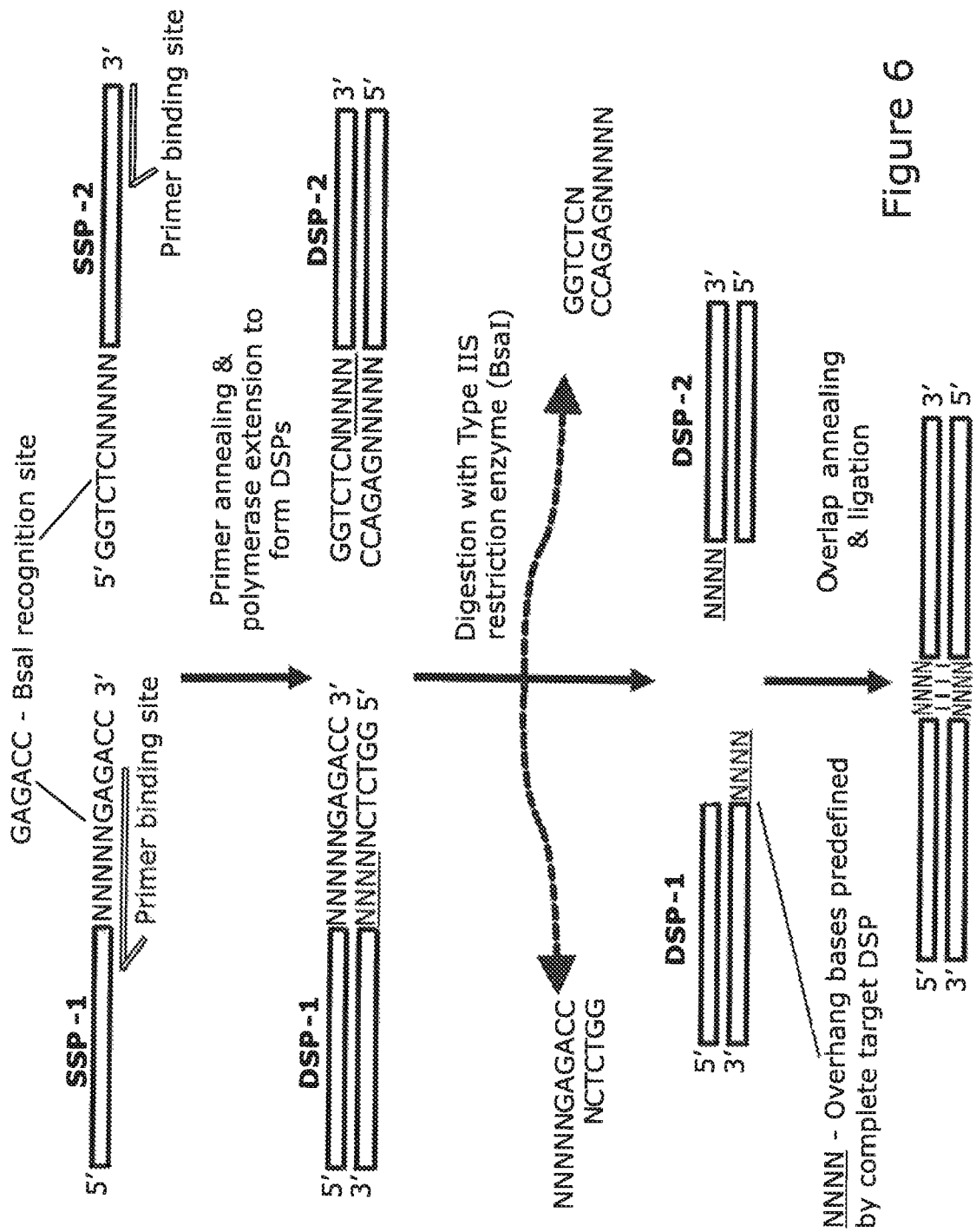
FIG. 6 shows an assembly method which utilises a Type IIS restriction enzyme to generate overhangs.

One embodiment of a Type IIS restriction enzyme based assembly method is illustrated in FIG. 6. In this example a target polynucleotide sequence comprising two DSPs, DSP-1 and DSP-2 is assembled. Primers are annealed to a first SSP, SSP-1, and a second SSP, SSP-2. The primers are extended using a polymerase to form DSP-1 and DSP-2. Both DSPs contain the recognition site for the Type IIS restriction enzyme BsaI at their terminal ends which are to be joined. The DSPs are digested with the Type IIS restriction enzyme BsaI which results in the exposure of complementary 4 base pair overhangs on adjacent DSPs (NNNN) and the removal of the BsaI recognition site. The complementary sequences are annealed to assemble the target polynucleotide sequence. Multiple DSPs can be assembled in a defined order simultaneously given that there is suitable specificity of each overhang sequence.

One embodiment of an exonuclease based assembly method, involves the incubation of a mixture of DSPs with an exonuclease enzyme (e.g. T5 Exonuclease), a polymerase enzyme (e.g. Phusion polymerase) and a thermostable ligase (e.g. Taq ligase). The exonuclease regresses one strand of the DSPs creating compatible overhangs with adjacent DSPs which anneal. Gaps caused by excessive regression are filled by the thermostable polymerase activity and the nicks in the backbone are repaired by the thermostable ligase. In instances in which overhangs are created by an exonuclease, the overhang length may be determined by reaction conditions.

In one embodiment the overhang is not generated using a restriction enzyme. The SSPs and/or the DSPs may not comprise a restriction enzyme recognition site. Advantages of using methods other than restriction enzyme based methods to generate the overhangs are that they avoid off-target cutting, enable programmable overhang length and give better use of synthesis capacity.

In one embodiment, overhangs can be generated by incorporating tetrahydrofuran abasic sites into the SSP and the primer, as in Autosticky PCR. For example, an overhang can be created at the 5' terminus of the SSP by incorporating a tetrahydrofuran abasic site into the SSP at the 5' terminus. During the polymerase extension reaction, the polymerase will reach this tetrahydrofuran abasic site and stall, causing the polymerase reaction to cease, leaving an overhang. An overhang can be generated at the 3' terminus by using a primer that comprises the desired overhang sequence and an annealing sequence with a tetrahydrofuran abasic site between these sequences. The annealing sequence anneals to the SSP and the overhang sequence does not anneal to the SSP. The subsequent extension of the primer forms the DSP, with the abasic site in the primer preventing the extension of the opposite strand, leaving an overhang. The combination of these two techniques results in the formation of overhangs at both termini of the DSP. The action of polymerases at these abasic sites vary, for example, Taq polymerase will add at least 1 base before dissociating from the DNA, whereas polymerases such as Pfu and Vent do not. This is important during the design of the SSPs and primers since the inclusion of a base opposite the abasic site greatly increases the efficiency of the assembly. Since Pfu and Vent do not introduce a base opposite the abasic site, one must be included in the complementary overhang of the adjacent DSP. The opposite is true of Taq, where no additional base in the complementary overhang is needed. Upon transformation of the fully assembled DSP into a host cell, these abasic sites are repaired by host enzymes in vivo. More information on autosticky-PCR techniques can be found in Gál J et al. Directional cloning of native PCR products with preformed sticky ends (autosticky PCR). Mol Gen Genet. 569-73. 1999 January.

Figure 7:
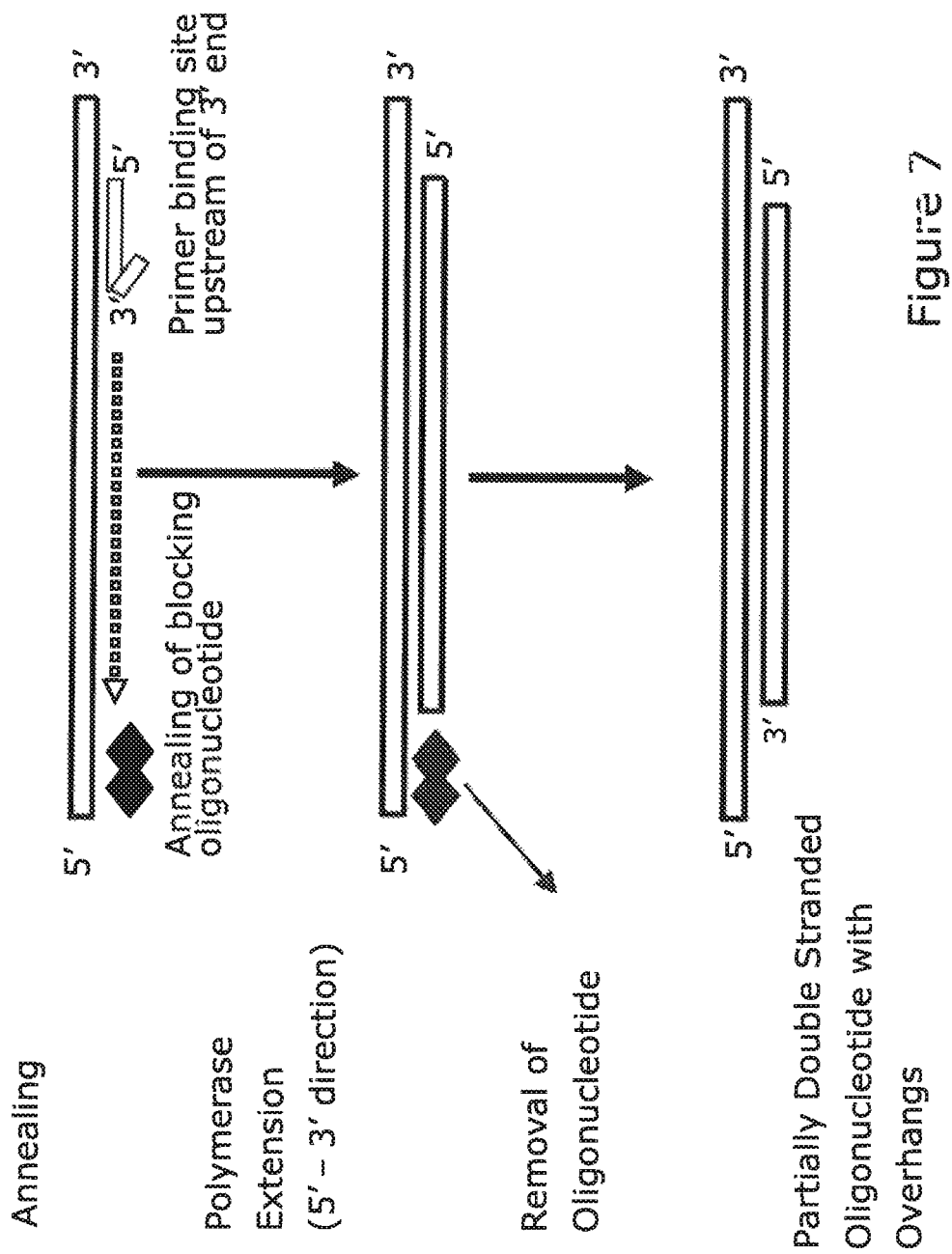
FIG. 7 shows a method of generating overhangs using modified polymerase extension.

In an embodiment, overhangs can be generated by using a modified polymerase extension reaction, at step (ii) of the method. For example, an overhang can be generated by annealing a primer upstream of the 3' terminus of the SSP such that when the primer is extended in the 5' to 3' direction, a region of single stranded sequence is left at the 5' end of the primer. Alternatively or additionally blocking oligonucleotides can be used. Blocking oligonucleotides are comprised of modified oligonucleotides to prevent DNA polymerisation by a DNA polymerase at a specific location. These modifications include but are not restricted to Locked Nucleic Acids (LNA), chemically reversed nucleotides, 3' phosphate groups, 3'-Spacer C3 CPGs and Peptide Nucleic Acids (PNA). To form an overhang, a blocking oligonucleotide may be annealed to a sequence of the SSP that is to form an overhang, as shown in FIG. 7, step 1. The primer is annealed and extended in the normal way to form a DSP until the blocking oligonucleotide is reached, at which point polymerisation ceases (step 2 of FIG. 7). The blocking oligonucleotide is then removed to leave an overhang (step 3 of FIG. 7). In this embodiment, the primer was also annealed upstream from the 3' region of the SSP. The combination of these techniques results in the formation of overhangs at both ends of the DSP.

Figure 8:
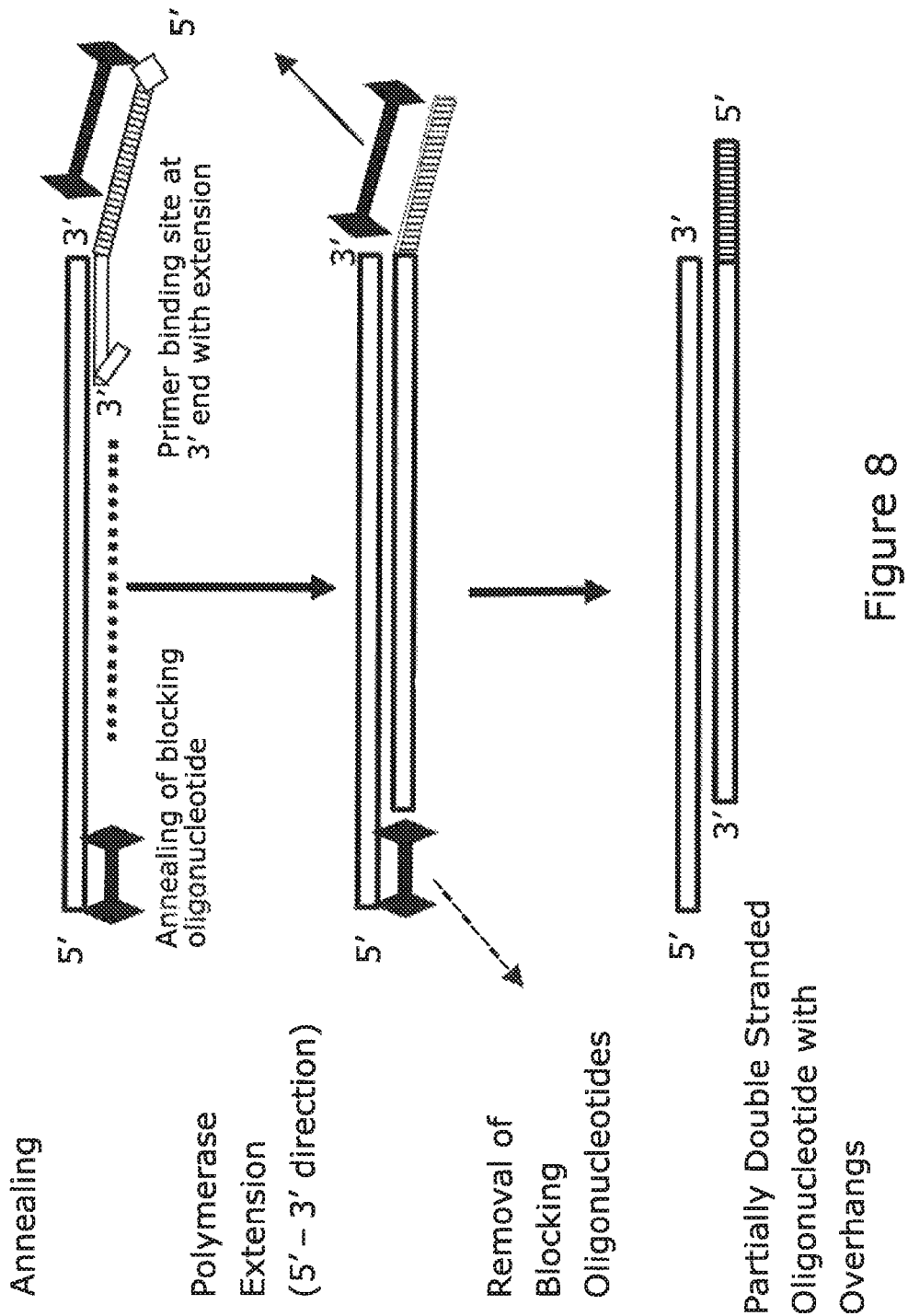
FIG. 8 shows a method of generating overhangs using modified polymerase extension.

Another embodiment involves using a primer which comprises the desired overhang sequence and an annealing sequence. The annealing sequence anneals to the SSP and the overhang sequence does not anneal to the SSP (as shown in FIG. 8, step 1). A blocking oligonucleotide is annealed to the overhang sequence of the primer. Optionally, a second blocking oligonucleotide can be annealed to the SSP as in the embodiment shown in FIG. 8. The primer is extended to form a DSP. Finally, the blocking oligonucleotides are removed to leave overhangs as shown in FIG. 8, step 3. Any combination of the techniques listed above, and variants thereof, can be used to generate overhangs. The method of the invention may involve joining a DSP produced in step (ii) from an SSP to a second DSP that is not produced from an SSP. DSPs that are not generated from SSPs may comprise overhangs and these can be generated using any of the methods disclosed herein.

Figure 9:
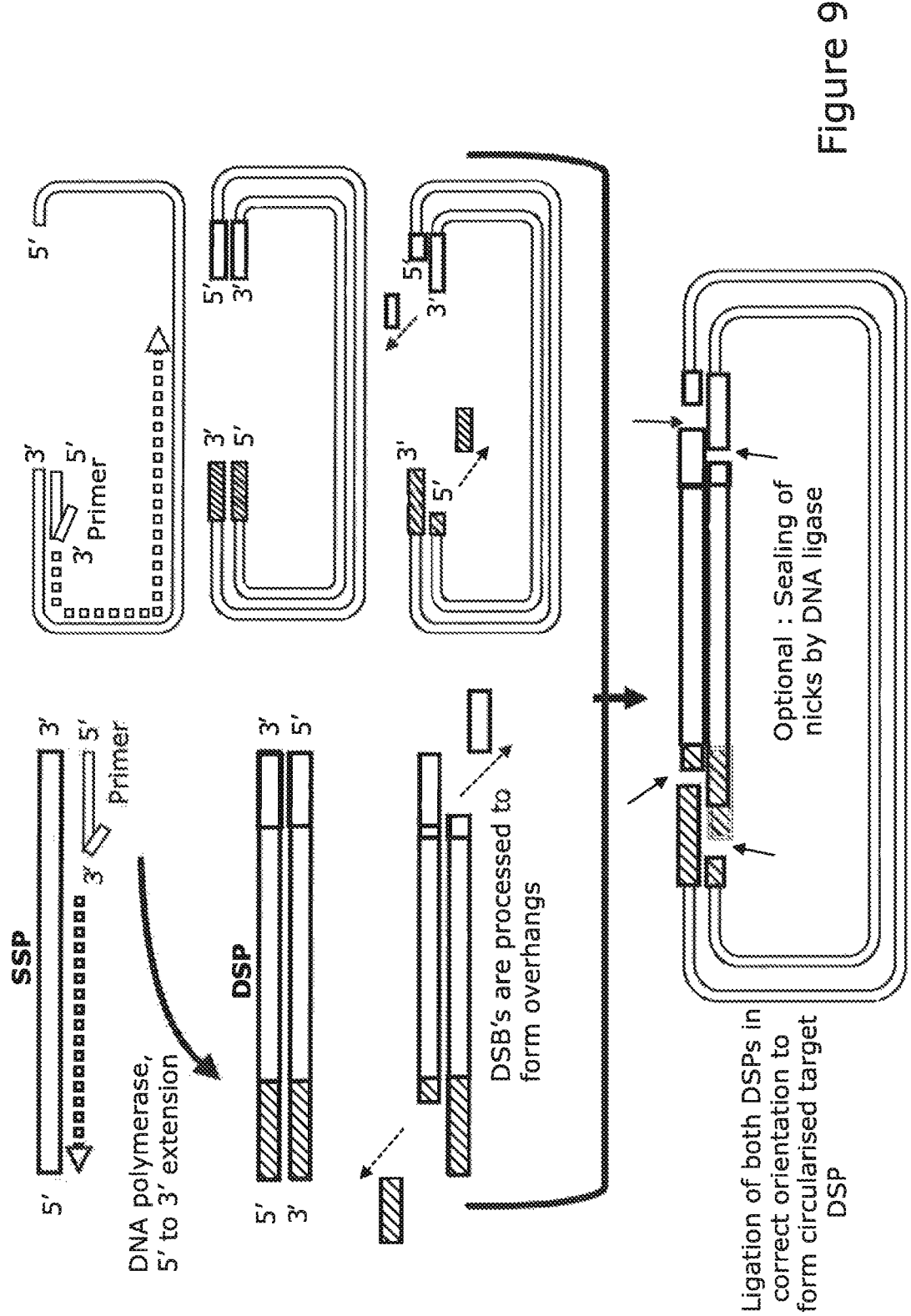
FIG. 9 is a schematic representation of one embodiment of an assembly method.

FIG. 9 shows one example of a complete assembly method involving the use of complementary overhangs to assemble a circularised target polynucleotide sequence from two component DSPs. A primer is annealed to the 3' end of an SSP at a primer annealing site and the primer is extended using DNA polymerase to form a first DSP. The first DSP is processed to form an overhang at each end. A second DSP is provided which has been similarly processed to generate overhangs which are complementary to the overhangs of the first DSP. The complementary overhangs are annealed such that the first DSP is inserted into the second DSP in the correct orientation to form circularised target polynucleotide sequence.

Although assembly of the target polynucleotide sequences can be achieved based on annealing of complementary overhanging sequences, assembled DSPs may further be ligated using a ligase enzyme. The ligase may be T3 DNA ligase, T4 DNA ligase, T7 DNA ligase, Taq DNA ligase, E. coli DNA ligase, Ampligase®, a Sso7-ligase fusion and any variant thereof, or any combination thereof.

Figure 10:
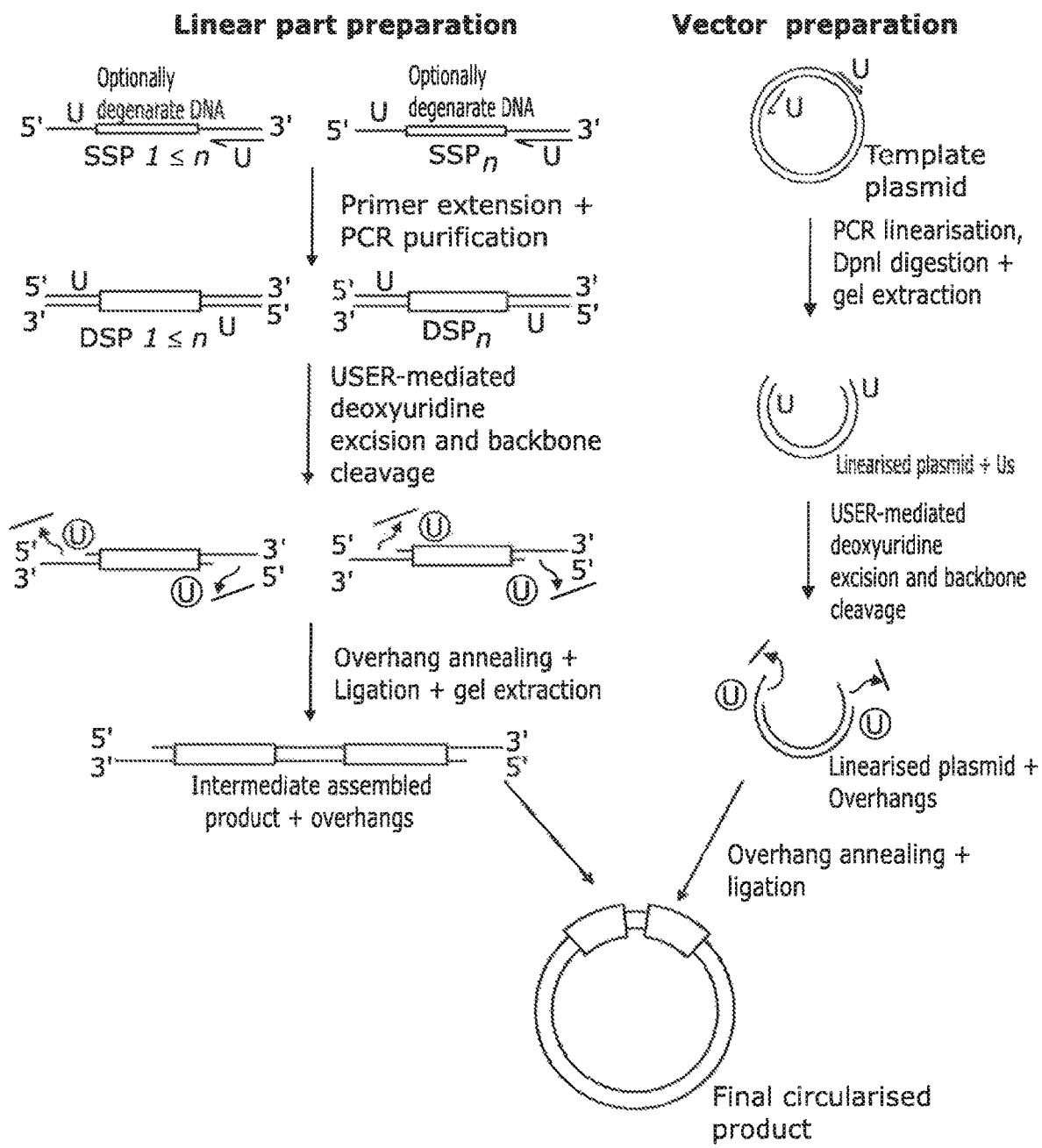
FIG. 10 is a schematic representation of an embodiment of a method of assembly, wherein an n-part linear polynucleotide is assembled into a circularised vector.

FIG. 10 shows an example of a method of assembly of an n-part linear polynucleotide into a circularised vector, according to embodiments of the invention. In this embodiment, 2 parts of a target sequence are explicitly shown as being assembled into a plasmid. The person skilled in the art would understand that the linear part (target sequence) may in fact comprise 3 or more double stranded polynucleotides (DSP1 to DSPn) and corresponding single stranded polynucleotides (SSP1 to SSPn), wherein design, generation and assembly of the DSPs follows the same principles. In particular, in the embodiment shown, a first single stranded polynucleotide (SSP1) and at least a second first single stranded polynucleotide (SSPn) are provided. Either or both of these SSPs may comprise one or more sections of degenerate DNA, for example, where library generation is required.

A single primer for each SSP (i.e. primers 1 to n), wherein each primer binds at a terminus of a SSP are then used to convert each SSP into their respective DSP through a polymerase-mediated extension of the primers.

Each DSP comprises a polynucleotide sequence that is complementary to a polynucleotide sequence of another DSP. Advantageously, these complementary sequences are unique to a single pair of DSPs, i.e. each pair of complementary sequences is present in only one pair of DSPs.

Overhangs are then generated on either side of each DSP. In this embodiment, the overhangs are generated by USER-mediated deoxyuridine excision. Therefore each SSP and each primer comprises a uracil nucleotide for recognition by the USER enzyme. Similarly, each SSP may comprise a uracil nucleotide at the opposite extremity from that where the primer binds. The overhangs comprise at least a portion of the sequences that are complementary between pairs of DSPs.

The target sequence is then assembled by annealing of the complementary sequences in the overhangs, and subsequent ligation of the fragments. Advantageously, as the complementary sequences in the overhangs are unique to a single pair of DSPs within the reaction, this assembly will result in specific ordering and directionality. This is a key advantageous feature of the methods of the invention, and it is not limited to any particular overhang generation and assembly method. A significant drawback of prior techniques for polynucleotide assembly is that ordering and directionality can often be compromised, resulting in 'shuffled' contaminating by-products that lead to reduced yield and fidelity in the reaction.

In parallel, a vector may be prepared for assembly with the linear product obtained above. In this embodiment, a plasmid is provided, together with specific primers comprising uracil nucleotides for overhang generation. Similarly to what is done for the fragments of the linear target sequence, the primers are designed such that, upon cleavage by USER-mediated deoxyuridine excision, overhangs are created that comprise sequences that are complementary to either terminus of the assembled target sequence. After PCR linearization, digestion and USER-mediated deoxyuridine excision, the linearised plasmid with overhangs can be assembled with the target sequence by annealing of the overhangs and ligation, similarly to what is done for any other DSP in the linear target assembly.

Figure 11:
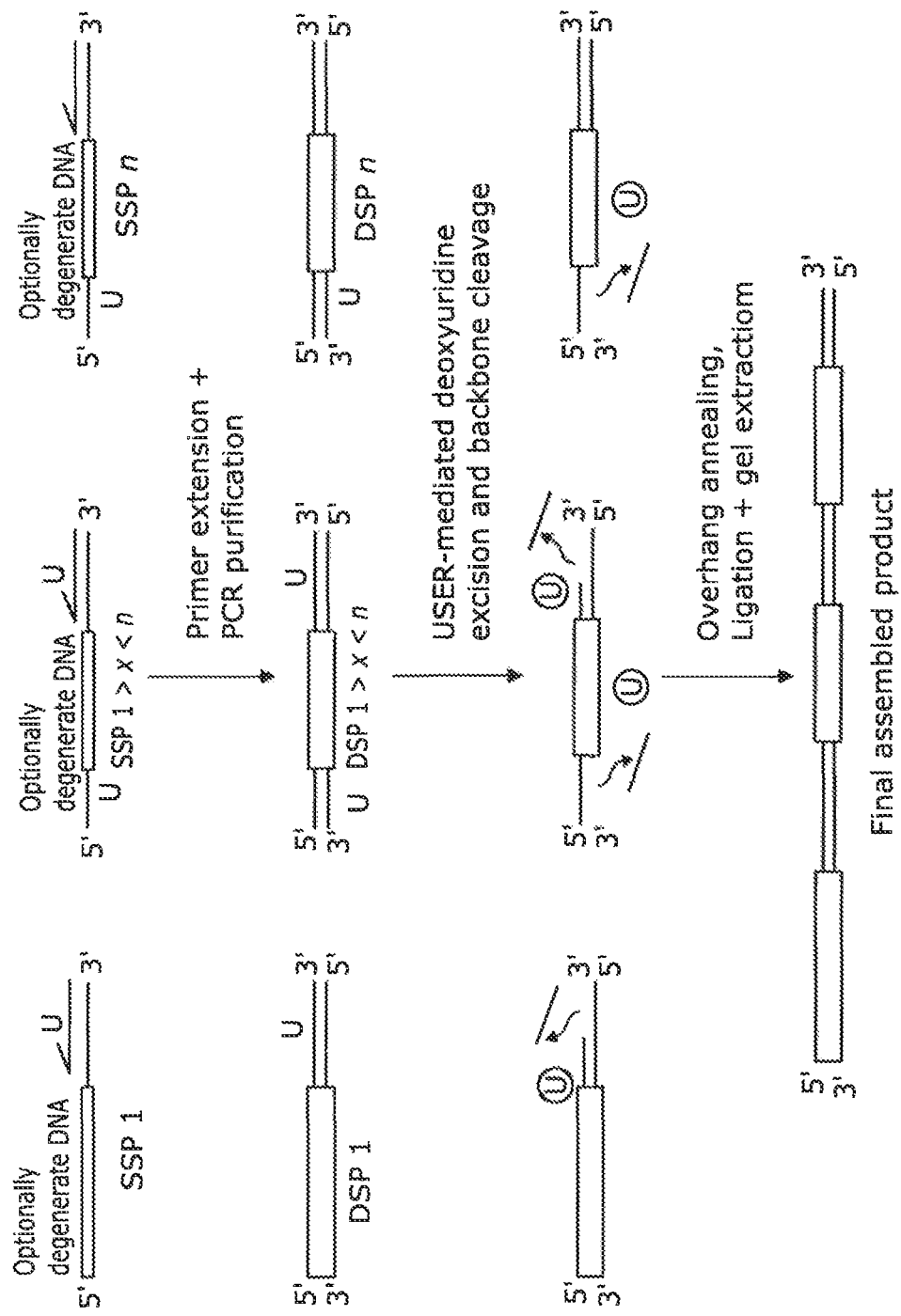
FIG. 11 is a schematic representation of an embodiment of a method of assembly of an n-part linear polynucleotide.

FIG. 11 shows an example of a method of assembly of an n-part linear polynucleotide, according to embodiments of the invention. In this embodiment, a first flanking DSP, a second flanking DSP and one intervening DSP are shown. The person skilled in the art would understand that the linear part (target sequence) may in fact comprise 2 or more intervening DSPs (DSP2 to DSPn−1) and corresponding single stranded polynucleotides (SSP2 to SSPn−1), wherein design, generation and assembly of the DSPs follows the same principles.

In particular, in the embodiment shown, a first flanking single stranded polynucleotide (SSP1), a second flanking SSP (SSPn) and at least one further single stranded polynucleotide (SSPx, where 1<x<n) are provided. Where the assembly reaction is intended for the creation of a DNA sequence library, any or all of these SSPs may comprise one or more sections of degenerate or randomized DNA sequence, depending on the type of library required.

A first primer (p1) that binds a terminus of the first flanking SSP (SSP1), a second primer (pn) that binds a terminus of SSPn, and a primer (px, where 1<x<n) for each SSPx, wherein each primer binds one extremity of an SSPx are then used to covert each SSP into its corresponding DSP by polymerase-mediated extension of primers p1, pn and px.

The first flanking DSP (DSP1) obtained above comprises a sequence CPS1 that is complementary to a polynucleotide sequence of the first intervening DSP (DSP2). The first intervening DSP (DSP2) comprises a second complementary polynucleotide sequence CPS2 that is complementary to CPS1 of DSP1. The first intervening DSP (DSP2) additionally comprises a third complementary polynucleotide sequence (CPS3) that is complementary to a polynucleotide sequence of the next intervening DSP (DSP3), or the second flanking DSP (DSPn), if a single intervening DSP is used. The next intervening DSP comprises a fourth complementary polynucleotide sequence (CPS4) that is complementary to CPS3. In embodiments where a single intervening DSP is used, the second flanking DSP (DSPn) comprises CPS4.

Overhangs are then created at one extremity of each flanking DSP, and at both extremities of each intervening DSP. The overhangs comprise at least a portion of the complementary polynucleotide sequences (CPS1-4). In the embodiment shown, overhangs are created by USER-mediated deoxyuridine excision. Therefore, primers p1 and px are provided with a uracil nucleotide for recognition by the USER enzymes. Additionally, each intervening SSP (SSPx) and the second flanking SSP (SSPn) comprise a uracil nucleotide at the terminus where the primer (px and pn, respectively) does not bind.

Because the overhangs contain complementary sequences CPS1-4, the overhangs can then be annealed, and the final assembled product ligated. Advantageously, the overhangs are designed such that the complementary sequences are present in a single part, and each pair of complementary sequences CPS1-CPS2, CPS3-CPS4, can be formed between a single pair of parts. Therefore, ordering and directionality of each of the first flanking, intervening and second flanking DSPs is determined by unique overhang pairing within the first to fourth complementary polynucleotide sequences (CPS1-4).

Figure 12:
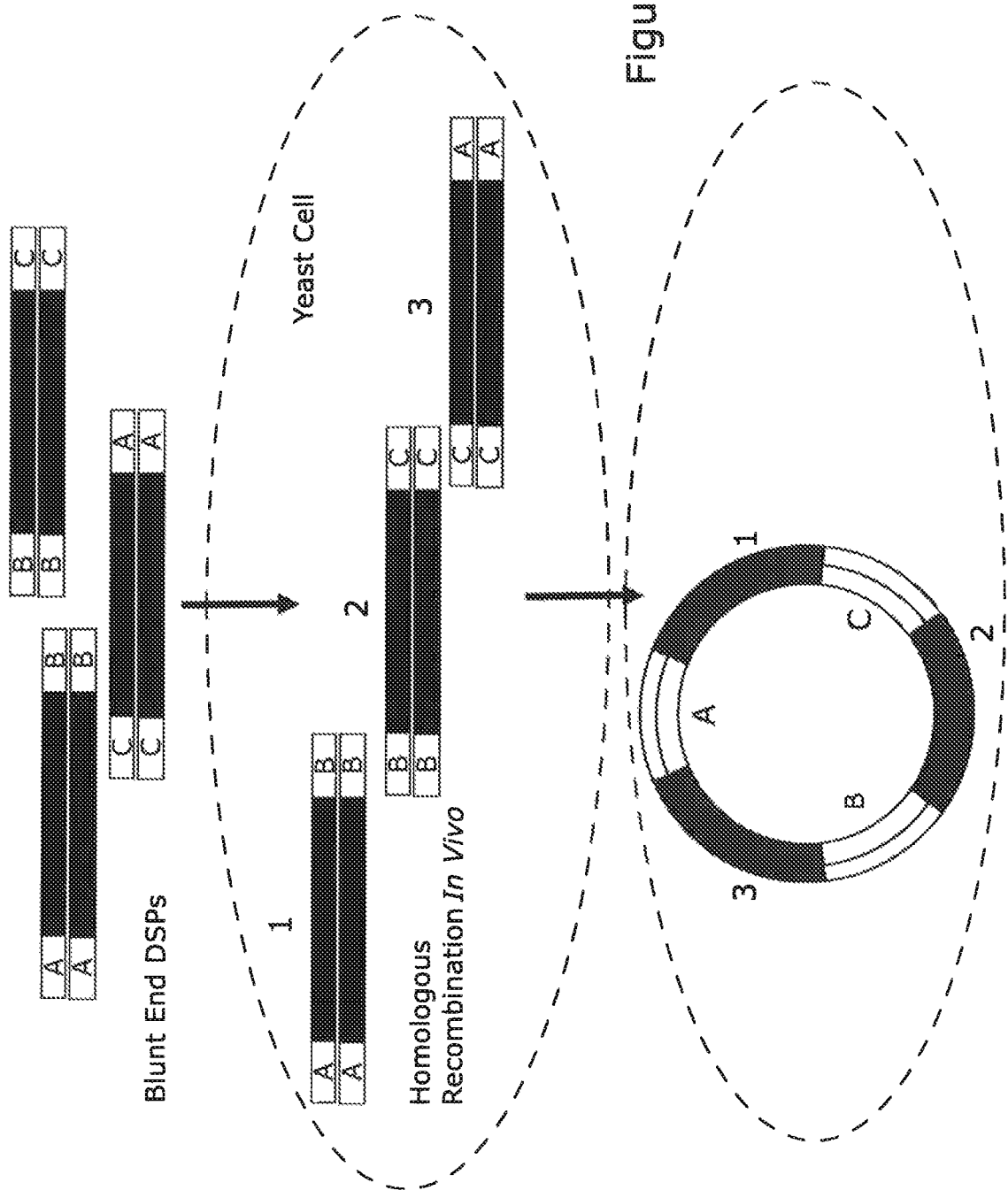
FIG. 12 is a schematic representation of in vivo homology mediated assembly.

In some embodiments, at least one DSP and optionally all DSPs generated in step (ii) are in a fully double stranded state and do not comprise 5' or 3' overhangs. In such embodiments, the complementary sequences are present in double stranded form. Such DSPs can be joined to other DSPs in the population and/or to non-population DSPs by homologous recombination. This is preferably carried out in vivo, for example in yeast. Homology mediated assembly in yeast, known as transformation associated recombination (TAR), is a technique for assembling linear double stranded polynucleotide fragments into circular plasmids in vivo in *Saccharomyces cerevisiae*. It relies on the transformation of ≥2 linear double stranded polynucleotide fragments, each with regions at both ends, complementary to the fragment it will be joined to. Once these fragments have been transformed into yeast, the yeast conducts homologous recombination to join all the fragments together. One embodiment is shown in FIG. 12. Here, three blunt end DSPs are assembled by homologous recombination in yeast to form a circularised target polynucleotide sequence. Regions containing the complementary sequences are shown as A, B, C, DSP fragments are labelled as 1, 2 and 3. DSP 1 contains complementary region B, which is shared by DSP 2. DSP 2 contains complementary region C which is shared by DSP 3. DSP 3 contains complementary region A which is shared by DSP 1. As with most cloning, one or more of the fragments inserted preferably contains a selection marker to allow successfully transformed and assembled plasmids to be isolated. Further details of the homologous recombination in yeast can be found in Kuijpers et al., *Microbial Cell Factories* 2013, 12:47.

Design of SSPs

The following steps may be used to design a set of SSPs and accompanying primers that can be used, in accordance with the polynucleotide assembly methodology described herein, to construct one or more target DSP sequences.

(1) Providing a target polynucleotide sequence that is to be assembled.

(2) Identifying a plurality of sequences in the target polynucleotide sequence, each of which could comprise a terminally-located inter-DSP overlap. The subsequences are termed 'complementary sequences'.

(3) Optionally filtering the plurality of complementary sequences using factors which may include
length of complementary sequences
whether the complementary sequences are unique within the population of complementary sequences;
whether the complementary sequences contain any degenerate bases;

(4) generating a plurality of complementary sequence combinations. As the total number of complementary sequence combinations is often very large, it may be preferable to reduce the number of complementary sequence identified in step (3) by increasing filter number/stringency.

(5) filtering the complementary sequence combinations to remove those that contain complementary sequence which overlap in the target polynucleotide sequence.

(6) using the filtered plurality of complementary sequence combinations to generate a plurality of DSP designs (7) evaluating the DSP designs using factors which may include:
  synthesis parameters (e.g. cost, turnaround time, scale, fidelity, ease of synthesis)
  ease and fidelity of SSP to DSP conversion (influenced by factors such composition of the primer binding site, secondary structure formation)

(8) evaluating the DSP-joining process using factors which may include:
  complementary sequence properties (e.g. interaction strength, likelihood to mis-anneal)
  complementary sequence orthogonality (e.g. estimated probability of two non-complementary overlaps mis-annealing)
  Number of DSP fragments required to make the target DSP (DSP number and final product yield may be inversely correlated)

(9) using multiparameter optimisation to select one or more candidate designs.

(10) for each candidate design, using multiparameter optimisation to determine how each DSP should be obtained

(11) providing an output report that comprises one or more sets of SSPs and the corresponding set of primers that are required to convert the SSPs into a population of DSPs that can be assembled into the target DSP sequence.

In one aspect, the invention provides a method of designing a plurality of SSPs that can be converted to DSPs for assembly into a target polynucleotide sequence. The method preferably comprises performing steps (1) to (11) above. One or more of these steps may be carried out by a computer. Preferably, all of steps (2) to (11) can be carried out by a computer.

The invention also provides a computer program for designing a plurality of SSPs for conversion into a plurality of DSPs for assembly into a target polynucleotide sequence, the program residing on a hardware computer readable storage medium and having a plurality of instructions which, when executed by a processor, cause the processor to perform operations comprising steps (2) to (11) above.

Terminal complementary sequences can be designed for compatibility with one or more DSP-joining techniques. For example, in the context of DSP-joining methods that do not involve the enzymatic processing of one or more recognition sites near the DSP termini (e.g. homologous recombination, exonuclease based assembly or Autosticky single primer extension), the complementary sequence can comprise any sequence that is a contiguous subsequence of the target polynucleotide sequence. In contrast, in the context of USER-based DSP joining methods, the complementary sequence can be derived from any contiguous subsequence of the target polynucleotide sequence provided that it has an 'A' at one end and a 'T' at the other. For a given target polynucleotide sequence, the total number of potential USER overlaps can be calculated by multiplying the number of A's in a given strand by the number of T's in the same strand. Using restriction enzymes, the complementary sequence is derived from a specific restriction enzyme recognition site where the restriction enzyme will bind the DNA and cut. In the context of Type IIS restriction enzymes, this recognition site can be removed during cleavage and so the complementary sequence can comprise any sequence that is a contiguous subsequence of the target polynucleotide sequence, provided that the appropriate cut site is programmed into the SSP such that it will be removed during enzyme cleavage.

For all of the aforementioned DSP-joining methods, as the length of a target polynucleotide sequence increases, the number of possible Overlaps increases non-linearly. It is theoretically possible to list all potential Overlaps for a given target polynucleotide sequence and DSP-joining method using deterministic approaches. This said, when the number of potential Overlaps is very large, the computational time required to complete this task may be prohibitively great. In instances such as this, it may be preferable to sample the total number of potential Overlaps for a given target polynucleotide sequence and DSP-joining method. Sampling may be achieved using either stochastic or deterministic approaches.

Applications

One of the application areas of this assembly methodology is the construction of highly degenerate DNA libraries. Libraries of diverse genetic sequences may be useful in identifying proteins with a specific function. For example, commercially valuable functional sequences may be identified by expressing a library of diverse nucleic acid sequences, testing the resultant proteins for a specific function, and isolating those sequences that perform well. Sequences may be further optimised for a particular function by repetitive cycles of diversification and selection. This process may be referred to as directed evolution. Sequences selected from diverse sequence pools may be useful in biological, medical, or industrial applications. For example, a sequence identified by directed evolution may be used in antibody engineering.

These libraries are relevant to a wide range of application areas. Once the libraries are created, they can be inserted into expression chassis (cell free or organisms such as *E. coli*, yeast, mammalian cells etc.) and screened (potentially via high throughput methodologies such as microfluidic cell sorting or phage display) for desired characteristics. It is then possible for an isogenic population of cells that exhibit the most optimal characteristics to then be selected, after which the inserted dsDNA from the library can be isolated and sequenced from each population.

Alternatively a number of isogenic populations of cells can have certain characteristics of interest quantified, these individual isogenic populations can then be isolated and sequenced. This will allow specific sequences from the library to be associated with quantifications of the characteristics of interest (performance data). This dataset can then be used to computationally predict the performance of sequences for which performance data does not exist. This can be done by employing machine learning techniques such as linear or logistic regression, neural networks etc.

Protein expression and folding can be optimised by creating constructs containing libraries of regulatory elements (such as promoters, RBSs, enhancer elements etc). The large amounts of degeneracy that can be built into the libraries mean that a very large potential sequence space can be sampled. The method of the present invention facilitates the generation of libraries that are orders of magnitude greater diversity than pre-existing equivalents.

These libraries would also be highly valuable in a protein engineering context, where the library could contain variants that encode different amino acid sequences. Creating such large libraries as is not technically possible using existing methods of gene synthesis, but is made possible using the method of the invention. Such high levels of variability are desirable in fields such as antibody engineering where changing the amino acid sequence slightly can alter the antibody binding affinity, and therefore its effectiveness.

While any IUPAC sequence can be designed computationally, existing experimental techniques only allow a subset of these to be made where the total number and positions of degenerate bases is severely limited. The method of the present invention allows longer and more degenerate library designs to be made. This represents a significant improvement on current state of the art in terms of levels variability and the amount of control over that variability within physical dsDNA libraries. These libraries can be created for any genetic element, or combination of elements and can be created in either linear or circular format.

Another application area for the method of the invention is in the construction of polynucleotide sequences that contain repetitive motifs (e.g. polynucleotide sequences encoding protein-based block copolymers). In nature, protein-based block copolymers exhibit outstanding physical properties. One such example is spider silk, which has a tensile strength similar to that of steel, while also being able to stretch to up to 5 times its own length. Another example is mussel foot protein, which acts as a strong and water-insoluble adhesive. Existing methods are not suited to the construction of polynucleotide sequences that contain repetitive motifs. In contrast, polynucleotide sequences which are difficult to assemble using traditional methods can easily be assembled using the methods disclosed herein. Correspondingly, the method of the invention could be used to efficiently engineer protein-based block copolymers.

Proteins that contain a lot of repetitive motifs often have highly repetitive DNA sequences particularly due to host organism codon usage bias. The presence of these repetitive motifs in the coding DNA makes these genes difficult to assemble using existing methods due to high levels of intra-sequence homology. In the method of the present invention, these repetitive motifs are positioned within a double stranded polynucleotide format and are therefore not able to interfere with the DSP assembly process. Moreover, repetitive motifs can be first divided into separate SSPs during the design of the SSPs. The SSPs are converted to DSPs which are then assembled at unique overlap regions to form the target polynucleotide sequence comprising the repetitive motifs.

In another application of the method of the invention, target polynucleotide sequences generated using this approach can be applied to CRISPR-Cas9 system, particularly in the field of genome editing. Cas9, or any variant thereof, (e.g. Cas9D10A) are prokaryotic proteins that form breaks in DNA at very specific locations. They do this in conjunction with two RNA molecules (crRNA and trancrRNA), which can be synthetically combined into a synthetic guide RNA (sgRNA). This guide RNA contains a 20 nucleotide sequence that is complementary to the destination DNA sequence that is to be edited. Upon expression of these two components, the Cas9 protein complexes with the sgRNA and locates to the destination DNA, at which point Cas9 cleaves the DNA. If a donor template is supplied with homologous regions either side of this break, the break will be repaired using the Homology-Directed Repair Pathway, introducing the donor DNA into the genome. Alternatively, if no donor template is supplied and both strands have been cleaved (eg. by wildtype Cas9), the damaged DNA will be repaired by the Non-Homologous End Joining pathway, resulting in deletions or insertions at the destination DNA. More information on the CRISPR-Cas9 system can be found Jinek, M., et al. A programmable dual-RNA-guided DNA endonuclease in adaptive bacterial immunity. (2012) Science, 337, 816-821 and Cong L., et al. Multiplex genome engineering using CRISPR/Cas system (2013) Science, 339, 819-823.

When designing such genome editing systems, both the donor DNA and/or the sgRNA could be generated using this invention, with these target polynucleotide sequences optionally comprising degenerate DNA. By creating a degenerate library of the donor DNA and transforming them into host cells, along with the rest of the CRISPR-Cas9 system, the incorporation of many different DSPs into the genomes of different cells concurrently would be possible. The performance of these transformed libraries could then be screened, clones with desired characteristics isolated, and their DNA sequenced.

Preferred features of each aspect of the invention are as for each of the other aspects mutatis mutandis. The prior art documents mentioned herein are incorporated to the fullest extent permitted by law.

The invention will now be further described by way of reference to the following Examples which are provided for the purposes of illustration only and are not to be construed as limiting on the invention.

Example 1: Conversion of ssDNA to dsDNA Using Single Step Polymerase Extension

Overview

In this experiment, it is demonstrated that a degenerate ssDNA oligonucleotide can be efficiently converted to dsDNA using single primer polymerase extension. Conventionally, thermostable polymerase extension is used in the polymerase chain reaction (PCR) to amplify dsDNA, using two primers—one annealing to the plus-sense DNA strand, the other to the minus-strand. However, in this case, in order to avoid introducing any bias into a degenerate DNA library through amplification, a single primer that anneals to the 3' end of a constant region of a synthetic degenerate SSP library was used. A single polymerase extension then efficiently converts the ssDNA to dsDNA to allow further assembly.

Methods

Single Step Polymerase Extension Reaction

The following reaction was prepared in a PCR tube:

| Reagent | Amount |
| --- | --- |
| 10X PfuTurbo Cx Reaction Buffer | 5 µl |
| 10 mM dNTPs | 1 µl |
| 10 µM Primer | 2.5 µl |
| Single-stranded synthetic template DNA | 100 ng |
| DMSO | 1.5 µl |
| Double distilled water | up to 50 µl |
| PfuTurbo Cx Polymerase | 1 µl |

The reaction was transferred to thermocycler and run with the following conditions:

| Step | Temperature (° C.) | Time |
| --- | --- | --- |
| Denaturation | 95 | 2.5 minutes |
| Primer Annealing | 53 | 30 seconds |
| Polymerase extension | 72 | 11 minutes |
| Store | 4 | Infinite |

Quantification of dsDNA Using Quanti-iT Picogreen

The amounts of dsDNA generated during the single polymerase extension was quantified according to the manufacturers instructions of the Quant-iT PicoGreen dsDNA Reagent and Kit (Invitrogen).

Results

Validation of ssDNA—dsDNA Conversion

Figure 13:
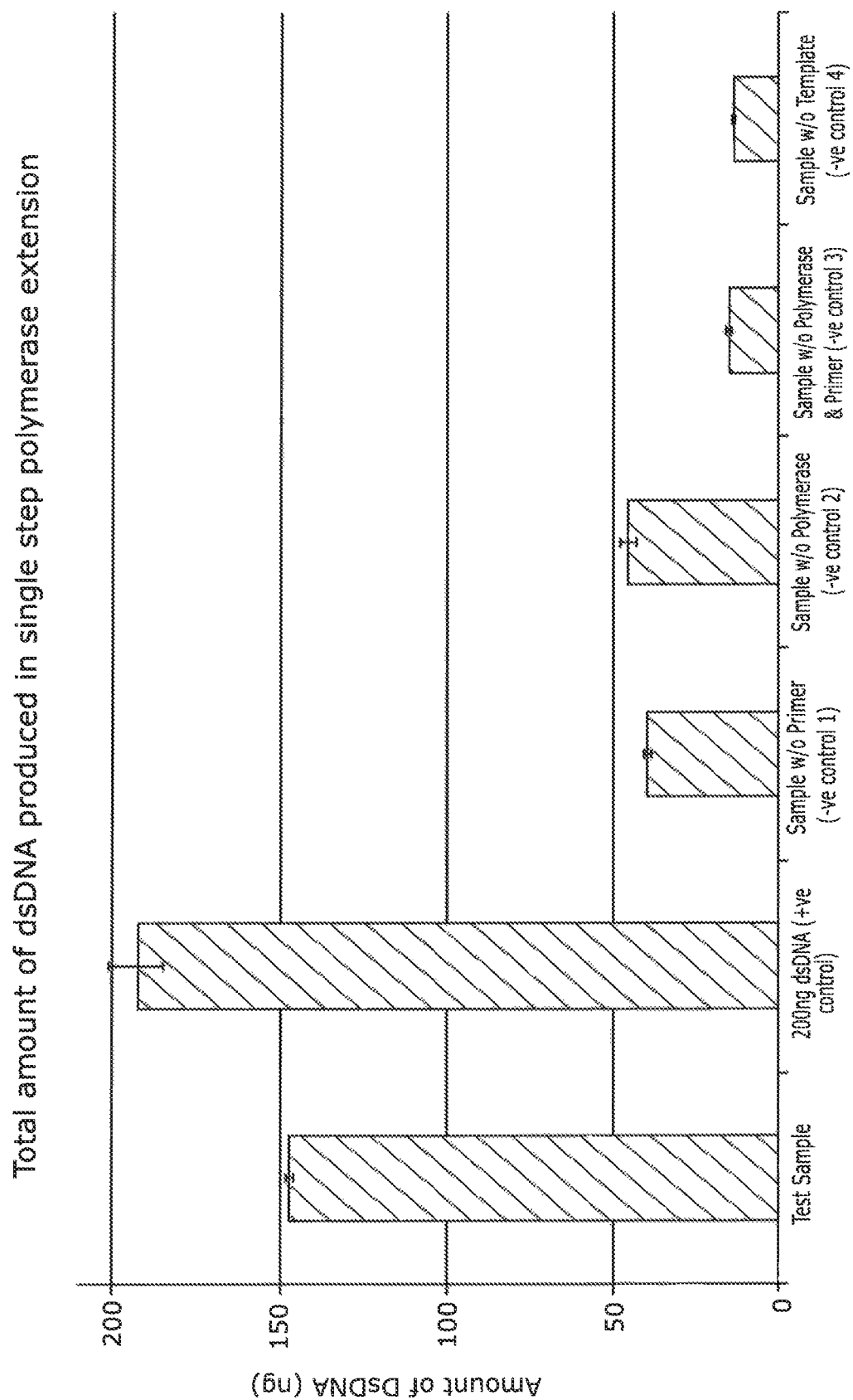
FIG. 13 shows the yields of a polymerase extension reaction used to generate DSPs from an SSP template.

Initially, validation of this single primer polymerase extension method was obtained by annealing a primer to a 200 bp SSP and extending with Pfu Cx polymerase using one reaction condition with several controls. The amount of DSP produced from this reaction was quantified using Quanti-iT Picogreen reagent. All negative controls contained the same reagents and were exposed to the same conditions as the sample except for those stated. The 200 ng dsDNA in the positive control was diluted in water to a total volume of 50 µl before being quantified. The results are summarised in FIG. 13. After accounting for the background dsDNA signal from hybridisation of the primers and secondary structure of the SSP template, illustrated by the negative control lacking the polymerase, the results show that 101.6 ng of DSP product was produced from 100 ng of SSP template. After accounting for the fact that ssDNA has half the molecular weight of dsDNA, the efficiency of the reaction was calculated to be 50.8%.

Optimisation of Single Step Polymerase Extension

Figure 14:
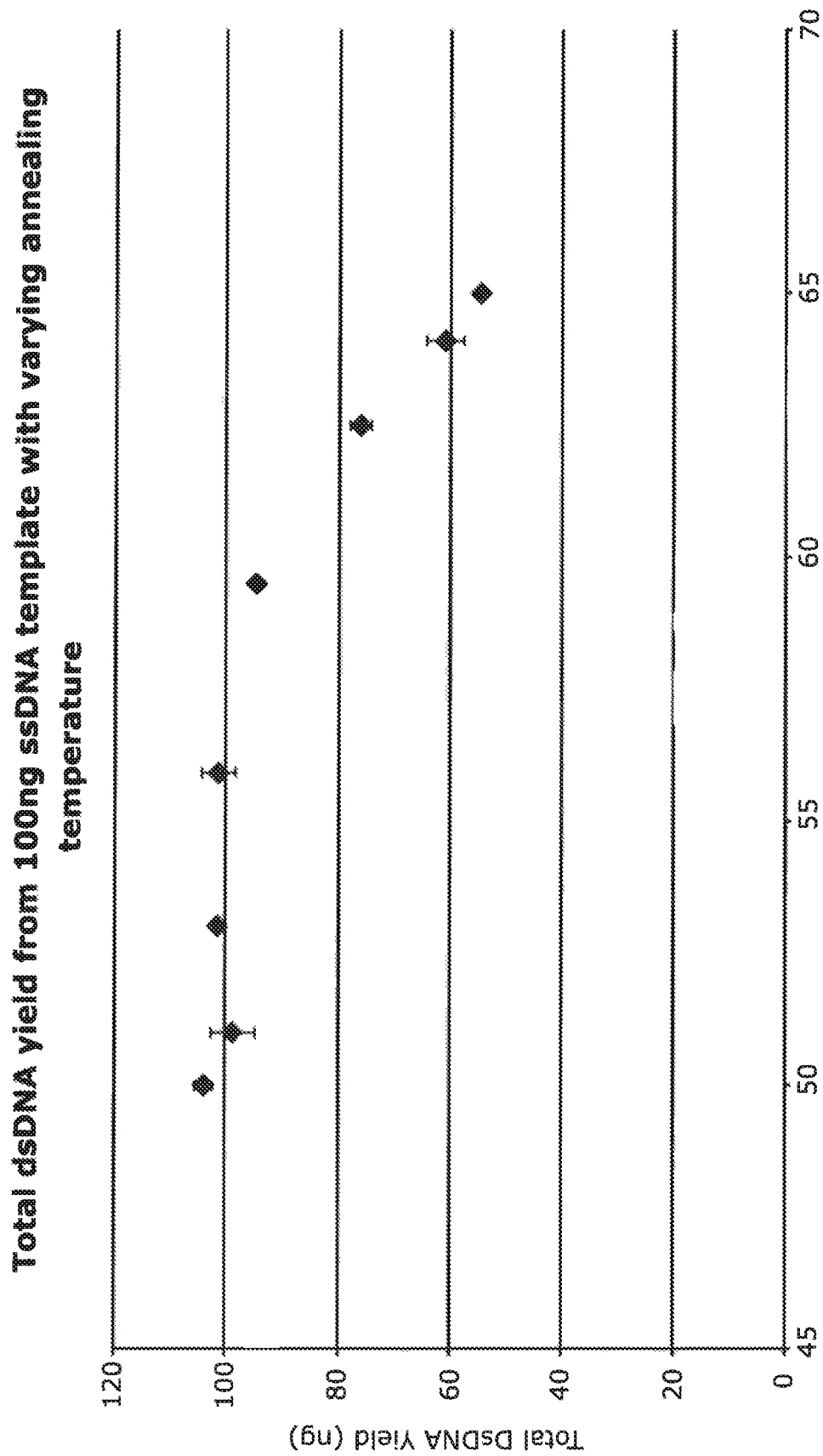
FIG. 14 shows the results of an experiment to determine the optimum annealing temperature for a primer.

In addition to this basic validation of the technique, optimisation of the process was sought through varying the annealing temperature of the primer. Here a gradient of annealing temperatures (50-65° C.) was used simultaneously and the effect of this on the DSP yield was tested. The results of this are shown in FIG. 14. As would be expected, the amount of DSP product drops off as higher annealing temperatures are used since less primer anneals to the template DNA. For future single primer polymerase extensions with different template/primer combinations, this experiment would be run initially in order to find the highest possible annealing temperature before yields are negatively affected (in this case 55.9° C.). This minimises the effect of nonspecific primer annealing (giving incorrect product), while maximising DSP yield.

Summary

This example demonstrates that degenerate SSP templates with a constant binding region can be efficiently converted to DSPs. A gradient of temperatures can be used to evaluate the optimum annealing temperature for maximising yield and minimising non-specific product for each template/primer combination on a case-by-case basis.

Example 2—Directional Library Insertion

Overview

An experiment was devised to demonstrate the directional insertion of a 150 base pair polynucleotide library into a vector using USER cloning. In this example, USER cloning relies on the introduction of a uracil base at either end of double stranded inserts and vectors. These uracil sites and DNA that is located to the 5' end of this site are removed by the USER enzymes, exposing an overhang. The overhangs allow specific annealing of the insert to vector and therefore assembly of the desired construct.

Computational Sequence Design

Purpose-built algorithms were used to design both SSPs and the primers required for the conversion into DSPs. The SSP designs ultimately enable the DSPs to be assembled in a defined order to yield the user's target polynucleotide sequence. The precise algorithm used depends on the user's preferred experimental methodology and DSP termini. The following is a description of one such algorithm which can be used for a directional USER-based two-part assembly reaction in which one part is a degenerate library and the second part is a vector.

Algorithm Name: LabGene150( )

Algorithm Inputs:

| INPUT | DESCRIPTION |
|---|---|
| 'insertion.site' | A numeric value describing the exact site for library insertion. The numeric value corresponds to the number of nucleotide bases in object 'Vector.template' that precede the target insertion site. |
| 'insert.template' | Name of a file (in .fasta format) containing the degenerate sequence that is to be inserted into the vector. |
| 'vector.template' | Name of a file (in .fasta format) containing the vector sequence. |
| 'USER.overhang' | This sets the target length of the 'sticky ends' for USER cloning. This is typically set to 9 nucleotides. Additional parameters are added to specify maximum and minimum acceptable overhang lengths. For this a range of 5 nucleotides (minimum) and 11 nucleotides (maximum) are used. |
| 'tm' | The target melting temperature for homologous regions of primers. This is typically set to 64 degrees centigrade. |
| 'insert.directory' | File location of 'insert.template' |
| 'vector.directory' | File location of 'vector.template' |
| 'base.directory' | File location for required custom sub-functions. |
| 'synthesis.range' | This is a numeric value that describes how the maximum length of the SSP. In this instance, it is set to 200 nucleotides. This is used to determine how long the vector-derived flanking regions on either side of the degenerate insert can be. This is typically set parameter to 20-25 to ensure specific primer annealing. |

Algorithm Outputs:

| OUTPUTS | DESCRIPTION |
|---|---|
| Insert design | A modified version of 'insert.template' for which additional 5' and 3' polynucleotide sequences have been attached. These regions enable conversion of SSP to DSP and subsequent terminal processing. |
| Vector primers | Designs for two primers for preparation of the vector for library insertion via USER cloning. |
| Insert primer | A single primer that enables the conversion of the library insert from SSP to DSP from. The final product is also compatible with terminal processing using USER enzymes. |

Algorithm Workflow

Figure 15A:
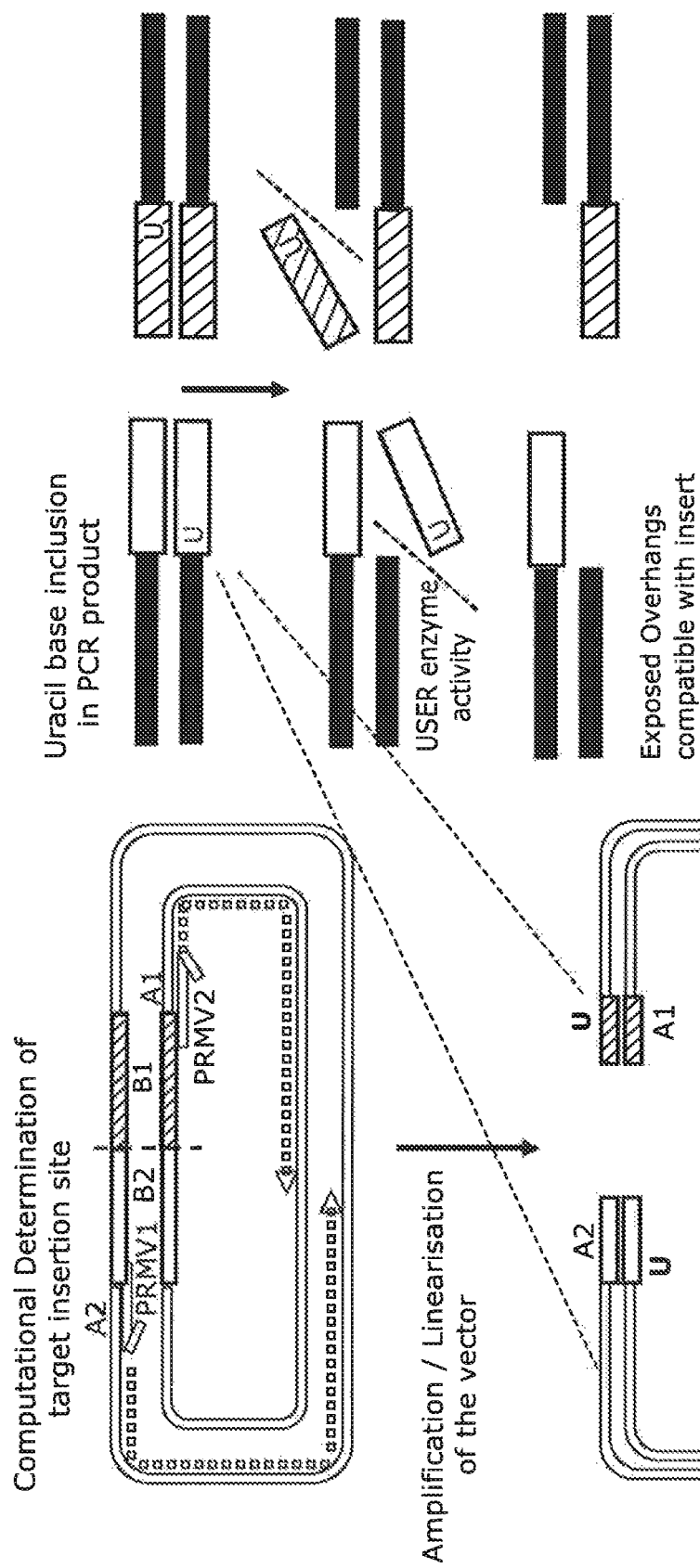
FIGS. 15A, 15B and 15C show an example of how a DSP library can be inserted into a vector with USER cloning.

STEP 1: VECTOR DESIGN (this is described with reference to FIG. 15A)

1. The site for fragment insertion site is specified by the user.
2. The vector sequence is analysed by computationally scanning regions upstream and downstream of the target insertion site for suitable USER overhangs (A1 & A2). The regions between the overhangs and the insertion site are termed B1 & B2.

-continued

3. Primers (PRMV1 and PRMV2) are designed for vector amplification via PCR. These two primers anneal to A1 and A2 respectively.
4. The primers are designed such that following linearisation of the vector by PCR, the PCR product contains uracils (Us) at the appropriate sites in the USER overhang.
5. These uracils can be cleaved by USER enzymes to create insert specific overhangs.

Figure 15B:
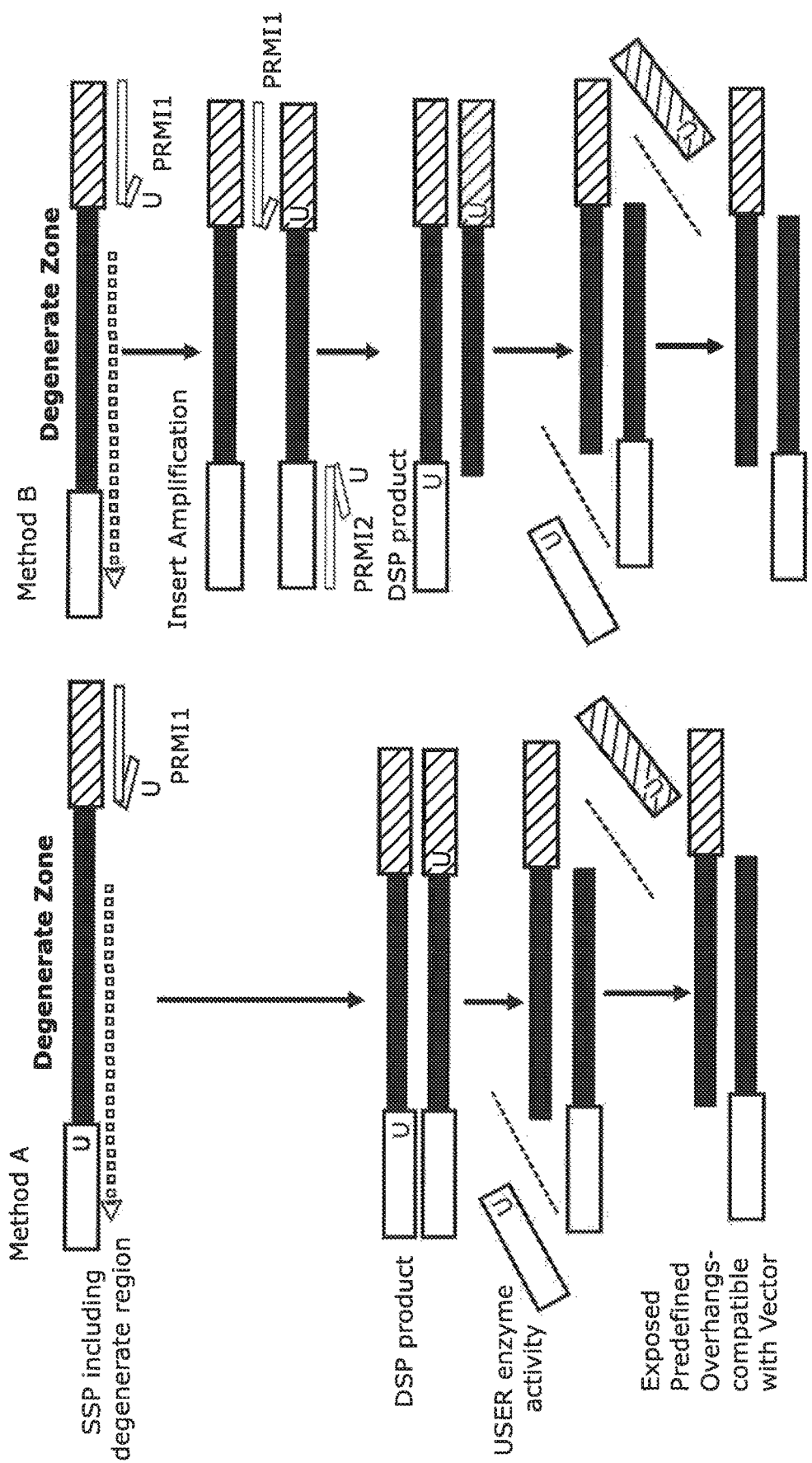

STEP 2: INSERT DESIGN (this is described with reference to FIG. 15B)

1. The user enters the sequence for the degenerate region that they want to insert into the vector.
2. The algorithm adds on vector-derived flanking sites containing the USER overhangs. These flanking sites have been designed so that they are sufficiently long for specific primer annealing.
METHOD VARIANT A - One of the flanking sites contains a uracil in the SSP design. The second uracil is built into PRMI1 which means that it will be added during the SSP -> DSP conversion process.
METHOD VARIANT B - If the user wants to perform an insert amplification reaction, then a second uracil can be incorporated into PRMI2. In this instance, a uracil can still be incorporated into the initial template sequence but this is not mandatory.
1. The DSP product contains uracil residues on both strands. At a given end, the uracils will occur in either the top or bottom strand but not both.
2. Following cleavage by the USER enzyme, the DSP is ready to insert into the vector.

Figure 15C:
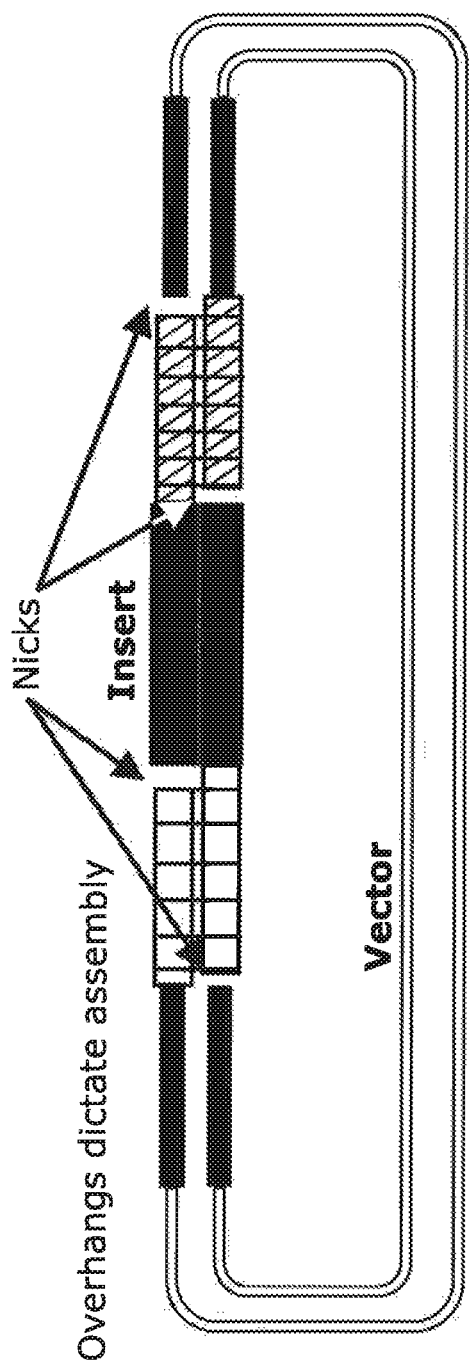
Figure 16A:
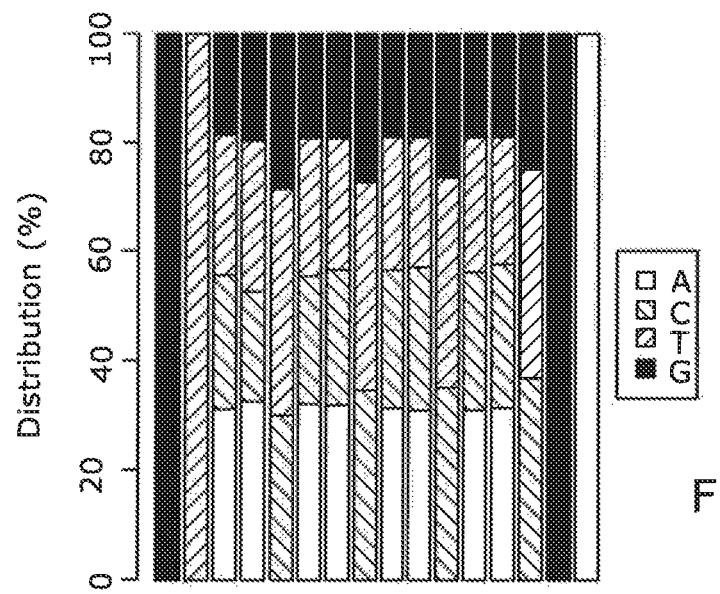
FIGS. 16a and 16b show the results of an experiment to determine the base distribution in degenerate portions of target sequences obtained from a library generation process according to embodiments of the invention.
Figure 16B:
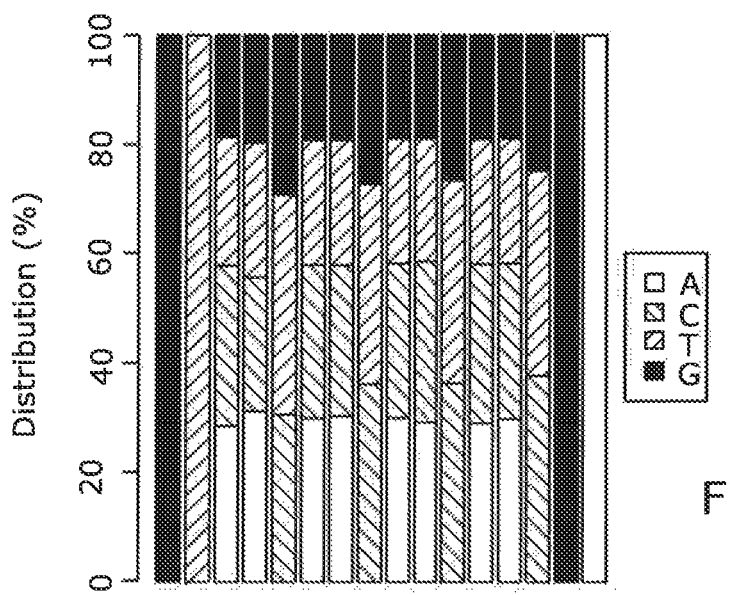

STEP 3: ASSEMBLY (this is described with reference to FIG. 15C)

1. The overhangs dictate the assembly process.
2. The final product represents the vector with the degenerate zone inserted into the target site.

Wet Lab Assembly
The following experimental steps were used.
1. POLYNUCLEOTIDE PROCUREMENT:
    The algorithm-designed SSP and primers were purchased from a commercial supplier (Integrated DNA Technologies, Inc).
2. SSP->DSP CONVERSION:
    The SSP was converted into a DSP using method variant 2B (see above). This reaction involved the use of PfuCx Turbo Polymerase. This polymerase was used because it has high fidelity and also can read-through uracil bases. The DSP product was gel-purified and quantified.
3. VECTOR PREPARATION:
    The vector backbone was linearised using PCR. This reaction involved the use of uracil containing primers and PfuCx Turbo Polymerase. The PCR product was gel-purified and quantified.
4. DNA ASSEMBLY:
    a. The assembly reaction was carried out as follows:
    b. 200 ng of DSP was mixed with 150 ng of vector in a 25 μl reaction with 1× restriction enzyme (Cut-Smart) buffer and 1 unit of USER enzyme mix (NEB). The reaction mix was incubated in a thermocycler at 37° C. for 20 minutes then 25° C. for 20 minutes.
    c. The entire reaction was transferred to 50 μl chemo-competent BL21 T7 express *E. coli* and transformed and plated on LB agar (containing chloramphenicol as a selection agent).
5. VERIFICATION:
    8 colonies were randomly picked, grown up overnight in LB media, mini-prepped and sequenced. The results of this are summarised below.

| Colony | Cloning junction | Insert fidelity |
|---|---|---|
| A | Correct | 200/200 (100%) |
| B | Correct | 199/200 (99.5%) (1× substitution) |
| C | Correct | 200/200 (100%) |
| D | Correct | 200/200 (100%) |
| E | Correct | 200/200 (100%) |
| F | Correct | x1 deletion (1bp), x1 substitution |
| G | Correct | 200/200 (100%) |
| H | Correct | 200/200 (100%) |

It is important to note, that each of the sequenced inserts were unique. These insert sequences are shown below:

| Colony | Insert Sequence (DNA) |
|---|---|
| A | ATGTCTCCTATTCTGGGATATTGGAAGATCAAAGGCCTTGTG CAGCCCACCCGTCTTCTTCTGGAGTATCTCGAAGAGAAATAT GAGGAACACCTATACGAGCGCGATGAAGGTGATAAATGGCGG AACAAGAAGTTTGAGCTCGGGCTA (SEQ ID NO: 2) |
| B | ATGTCGCCAATTCTAGGTTATTGGAAGATCAAAGGTCTGGTA CAACCTACTCGTCTGCTTCTTGAATACCTGTAAGAAAAGTAC GAGGAACATCTTTATGAACGCGATGAAGGGGACAAGTGGCGA AATAAGAAGTTTGAACTCGGTCTT (SEQ ID NO: 3) |
| C | ATGTCGCCAATCCTGGGGTATTGGAAGATAAAAGGCCTTGTC CAGCCCACGCGACTACTACTCGAATACCTGGAGGAGAAATAT GAAGAACACCTTTACGAGCGTGATGAAGGTGACAAGTGGCGT AACAAGAAATTTGAGCTTGGGCTA (SEQ ID NO: 4) |
| D | ATGTCTCCAATACTGGGATATTGGAAAATAAAAGGGCCTGTT CAACCAACCCGCCTACTTCTGGAATATCTGGAAGAGAAGTAT GAAGAGCATCTTTATGAACGGGATGAGGGTGACAAATGGCGT AATAAGAAGTTTGAACTTGGTCTT (SEQ ID NO: 5) |
| E | ATGTCACCAATACTCGGGTACTGGAAAATTAAAGGCCTCGTA CAGCCTACCCGACTGCTTCTAGAGTACCTTGAAGAAAAGTAT GAAGAGCATCTTTATGAGCGTGATGAGGGGGACAAATGGCGA AATAAAAAGTTTGAGCTTGGGCTG (SEQ ID NO: 6) |
| F | ATGTCTCCTTACTTGGATACTGGAAGATTAAGGGACTCGTTC AACCTACGCGTCTTCTGCTCGAGTATCTCGAGGAGAAATACG AAGAACATCTCTATGAACGGGACGAGGGCGATAAATGGCGCA ACAAGAAGTTTGAACTGGGGCTG (SEQ ID NO: 7) |
| G | ATGTCCCCGATCCTCGGCTACTGGAAAATTAAGGGGCTCGTT CAGCCTACCCGTCTGCTACTCGAATACCTGGAAGAAAAATAT GAGGAACATCTATATGAACGCGACGAAGGGGACAAGTGGCGA AATAAGAAGTTCGAACTAGGGCTG (SEQ ID NO: 8) |

| Colony | Insert Sequence (DNA) |
|---|---|
| H | ATGTCTCCTATTCTCGGGTATTGGAAGATCAAAGGGCTGGTC CAGCCTACTCGGCTACTTCTGGAATATCTTGAGGAAAAATAT GAGGAACACCTGTATGAACGTGACGAAGGAGATAAGTGGCGT AACAAGAAATTCGAGCTGGGCCTA (SEQ ID NO: 9) |

The degenerate library was designed to test the effect that different DNA sequences (encoding the same protein sequence) could have on gene expression. The table below shows the translated products of the 8 DNA libraries. Apart from the two colonies that contained errors (Colony B and Colony F) all the other colonies contained an insert that encoded the correct protein sequence (MSPILGYWKIK-GLVQPTRLLLEYLEEKYEEHLYERDEGDKWRNK-KFELGL SEQ ID_NO:10).

| Colony | Insert Sequence (Protein) |
|---|---|
| A | MSPILGYWKIKGLVQPIRLLLEYLEEKYEEHLYERDEGDKW RNKKFELGL (SEQ ID NO: 10) |
| B | MSPILGYWKIKGLVQPTRLLLEYL* (SEQ ID NO: 11) |
| C | MSPILGYWKIKGLVQPIRLLLEYLEEKYEEHLYERDEGDKW RNKKFELGL (SEQ ID NO: 10) |
| D | MSPILGYWKIKGLVQPIRLLLEYLEEKYEEHLYERDEGDKW RNKKFELGL (SEQ ID NO: 10) |
| E | MSPILGYWKIKGLVQPIRLLLEYLEEKYEEHLYERDEGDKW RNKKFELGL (SEQ ID NO: 10) |
| F | MSPYLDTGRLRDSFNLRVFCSSISRRNIKNISMNGTRAING AIRSLNWGX (SEQ ID NO: 12) |
| G | MSPILGYWKIKGLVQPIRLLLEYLEEKYEEHLYERDEGDKW RNKKFELGL (SEQ ID NO: 10) |
| H | MSPILGYWKIKGLVQPIRLLLEYLEEKYEEHLYERDEGDKW RNKKFELGL (SEQ ID NO: 10) |

Summary

This experiment demonstrates that the degenerate regions of up to 150 bases can be directionally-cloned into a vector using USER cloning.

Example 3 (In-Silico)—Design of Single Stranded Polynucleotides for the Assembly of Mussel Foot Protein In this example, single stranded polynucleotides for the assembly of a target sequence encoding mussel foot protein were designed. The target sequence is shown below:

| Target Sequence (first 2000 bases from GenBank AY960601.1 SEQ ID_NO: 13) |
|---|
| ATGGAGGGAATCAAATTAAATCTGTGCCTCCTGTGCATATTTTCTTGTGA CGTCTTTGCTCTTTCAAATGGTTTCATACACAACGCATATGGCTCAGCTT |

| Target Sequence (first 2000 bases from GenBank AY960601.1 SEQ ID_NO: 13) |
|---|
| ATGCAGGTGCAAGCGCTGGGGCTTACAAGCCATTACCCGGTTCATACGGA TCAAAGCATGTACCAGTATATAAACCTATGAATAAGATTCCAACATCATA TATATCCAAGAAAAGTTATCCGGCACCCTATAAACCGAAAGGCTATCATC CTACGAATAGTTATCAGCCAACATATGGATCAAAGACAAACTATCCGCCA ATATATAAGCCAGTTGCAAAGAAGCTATCATCATACAAAGCTATTAAGAC AACGTATCTGGTCTATAAAGCAAAGACAAGTTATCCACCAGTTTATAAAC ATAAGATAACTAATCCTCCAACATATAAACCTAAGATTACTTATCCCCCA ACATATAAACCAAAGCCAAGTTATCCTCCAACATATAAACCAAAGCCAAG TTATCCTCCAACATATAAAGCAAAGAAAACTTATCCTTCAACATATAAAC CAAAGCCAAGTTATCCTCCAACATATAAACCTAAGATAACTTATCCTCCA ACATATAAACCAAAGCCAAGTTATCCGCCTTCATATAAGGCAAAGAAATC ATATCCTTCAACATATAAACCAAAGCCAAGTTATCCTCCAACATATAAAG CAAAGAAAACTTATCCTTCAACATATAAACCAAAGCCAAGTTATCCTCCA ACATATAAACCTAAGATAACTTATCCTCCAACATATAAACCAAAGCCAAG TTATCCGCCTTCATATAAGGCAAAGAAATCATATCCTTCAACATATAAAC CAAAGCCAAGTTATCCTCCTACATATAAACCTAAGATAACTTATCCTCCA ACATATAAACCAAAGCCAAGTTATCCTCCAACATATAAAGCAAAGAAAAC TTATCCTCCAACATATAAACCTAAGATAACTTATCCTCCAACATATAAAC CAAAGCCAAGTTATCCCACTTCATATAAATCTAAGAAAACTTATCCTCCA ACATATAAACCTAAAATAACTTATCCACCAACATATAAACCAAAGCCAAG TTATCCACCATCATATAAACCTAAGATTACTTATCCTCCAACTTATAAAC CTAAGAAAAGTTATCCTCCAGCATACAAATCTAAGGCAAGTTATCCCCCT TCTTATCAACCCAAGAAAACTTATCTGCCATCATATAAACCTAAGAAAAC TTATCCTCCAACATATAAACGTAAGATAAGTTATCCACCAACGTATAAAA CAAAGCCAAGTTATCCATCATCTTATAAACGTAAAACAAGTTATCCATCA ACATATAAACGTAAGACTAGTTATCCTCCAACATATAAACCTAAGATAAG TTATCCTTCAACTTATAAAACAAAGCCAAGTTATCCACCAACGTATAAAG CAAAGAAAACTTATCCTCCAACATATAAACCTAAGATAACTTATCCTCCA ACATATAAACCAAAGCCAAGTTATCCCACTTCATATAAATCTAAGAAAAC TTATCCTCCAACATATAAACCTAAAATAACTTATCCACCAACATATAAAC CAAAGCCAAGTTATCCACCATCATATAAACCTAAGATTACTTATCCTCCA ACTTATAAACCTAAGAAAAGTTATCCTCCAGCATACAAATCTAAGGCAAG TTATCCCCCTTCTTATCAACCCAAGAAAACTTATCTGCCATCATATAAAC CTAAGAAAACTTATCCTCCAACATATAAACGTAAGATAAGTTATCCACCA ACGTATAAAACAAAGCCAAGTTATCCAGCATCTTATAAACGTAAAACAAG TTATCCATCAACATATAAACGTAAGACAAGTTATCCTCCAACATATAAAC CTAAGATAAGTTATCCTTCAACTTATAAAACAAAGCCAAGTTATCCACCA ACGTATAAACCAAAACCAAGTTATGCATCATCATATAAACCTAAGATACG |

USER Based Assembly:

To make the Target Sequence using the DNA assembly technique disclosed herein in the context of USER assembly, the following process can be used.

Step 1: Fragmentation of the Target Sequence

In the first step, the Target Sequence is fragmented into several SSP designs. Each of these SSP fragments is 60-200 bases in length. SSP fragment length impacts on the following variables:

Synthesis cost (per base).

Synthesis fidelity (due to coupling efficiency).

Likelihood of reaction being successful (by reducing the need for a higher number of SSPs to cover the complete target sequence, assembly efficiency can be maximised).

Each fragment represents a continuous portion of the target sequence. The target sequence is fragmented such that unique regions of homology are generated at each inter-fragment junction. Fragments are designed such that a reverse primer can bind specifically to its 3' region (allowing efficient conversion to a double stranded fragment) and contain a uracil base to allow downstream USER assembly.

| Primer (5' to 3') | ssDNA Fragment (5' to 3') |
|---|---|
| >PRM_F1 ATGAUGTTGGA ATCTTATTCAT AGG (SEQ ID_NO: 14) | >F1 ATGGAGGGAATCAAATTAAATCTGTGCCTCCTGTGCATATTTTCTTGTGACGTCTTTGCTC TTTCAAATGGTTTCATACACAACGCATATGGCTCAGCTTATGCAGGTGCAAGCGCTGGGGC TTACAAGCCATTACCCGGTTCATACGGATCAAAGCATGTACCAGTATATAAACCTATGAAT AAGATTCCAACaTCAT (SEQ ID_NO: 15) |

| Primer (5' to 3') | ssDNA Fragment (5' to 3') |
|---|---|
| >PRM_F2<br>AAACUGGTGGA<br>TAACTTGTCTT<br>TGC (SEQ<br>ID_NO: 16) | >F2<br>ATCAUATATATCCAAGAAAAGTTATCCGGCACCCTATAAACCGAAAGGCTATCATCCTACG<br>AATAGTTATCAGCCAACATATGGATCAAAGACAAACTATCCGCCAATATATAAGCCAGTTG<br>CAAAGAAGCTATCATCATACAAAGCTATTAAGACAACGTATCTGGTCTATAAAGCAAAGAC<br>AAGTTATCCACCaGTTT (SEQ ID_NO: 17) |
| >PRM_F3<br>ATCTUAGGTTT<br>ATATGTTGGAG<br>GATAAC (SEQ<br>ID_NO: 18) | >F3<br>AGTTUATAAACATAAGATAACTAATCCTCCAACATATAAACCTAAGATTACTTATCCCCCA<br>ACATATAAACCAAAGCCAAGTTATCCTCCAACATATAAACCAAAGCCAAGTTATCCTCCAA<br>CATATAAAGCAAAGAAAACTTATCCTTCAACATATAAACCAAAGCCAAGTTATCCTCCAAC<br>ATATAAACCTaAGAT (SEQ ID_NO: 19) |
| >PRM_F4<br>AGGAUAAGTTA<br>TCTTAGGTTTA<br>TATGTTG<br>(SEQ<br>ID_NO: 20) | >F4<br>AAGAUAACTTATCCTCCAACATATAAACCAAAGCCAAGTTATCCGCCTTCATATAAGGCAA<br>AGAAATCATATCCTTCAACATATAAACCAAAGCCAAGTTATCCTCCAACATATAAAGCAAA<br>GAAAACTTATCCTTCAACATATAAACCAAAGCCAAGTTATCCTCCAACATATAAACCTAAG<br>ATAACTTaTCCT (SEQ ID_NO: 21) |
| >PRM_F5<br>AGGTUTATATG<br>TTGGAGGATAA<br>GTTTTC (SEQ<br>ID_NO: 22) | >F5<br>ATCCUCCAACATATAAACCAAAGCCAAGTTATCCGCCTTCATATAAGGCAAAGAAATCATA<br>TCCTTCAACATATAAACCAAAGCCAAGTTATCCTCCTACATATAAACCTAAGATAACTTAT<br>CCTCCAACATATAAACCAAAGCCAAGTTATCCTCCAACATATAAAGCAAAGAAAACTTATC<br>CTCCAACATATAaACCT (SEQ ID_NO: 23) |
| >PRM_F6<br>AGGATAACUTT<br>TCTTAGGTTTA<br>TAAGTTG<br>(SEQ<br>ID_NO: 24) | >F6<br>AACCUAAGATAACTTATCCTCCAACATATAAACCAAAGCCAAGTTATCCCACTTCATATAA<br>ATCTAAGAAAACTTATCCTCCAACATATAAACCTAAAATAACTTATCCACCAACATATAAA<br>CCAAAGCCAAGTTATCCACCATCATATAAACCTAAGATTACTTATCCTCCAACTTATAAAC<br>CTAAGAAAaGTTATCCT (SEQ ID_NO: 25) |
| >PRM_F7<br>ATATGUTGATG<br>GATAACTTGTT<br>TTACG (SEQ<br>ID_NO: 26) | >F7<br>AGTTATCCUCCAGCATACAAATCTAAGGCAAGTTATCCCCCTTCTTATCAACCCAAGAAAA<br>CTTATCTGCCATCATATAAACCTAAGAAAACTTATCCTCCAACATATAAACGTAAGATAAG<br>TTATCCACCAACGTATAAAACAAAGCCAAGTTATCCATCATCTTATAAACGTAAAACAAGT<br>TATCCATCAaCATAT (SEQ ID_NO: 27) |
| >PRM_F8<br>AGATUTATATG<br>AAGTGGGATAA<br>CTTGG (SEQ<br>ID_NO: 28) | >F8<br>ACATAUAAACGTAAGACTAGTTATCCTCCAACATATAAACCTAAGATAAGTTATCCTTCAA<br>CTTATAAAACAAAGCCAAGTTATCCACCAACGTATAAAGCAAAGAAAACTTATCCTCCAAC<br>ATATAAACCTAAGATAACTTATCCTCCAACATATAAACCAAAGCCAAGTTATCCCACTTCA<br>TATAaATCT (SEQ ID_NO: 29) |
| >PRM_F9<br>AGATAAGUTTT<br>CTTGGGTTGAT<br>AAGAAG (SEQ<br>ID_NO: 30) | >F9<br>AATCUAAGAAAACTTATCCTCCAACATATAAACCTAAAATAACTTATCCACCAACATATAA<br>ACCAAAGCCAAGTTATCCACCATCATATAAACCTAAGATTACTTATCCTCCAACTTATAAA<br>CCTAAGAAAAGTTATCCTCCAGCATACAAATCTAAGGCAAGTTATCCCCCTTCTTATCAAC<br>CCAAGAAAaCTTATCT (SEQ ID_NO: 31) |
| >PRM_F10<br>ATAAGTUGAAG<br>GATAACTTATC<br>TTAGG (SEQ<br>ID_NO: 32) | >F10<br>ACTTATCUGCCATCATATAAACCTAAGAAAACTTATCCTCCAACATATAAACGTAAGATAA<br>GTTATCCACCAACGTATAAAACAAAGCCAAGTTATCCAGCATCTTATAAACGTAAAACAAG<br>TTATCCATCAACATATAAACGTAAGACAAGTTATCCTCCAACATATAAACCTAAGATAAGT<br>TATCCTTCaACTTAT (SEQ ID_NO: 33) |
| >PRM_F11ATC<br>TTAGGUTTATA<br>TGATGATGCAT<br>AAC (SEQ<br>ID_NO: 34) | >F11<br>AACTTAUAAAACAAAGCCAAGTTATCCACCAACGTATAAACCAAAACCAAGTTATGCATCA<br>TCATATAAACCTAAGAT (SEQ ID_NO: 35) |

Step 2: SSP to DSP Conversion

Each of the SSPs are converted to DSPs using single primer extension. This process results in a DSP with either one or two USER-cleavable termini.

Step 3: DSP Assembly

Ordered directional assembly is achieved by generating complementary overhangs (via USER processing of the DSP). The length of these overhangs is tunable through the design of the SSP fragments. In this example they are set to 5-10 bases. The design of the SSPs also ensures that each junction is unique.

| Junction | Overlap |
|---|---|
| F1-F2 | ATCAT<br>TAGTA |
| F2-F3 | AGTTT<br>TCAAA |
| F3-F4 | AAGAT<br>TTCTA |

-continued

| Junction | Overlap |
|---|---|
| F4-F5 | ATCCT |
| | TAGGA |
| F5-F6 | AACCT |
| | TTGGA |
| F6-F7 | AGTTATCCT |
| | TCAATAGGA |
| F7-F8 | ACATAT |
| | TGTATA |
| F8-F9 | AATCT |
| | TTAGA |
| F9-F10 | ACTTATCT |
| | TGAATAGA |
| F10-F11 | AACTTAT |
| | TTGAATA |

The target sequence for this in-silico test was chosen because it would be difficult to synthesise using traditional DNA assembly techniques. This was confirmed when the DNA synthesis company, Integrated DNA Tecrhnologies, was asked to make the target sequence and reported multiple errors or complexities that would prevent them from synthesising the sequence. These multiple errors and complexities included: high density of repeated sequence; high lengths of repeated sequences; high numbers of repeats close to sequence termini; and a low GC content.

Example 4: Preparation of Antibody Libraries

Overview

In this experiment, libraries of linear DNA fragments were assembled using the methods of the invention. The library was prepared comparing unpurified and PAGE purified oligonucleotides, in order to determine the fidelity and representation of libraries produced with these different inputs. The quality of the libraries were determined with both Sanger and next generation sequencing (NGS). The library design contained 2 variable antibody complementarity determining regions which would eventually be directly transformed into yeast for display and screening (not part of this experiment).

In Silico DNA Design

Prior to wet lab assembly, an algorithm is used to determine the SSP design, including primer binding sites and the position and composition of the complementary overhangs (generated via USER enzyme) that facilitate assembly. The algorithmic process is outlined below:

1. User enters their target fragment sequence. In this example the target sequence is a sequence of 308 bases long, comprising degenerate sequences of 12 nucleotides (NNBNNBNNBNNB SEQ ID_NO:36) at positions 129 to 140 and 30 nucleotides (NNBNNBNNBNNBNNBNNBNNBNNBNNBNNB SEQ ID_NO:37) at positions 180 to 209

2. The user enters a number of predefined parameters that determine the SSP design including primer melting temperature (72° C.), minimum and maximum overhang length (4-12 bp), minimum and maximum SSP length (100-200 bp).

3. The algorithm optimises SSP design based on the desired parameters entered by the user, as well as a number of non-variable parameters some of which are listed below:

avoidance of palindromic sequences in overhang,
avoidance of semi-palindromic sequences in overhang,
avoidance of degenerate bases in overhang,
avoidance of triplet sequences "AAA", "TTT", "CCC", "GGG" in overhang,
avoidance of non-pairing overhangs with ≥4 contiguous or non-contiguous bases of homology, and
overhangs should be positioned to minimise SSP length.

Using these parameters, the algorithm converges on the best design.

4. In addition to these libraries, primers were also designed to include indexed Illumina NGS adapters to allow for direct NGS of the linear product, post-assembly. These adapters do not anneal directly to the SSPs but are filled in during the extension reaction. Adapter indexes were used to distinguish sequences prepared with PAGE purification and desalting in the final NGS data set. Index 6 was used for desalting SSPs, while index 12 was used for PAGE purified SSPs.

Wet Lab Assembly

Single Primer Extension

1. SSPs and their corresponding primers, as determined by the algorithm, were ordered through a commercial supplier.

2. SSPs and their corresponding primers were converted to DSPs in the extension reaction shown below. Phusion U polymerase was used to allow polymerase read through of deoxyuridines in the SSP templates. The negative control components follow the sample reaction.

Single Primer Extension Reactions:

| Component | Volume (μL) | Concentration |
|---|---|---|
| Phusion U Master Mix (2X) | 25 | 1X |
| 10 mM dNTPs | 1 | 0.2 mM |
| Reverse Primer (10 μM) | 2.5 | 0.5 μM |
| Template SSP (1 μg/μl) | 5 | 100 ng/uL |
| Milli-Q water (up to 50 μl) | 12.5 | — |

Negative Control Single Primer Extension Reactions:

| Component | Volume (μL) | Concentration |
|---|---|---|
| Phusion U Master Mix (2X) | 25 | 1X |
| Reverse Primer (10 μM) | 2.5 | 0.5 μM |
| Template SSP (1 μg/μl) | 5 | 100 ng/uL |
| Milli-Q water (up to 50 μl) | 12.5 | — |

3. The reactions were placed in a thermocycler and run with the following conditions:

| Step | Temperature (° C.) | Time |
|---|---|---|
| Denaturation | 98 | 40 secs |
| Primer annealing | 60 | 20 secs |
| Extension | 72 | 11 minutes |
| Store | 4 | Infinite |

4. DNA was purified using a silica-based column PCR purification kit, according to the manufacturer's instructions.

5. DNA was quantified using a Nanodrop spectrophotometer by measuring the absorbance at 260 nm. The results of this are shown below, with the first table showing the results of the extension reaction using standard extension primers and the second using extension primers which include overhanging NGS adapter sequences:

DSP Concentrations after Extension with Standard Primers:

| Sample | [Measured DSP] (ng/µL) | [Measured negative control] (ng/µL) | [Normalised DSP] (ng/µL) |
|---|---|---|---|
| DSP 1 (desalting) | 21.2 | 12.3 | 8.9 |
| DSP 2 (desalting) | 22.6 | 12.6 | 10 |
| DSP 1 (PAGE) | 32.2 | 19.8 | 12.4 |
| DSP 2 (PAGE) | 33.8 | 20.6 | 13.2 |

DNA concentrations were measured using a NanoDrop spectrophotometer.

DSP Concentrations after Extension with Primers Including Illumina NGS Adapter Sequences:

| Sample | [Measured DSP] (ng/µL) | [Measured negative control] (ng/µL) | [Normalised DSP] (ng/µL) |
|---|---|---|---|
| DSP 1 (desalting) | 29.6 | 27.3 | 2.3 |
| DSP 2 (desalting) | 39.2 | 30.5 | 8.7 |
| DSP 1 (PAGE) | 48.2 | 38.6 | 9.6 |
| DSP 2 (PAGE) | 56.6 | 42.8 | 13.8 |

DNA concentrations were measured using a NanoDrop spectrophotometer.

DNA Assembly

1. The two DSP parts were combined in a USER—ligation reaction as detailed in the table below, with the two DSPs added in equimolar amounts.

| Component | Amount |
|---|---|
| DSP 1 | 897 ng |
| DSP 2 | 1000 ng |
| CutSmart buffer (10X) | 12.5 µl |
| ATP (10 mM) | 12.5 µl |
| USER enzyme (1 U/µl) | 5 µl |
| T4 DNA Ligase (400 U/µl) | 5 µl |
| Milli-Q water | Up to 125 µl |

2. These reactions were incubated at 37° C. for 20 minutes to allow the USER excision of the deoxyuridine bases, followed by 21° C. overnight to allow overhang annealing and sealing of nicks by the T4 ligase.

3. Each reaction was run on a preparative 1% agarose gel, prestained with 1× SYBR safe nucleic acid dye at 90V for 1 hour. The image is shown below with the input DSPs present at around 150-200 bp and the fully assembled fragments shown at ~350 bp.

4. The correctly sized band was cut out with a scalpel and gel extracted with a standard silica column-based gel extraction kit according to the manufacturer's instructions.

5. This final products were quantified using a NanoDrop spectrophotometer by measuring the absorbance at 260 nm with the results shown below.

End-Point Clonal Sequencing

To allow Sanger sequencing of individual variants within the library, the assembled fragments needed to be cloned into an E. coli compatible plasmid, transformed into E. coli, and grown up on agar plates to allow single variants of the library to be picked, prepped and sequenced. The library fragment was inserted into the fluorophore of a constitutively expressed GFP cassette, interrupting its successful expression. This allowed for selection of successfully inserted fragments from background.

1. A standard pSB1C3 biobrick cloning vector containing a constitutively expressed GFP cassette was linearised using Phusion PCR, according to the standard PCR conditions detailed in the manufacturer's instructions (link).

2. Each reaction was run on a 1% agarose gel, prestained with 1× SYBR safe nucleic acid dye at 90V for 1 hour. The correctly sized band was excised with a scalpel and extracted using a standard silica-based column gel extraction kit, according the manufacturer's instructions.

3. The extracted DNA was quantified with a NanoDrop spectrophotometer.

4. The linearised vector DNA was combined in a blunt-end ligation reaction, with polynucleotide kinase also included to add 5' phosphates to facilitate ligation:

| Component | Amount |
|---|---|
| Linearised vector | 50 ng |
| Assembled library fragment | 15 ng |
| T4 Ligase buffer (10X) | 2 µl |
| T4 Polynucleotide Kinase (PNK) (10 U/µl) | 1 µl |
| T4 DNA Ligase (400 U/µl) | 1 µl |
| Milli-Q water | Up to 20 µl |

5. 5 µl of this reaction was mixed with 50 µl chemocompetent DH10B E. coli, transformed via heat-shock and plated on 34 µg/ml chloramphenicol LB agar plates and grown overnight at 37° C.

6. The following day, 20 single colonies from each of the desalting and PAGE purified assemblies were picked with a sterile pipette tip and were inoculated into 5 ml of sterile LB broth with 34 µg/ml chloramphenicol and grown overnight at 37° C., shaking at 225 RPM.

7. Plasmid preparation of these cultures was carried out using standard silica-based column kits, according to the manufacturer's instructions (Link)

8. The plasmid preps were then quantified with a Nano-Drop Spectrophotometer, their concentrations normalised to 75 ng/µl and 15 µl of each were aliquoted and sent for Sanger sequencing using a commercial supplier.

The results of this are summarised below. Reads were excluded from analysis if they were background vector or poor quality.

Fidelity of the two libraries, when analysed after subcloning into a standard vector, transforming into E. coli and Sanger sequencing of individual clones:

| Sample | N° reads included in analysis | Number in-frame (% in-frame) | Number in-design (% in-frame) | Mean number of deletions in incorrect variants |
|---|---|---|---|---|
| Desalting | 14 | 7 (50%) | 7 (50%) | 0.67 |
| PAGE purified | 17 | 12 (70.5%) | 10 (58.8%) | 1.67 |

There is no statistical significance between the fidelity of the desalting and PAGE purified library fragments (p>0.05, Pearson's chi-squared test). The sample size here is fairly low however, and a much richer data set would be found during the next generation sequencing.

Next Generation Sequencing Using the Illumina MiSeq System

Due to the addition of the Illumina TruSeq adapters to the DSPs during the single primer extension reaction, the resulting assembled library fragments did not require any library preparation prior to sequencing. The DNA was therefore sent directly to an commercial NGS service provider who performed the qPCR quantification, normalisation, and sequencing using the Illumina MiSeq system. Before any data analysis was performed on the sequencing data, all reads with low Phred scores were removed from the data set.

Base-by-Base Distribution Analysis

Firstly, the distribution of bases across the first "NNB" region of the fragment was analysed to assess how much, if any, bias is introduced into the library during synthesis and assembly. We also wanted to assess whether the purification method of the SSPs has any bearing on this biasing. The results are summarised in the bar charts on FIGS. 14a and 14b. These distributions are neither significantly different (p>0.05, Fisher's exact test) from the expected frequencies (N=25% for each base, B=33.3% for C, G, or T), nor from each other. This result suggests that little bias is introduced on a base-per-base basis during the library synthesis.

Analysis of Molecular Weight Biasing

Next the presence of any molecular weight biasing across the variable region was assessed. PAGE purification of synthesised oligonucleotides could result in biasing toward higher or lower molecular weights, depending on the area of band that is extracted. This was done by calculating the variable region molecular weight in each sequenced variant. We used this as a measurement since each base has its own molecular weight and, because The mean and spread of this data could then be compared with the what would be expected. A summary of this data is shown in the table below:

| Sample | Mean molecular weight variable region ± standard error | Standard deviation |
| --- | --- | --- |
| PAGE purified | 5252.015 ± 0.07 | 49.96 |
| Desalting | 5245.66 ± 0.11 | 51.35 |
| Expected | 5265.60 ± 0.12 | 52.64 |

There is a significant statistical difference (p<0.01, two sample paired T-test) between the recorded data and the expected molecular weight of the variable region. This statistical difference is unsurprising given the sensitivity of the T-test to large data-sets; the actual differences between the means (<20 Da) and standard deviations (<3 Da) are very small, meaning that the biasing of these libraries would be unlikely to have any material effect on an eventual screen.

Fidelity Analysis

Finally, the fidelity of the library was analysed. Firstly, the DNA sequences were checked directly against the template sequence to check for "in-design" variants—i.e. sequences that perfectly matched the template design. Next, each DNA sequence was translated to protein sequence and checked against the protein template sequence—this yields both the protein in-design rate, and the in-frame rate. Finally, because the degenerate 'NNB' codon correctly translates to stop codons, in order to evaluate how many frameshift mutations were down to synthesis error rather than correctly occurring stop codons, the variable region was excluded from the analysis. The results of this analysis are summarised in the table below.

| Parameter | PAGE Purified | Desalting |
| --- | --- | --- |
| DNA sequences in-design (%) | 69.66 | 71.12 |
| Protein sequences in-design (%) | 71.71 | 73.2 |
| Protein sequences in-frame (%) | 69.69 | 71.38 |
| Protein sequences in-frame, excluding variable region (%) | 75.71 | 76.9 |

The differences between the fidelity of the PAGE purified and desalting libraries are not statistically significant (p>0.05, Pearson's Chi-squared test). This is interesting, given that PAGE purification ought to remove a great deal of truncations and deletions that occur during oligonucleotide synthesis. However, it is possible that because there is such a large amount of variability in molecular weight in this degenerate SSP, that the full length band on the PAGE gel would appear indistinct. If purification were carried out on this entire band, most common synthesis errors (1-2 bp deletions) would be carried through the purification process and appear in the final library.

This example shows that high quality libraries of sequences with randomized degenerate portions can be obtained using the methods of the invention.

Example 5: Use of Self-Priming SSPs

Figure 2:
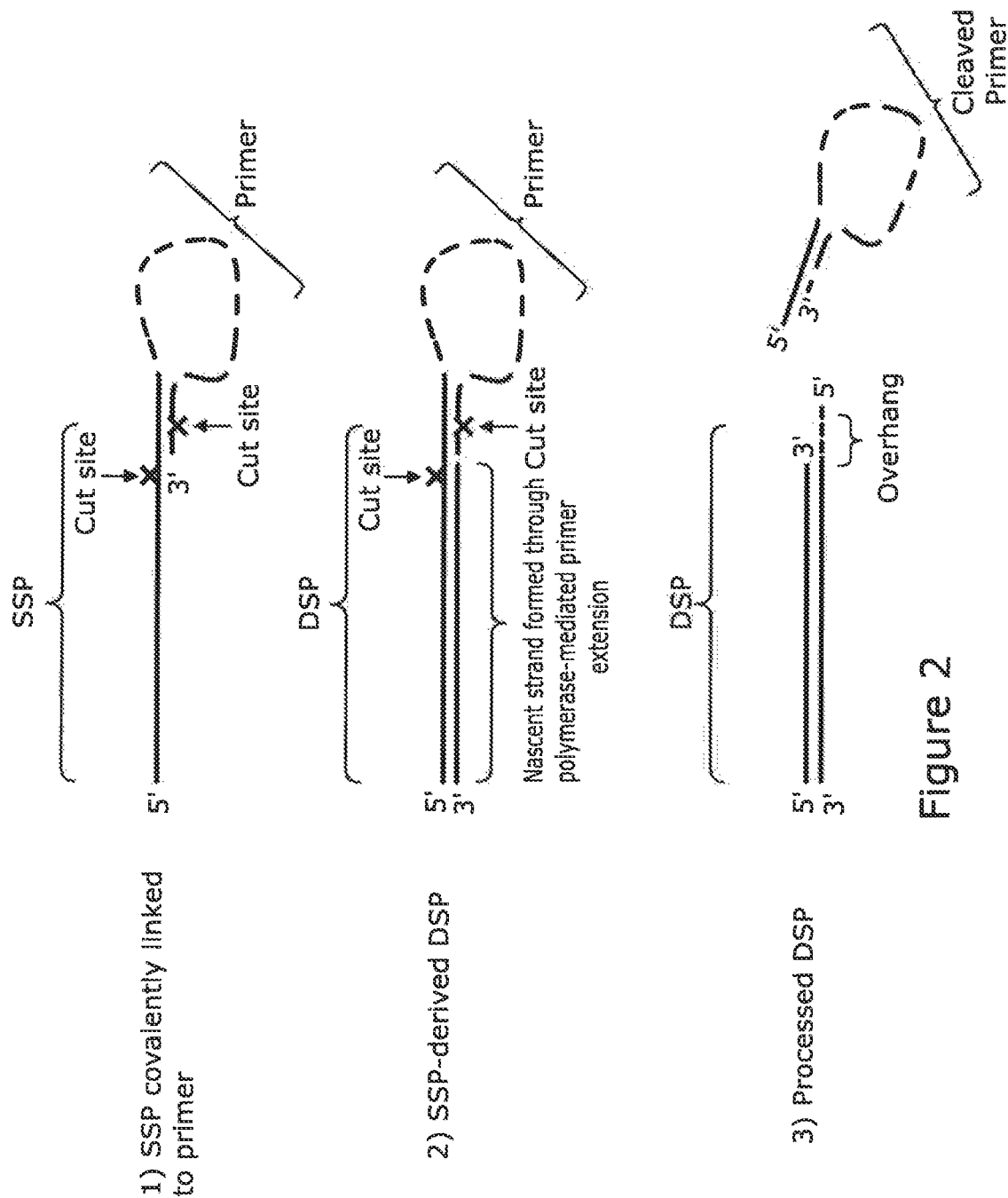
FIG. 2 shows an embodiment in which an SSP is covalently linked to a polynucleotide sequence comprising a primer.

This example demonstrates the use of a self-priming SSP (i.e. an SSP that is covalently linked to a polynucleotide sequence comprising a primer, as explained in relation to FIG. 2) to allow the conversion of an SSP to a DSP without the use of a separate primer sequence. The self-priming sequence contained cleavable bases, allowing the generation of overhangs for directional DNA assembly and the removal of the majority of the priming region. In this way, when assembling variable SSPs, the proportion of DNA sequence required to be constant can be reduced to just the length of the overhang (~6 bp) rather than the length of the primer binding sequence (18-25 bp). This allows the user more freedom over the positioning of degenerate bases within their DNA library. In addition, because the primer sequence is included within the SSP, there would be less chance of mis-annealing of the priming to other regions of the SSP. This could therefore increase the fidelity of the primer extension reaction, improving the overall fidelity of the final DNA library.

To permit SSP self-priming, a stem-loop structure is required within the SSP sequence to allow the SSP to fold back on itself and allow the self-priming region to anneal to its complementary sequence. In addition, deoxyuridines were positioned on both strands of the self-priming regions and one at the 5' end of the SSP, such that, after polymerase extension, USER enzymes would remove the primer region, the stem-loop and leave an overhang at both ends of the DSP to permit assembly (see FIG. 2 for an overview of this process, where only one overhang is created; a deoxyuridine—labelled as "cut site" on FIG. 2—may also be included towards the 5' terminus of the SSP, in order to generate an overhang at both termini).

DNA Design

Prior to wet-lab assembly, the SSPs and PCR primers for vector linearisation had to be designed. The most important aspect of this design is ensuring the stem-loop structure remains stable at the extension temperature of the polymerase. Stable loop structures have been previously identified, with tetraloop structures identified as being some of the most stable. As such, a GTTA sequence was incorporated into the SSP to facilitate stem binding. The stem sequence itself was designed to have a high Tm, such that it was stable during polymerase extension:

```
5' ACTCACG 3'
3' TGAGTGC 5'
```

The remainder of the sequence was designed such that it could be inserted into a target vector. The SSP included a constitutive promoter (J23101), while the vector linearisation PCR eliminated the promoter from a construct that normally would constitutively express GFP. This would quickly allow identification of clones containing the inserted DSP. The full SSP sequence is shown below.

```
SSP design (SEQ ID_NO: 38):
5' CAGCAUTTGACGGCTAGCTCAGTCCTAGGTACAGTGCTAGCTAATAC
GACTCACTATAGGGAGATACTAGAGACCGTCGAGTA
CCTTTACAGCTAGCTCAGTCCTAGGTATTATGCTAGCUACTCACGTTAGT
GAGTAGCTAGCAUAATACC 3'

Forward vector linearisation primer (SEQ ID_NO:
39):
5' ATGCTAGCUGAGAAATCAAATTAAGGAGGTAAG 3'

Reverse vector linearisation primer (SEQ ID_NO:
40):
5' ATGCTGUCCAGAAATCATCCTTAGCG 3'
```

Wet Lab Validation
SSP to DSP Conversion

Before attempting to clone the DSP into a vector, the conversion of the SSP to DSP without an external primer was validated.

1. SSPs were ordered through a commercial supplier.
2. The reactions were set up as in the table below:

| Component | Volume (µL) |
| --- | --- |
| Phusion U Master Mix | 25 |
| ULT8 (1 µg/µl) | 1 |
| Milli-Q water (up to 50 µl) | 24 |

The negative controls were set up as in the table below:

| Component | Volume (µL) |
| --- | --- |
| 5x Phusion HF/GC Buffer | 10 |
| 10 mM dNTPs | 1 |
| ULT8 (1 µg/µl) | 1 |
| Milli-Q water (up to 50 µl) | 38 |

The reactions were run in the thermocycler with the following conditions:

| Step | Temperature (° C.) | Time |
| --- | --- | --- |
| Denaturation | 98 | 40 secs |
| Annealing | Gradient of 62.4-72 | 20 secs |
| Extension | 72 | 11 minutes |
| Store | 4 | Infinite |

3. Ran 10 µl of each reaction on an agarose gel to check size.
4. Purify the remainder of the reactions immediately using a silica-based column PCR purification kit according to the manufacturer's instructions.
5. Quantify using a Nanodrop spectrophotometer. Normalised DNA concentrations and yields after polymerase extension reaction are shown below. These values were normalised against a negative control, containing no DNA polymerase.

| Sample | Annealing temp (° C.) | Normalised Concentration (ng/µl) | Total Yield (ng) | Efficiency (%) |
| --- | --- | --- | --- | --- |
| A | 60 | 15.1 | 755 | 37.8 |
| B | 60.8 | 16.0 | 800 | 40 |
| C | 62.4 | 15.4 | 770 | 38.5 |
| D | 64.7 | 14.9 | 745 | 37.3 |
| E | 67.6 | 14.1 | 705 | 35.3 |
| F | 70 | 15.6 | 780 | 39.0 |
| G | 71.4 | 15.6 | 760 | 38.0 |
| H | 72 | 15.7 | 785 | 39.3 |

These results suggest the SSPs are successfully being converted double-stranded DNA by the DNA polymerase, via self-priming. However it is difficult to tell from this data whether the stem-loop has formed as expected or whether misannealing has occurred which result in an incorrect assembly. To do this, the DSPs would be cloned into a vector and sequence verified.

Cleaving Off Stem-Loop Sequence from DSPs and Cloning into Vector

1. A plasmid containing a constitutively expressed GFP cassette was linearised using PCR with primers containing deoxyuridine bases to facilitate overhang generation
2. The resulting PCR product was treated with DpnI restriction enzyme to remove any background vector.
3. This mixture was then run on an agarose gel and correctly sized product was gel extracted.
4. This purified PCR product was then mixed with the DSP with the highest annealing temperature prepared in the previous experiment. Two negative controls were also included, both lacking the DSP, one also lacking the USER enzyme and replacing it with a T4 ligase. The reactions were set up with the following reagents and reaction conditions:

| Component | Amount |
| --- | --- |
| DSP | 200 ng |
| Linearised vector | 150 ng |
| CutSmart buffer (10x) | 2.5 µl |
| USER enzymes (1 U/µl) | 1 µl |
| Milli-Q water | Up to 25 µl |

The reaction set up for negative control 1 lacking the DSP insert and replacing the USER enzyme with T4 ligase was as follows:

| Component | Amount |
| --- | --- |
| DSP | 0 ng |
| Linearised vector | 150 ng |
| CutSmart buffer (10x) | 2.5 µl |
| T4 ligase | 1 µl |
| 10 mM ATP | 2.5 µl |
| Milli-Q water | Up to 25 µl |

The reaction set up for negative control 2 lacking the DSP insert was as follows:

| Component | Amount |
| --- | --- |
| DSP | 0 ng |
| Linearised vector | 150 ng |
| CutSmart buffer (10x) | 2.5 µl |
| USER enzymes (1 U/µl) | 1 µl |
| Milli-Q water | Up to 25 µl |

The reaction conditions for USER-mediated assembly of DSPs and linearised vector was as follows:

| Step | Temperature (C.) | Time |
| --- | --- | --- |
| USER cleavage | 37 | 20 minutes |
| Overhang annealing | 21 | 20 minutes |
| Store | 4 | Infinite |

5. 5 µl of this reaction was transformed into chemocompetent *E. coli* via 42° C. heat-shock and plated on LB agar with 34 µg/ml chloramphenicol after 1 hour outgrowth at 37° C.

6. The plates were imaged under a blue light to check for the presence of fluorescent colonies. The results (not shown) indicated that the addition of the DSP restores fluorescence. Colonies arising from the ligation reaction without DSP insert were non-fluorescent since their promoter has been removed, while very few (non-fluorescent) colonies grew on the plate without the DSP insert with USER enzymes.

Therefore, the results showed that colonies transformed with the sample assembly mixture were fluorescent, indicating that the DSPs have been correctly cloned into the vector, restoring the promoter and allowing GFP expression. To verify this, 5 colonies from the sample plate were picked, grown up overnight in 5 ml of sterile LB media with 34 µg/ml chloramphenicol. These cultures were then plasmid prepped with a silica-based column system, according to the manufacturer's instructions and sent for sequencing with a commercial supplier.

3/5 constructs were correctly inserted, while 1 clone contained a 13 bp deletion and another contained a 14 bp deletion. These deletions were likely to be caused by misannealing of the self-priming region. After extension and cleavage with the USER enzymes, the deoxyuridines were not positioned correctly in the sequence, meaning that additional sequence was lost.

CONCLUSIONS

This example demonstrates a proof-of-principle experiment in using self-priming SSPs to facilitate SSP-DSP conversion, and subsequent removal of the stem-loop structure, to allow scarless assembly into a vector. The design of the stem-loop sequence could be improved to ensure that it forms correctly and that no sequence is lost. To do this, the experiment could be repeated with a number of different stem-loop sequence designs. In addition, a more stringent reporter would be chosen, such that any errors in the sequence would prevent correct expression. For example, the insert could be positioned within a fluorescent protein, rather than being its promoter. Any INDELs in the DSP would knock-out correct expression of the fluorescent protein. In doing this, analysis of the fidelity would simply entail calculating the ratio of fluorescent to non-fluorescent colonies.

Alternative expressions of the inventive concept may be found in the following numbered clauses:

1. A method of assembling a target double stranded polynucleotide (DSP) comprising a first DSP and a second DSP, the method comprising
   (i) providing a single stranded polynucleotide (SSP) comprising a primer annealing site at one or both termini, wherein the SSP comprises a portion of the polynucleotide sequence of one strand of the first DSP;
   (ii) annealing a primer to the SSP and converting the SSP to the first DSP through the polymerase-mediated extension of the primer, wherein the first DSP comprises a polynucleotide sequence that is complementary to a polynucleotide sequence of a second DSP, and
   (iii) assembling the target polynucleotide sequence by joining the first DSP to the second DSP via their complementary polynucleotide sequences.

2. The method of clause 1, wherein the target polynucleotide sequence is assembled from a population of DSPs and wherein
   step (i) comprises providing a population of single stranded polynucleotides (SSPs), each comprising a primer annealing site at one or both termini, wherein each SSP comprises a portion of the polynucleotide sequence of one strand of a DSP in the population,
   step (ii) comprises annealing a primer to SSPs in the population and converting the SSPs to a population of DSPs through the polymerase-mediated extension of the primers, wherein some or all DSPs in the population comprise a polynucleotide sequence that is complementary to (a) a polynucleotide sequence of another DSP in the population, or (b) a polynucleotide sequence of a DSP that is not part of the population, and
   step (iii) comprises assembling the target polynucleotide sequence by joining either some or all of the DSPs in the population to at least one other DSP of the population and/or to at least one DSP that is not a DSP of the population.

3. The method of clause 2, wherein the population of DSPs consists of n DSPs and n−2 DSPs are joined to two other DSPs of the population and the two DSPs which are not joined to two other DSPs in the population are each joined to one other DSP in the population and optionally to another DSP that is not from the population.

4. The method of clause 2, wherein each DSP of the population is joined to a DSP that is not a DSP of the population and is optionally not directly joined to any other DSP of the population.

5. The method of any preceding clause, wherein the DSP or some or all of the population of DSPs generated in step (ii) comprise(s) a region of single stranded polynucleotide forming a 3' or 5' overhang which comprises the complementary polynucleotide sequence.

6, The method of clause 5, wherein the overhang is generated by USER (Uracil-Specific Excision Reagent) enzyme mix, a Type IIS restriction enzyme, or an exonuclease.

7. The method of clause 5, wherein the overhang is generated by using a modified polymerase extension reaction.

8. The method of any of clauses 5-7, wherein in step (iii) the DSPs are joined together by annealing of complementary overhangs.

9. The method of clause 8, wherein the ordering and directionality of each DSP is determined by unique overhang pairs.

10. The method of clause 8 or clause 9, further comprising ligating the DSPs using a ligase enzyme.

11. The method of clause 10, wherein the ligase is T3 DNA ligase, T4 DNA ligase, T7 DNA ligase, *E. coli* DNA ligase, Taq ligase, 9N DNA ligase, any variant thereof, or any combination thereof.

12. The method any of clauses 5-11, wherein the overhangs are at least 1, 2, 3, 4, 5, 6, 7, 8, 9, 10, 11 or 12 bases long.

13. The method of any one of clauses 1-4, wherein the DSP or at least one of the population of DSPs generated in step (ii) is in a fully double stranded state and do not comprise 5' or 3' overhangs.

14. The method of clause 13, wherein in step (iii) the DSPs are joined together by homologous recombination.

15. The method of any preceding clause, wherein multiple identical target polynucleotide sequences are assembled simultaneously, and/or wherein multiple different target polynucleotide sequences are assembled simultaneously.

16. The method of clause 15, wherein the multiple different target polynucleotide sequences can singularly be mapped back to one or more degenerate polynucleotide designs.

17. The method of any of clause 2-16, wherein the SSPs are spatially separated during step (ii).

18. The method of clause 17, wherein spatial separation is facilitated via immobilisation of the SSPs to a solid support.

19. The method of any preceding clause, wherein the SSP or each SSP comprises at least 70%, at least 80%, at least 90% or at least 95% of the polynucleotide sequence of one strand of the DSP into which that SSP is converted in step (ii).

20. The method of any preceding clause, wherein one strand of a DSP formed from an SSP in step (ii) comprises the SSP and the reverse complement of any 5' region of the SSP's corresponding primer that does not anneal to the SSP.

21. The method of any preceding clause, wherein the SSP or each SSP comprises a single primer annealing site and wherein the first DSP or a plurality of DSPs in the population is/are produced by a single primer extension reaction.

22. The method of any preceding clause, wherein in step (i), the SSP is covalently linked to a polynucleotide sequence comprising the primer which anneals to that SSP in step (ii), or, where a population of SSPs is used, one or more SSPs in the population is each covalently linked to a polynucleotide sequence comprising the primer which anneals to that SSP in step (ii)

23. The method of any preceding clause, wherein no DSPs are generated using an amplification method.

24. The method of any preceding clause, wherein each SSP is at least 30, 40, 50, 100, 200, 300, 400, 500, 600, 700, 800, 900 or 1,000 bases long.

25. The method of any preceding clause, further comprising subjecting the DSPs to one or more error removal steps.

26. The method of clauses 25, where the error removal step comprises cleavage of a DSP by a mismatch binding agent.

27. The method of any one of clauses 2-26, wherein a plurality of SSPs each comprise one universal primer binding site at a given terminus, and wherein a universal primer complementary to said universal primer binding site is used to convert the SSPs into DSPs in a polymerase based reaction.

28. The method of any preceding clause, further comprising purifying DSPs to remove undesirable reaction components.

29. The method of any preceding clause, wherein the assembly of two or more DSPs is by hierarchical assembly.

30. The method of any preceding clause further comprising transforming the target polynucleotide sequence into a host cell.

31. The method of any preceding clause, wherein after step (iii), the target polynucleotide sequence is amplified.

32. The method of any preceding clause, further comprising subjecting the target polynucleotide sequence to sequence verification.

33. A method for the preparation of a library of target polynucleotide sequences, the method comprising simultaneously producing a plurality of different target polynucleotide sequences using the method of any preceding clause.

34. A double stranded polynucleotide library produced according to the method of clause 33.

Unless otherwise indicated, the practice of the present invention employs conventional techniques of chemistry, molecular biology, microbiology, recombinant DNA technology, and chemical methods, which are within the capabilities of a person of ordinary skill in the art. Such techniques are also explained in the literature, for example, M. R. Green, J. Sambrook, 2012, Molecular Cloning: A Laboratory Manual, Fourth Edition, Books 1-3, Cold Spring Harbor Laboratory Press, Cold Spring Harbor, N.Y.; Ausubel, F. M. et al. (1995 and periodic supplements; Current Protocols in Molecular Biology, ch. 9, 13, and 16, John Wiley & Sons, New York, N.Y.); B. Roe, J. Crabtree, and A. Kahn, 1996, DNA Isolation and Sequencing: Essential Techniques, John Wiley & Sons; J. M. Polak and James O'D. McGee, 1990, In Situ Hybridisation: Principles and Practice, Oxford University Press; M. J. Gait (Editor), 1984, Oligonucleotide Synthesis: A Practical Approach, IRL Press; and D. M. J. Lilley and J. E. Dahlberg, 1992, Methods of Enzymology: DNA Structure Part A: Synthesis and Physical Analysis of DNA Methods in Enzymology, Academic Press. Each of these general texts is herein incorporated by reference.

Although particular embodiments of the invention have been disclosed herein in detail, this has been done by way of example and for the purposes of illustration only. The aforementioned embodiments are not intended to be limiting with respect to the scope of the appended claims, which follow. It is contemplated by the inventors that various substitutions, alterations, and modifications may be made to the invention without departing from the spirit and scope of the invention as defined by the claims.

The invention claimed is:

1. An in vitro method of assembling a target polynucleotide sequence comprising at least a first double stranded polynucleotide (DSP) and a second DSP, the method comprising an assembly reaction comprising the steps of:
   (i) providing a first single stranded polynucleotide (SSP) comprising the polynucleotide sequence of one strand of the first DSP, and a second SSP comprising the polynucleotide sequence of one strand of the second DSP,
   (ii) providing a first primer that binds at a terminus of the first SSP and a second primer that binds at a terminus of the second SSP and converting the first SSP to the first DSP and the second SSP to the second DSP through a single polymerase-mediated extension of the first and second primers, wherein the first DSP comprises a polynucleotide sequence that is complementary to a polynucleotide sequence of the second DSP,
   (iii) generating a region of single stranded polynucleotide on each of the first and second DSPs by forming a 3' or 5' overhang which comprises at least a portion of the complementary polynucleotide sequence; and
   (iv) assembling the target polynucleotide sequence by joining the first DSP to the second DSP via annealing of the complementary overhangs, wherein the ordering and directionality of each of the first and second DSPs is determined by unique overhang pairing.

2. The method of claim 1, wherein steps (i) to (iii) occur in separate reaction vessels and step (iv) occurs in a single reaction vessel.

3. The method of claim 1, wherein each complementary polynucleotide sequence is different and only permits annealing to one other complementary sequence within the assembly reaction.

4. The method of claim 3, wherein each complementary polynucleotide sequence forms a unique binding pair with one other complementary polynucleotide sequence within the assembly reaction, and wherein the total number of unique binding pairs within the assembly reaction is one less than the total number of DSPs in the assembly reaction.

5. The method of claim 1, wherein at least one primer comprises at least one uridine nucleotide and at least one SSP comprises at least one uridine nucleotide within the complementary polynucleotide sequence.

6. The method of claim 5, wherein the step (iii) of generating a region of single stranded polynucleotide occurs by exposing the DSPs to a mixture of Uracil DNA glycosylase (UDG) and a DNA glycosylase-lyase Endonuclease VIII, with these enzymes mediating deoxyuridine excision and backbone cleavage reaction.

7. The method of claim 1, wherein the step (iv) joining of the DSPs via annealing of the complementary overhangs comprises a ligation reaction.

8. The method of claim 1, wherein the complementary polynucleotide sequence is not more than 15 bases in length and not less than 4 bases in length.

9. The method of claim 1, wherein the complementary polynucleotide sequence is not more than 12 bases in length and not less than 4 bases in length.

10. The method of claim 1, wherein generating overhangs further comprises generating overhangs at the terminus of the first and last DSP that do not anneal to another DSP, such that the assembled target polynucleotide sequence comprises overhangs at both termini.

11. The method of claim 10, wherein the assembled target polynucleotide sequence has overhangs comprising sequences that are complementary to sequences in overhangs of a linearised vector wherein the linearised vector is created by polymerase-mediated extension of the circular vector using primers containing at least one uridine nucleotide, followed by digestion into a linear vector and Uracil-Specific Excision Reagent (USER) mediated uridine excision and backbone cleavage reaction to generate the overhangs.

12. The method of claim 1, wherein the first double stranded polynucleotide (DSP) is first flanking double stranded polynucleotide (DSP), the second DSP is an intervening DSP of a set of at least one intervening DSPs, and the method further comprises a second flanking DSP, the method comprising an assembly reaction comprising the steps of:
   (i) providing a first flanking single stranded polynucleotide (SSP) comprising the polynucleotide sequence of one strand of the first flanking DSP, a second flanking SSP comprising the polynucleotide sequence of one strand of the second flanking DSP, and at least a further SSP comprising the polynucleotide sequence of one strand of the at least one intervening DSP;
   (ii) providing a first primer that binds at a terminus of the first flanking SSP, a second primer that binds at a terminus of the second flanking SSP and a third primer that binds at a terminus of the intervening DSP, and converting the first flanking SSP to the first flanking DSP, the second flanking SSP to the second flanking DSP and the intervening SSP to the intervening DSP through a single polymerase-mediated extension of the first, second, and third primers,
   wherein the first flanking DSP comprises a first complementary polynucleotide sequence (CPS1) that is complementary to a polynucleotide sequence of the intervening DSP, the intervening DSP comprises a second complementary polynucleotide sequence (CPS2) that is complementary to CPS1 of the first flanking DSP as well as a third complementary polynucleotide sequence (CPS3) that is complementary to a polynucleotide sequence of the second flanking DSP, and the second flanking DSP comprises a fourth complementary polynucleotide sequence (CPS4) that is complementary to CPS3 of the intervening DSP;
   (iii) generating a region of single stranded polynucleotide on each of the DSPs by forming a 3' or 5' overhang which comprises at least a portion of the first to fourth complementary polynucleotide sequences (CPS1-4); and
   (iv) assembling the target polynucleotide sequence by joining the first flanking DSP to the intervening DSP, and the intervening to the second flanking DSP via annealing of the complementary overhangs, wherein the ordering and directionality of each of the first flanking, intervening and second flanking DSPs is determined by unique overhang pairing within the first to fourth complementary polynucleotide sequences (CPS1-4).

13. The method of claim 12, wherein the method comprises a plurality of intervening DSPs, wherein the ordering and directionality of each of the plurality of intervening DSPs both relative to each other and relative to the first flanking and second flanking DSPs is determined by unique overhang pairing within the respective complementary polynucleotide sequences.

14. The method of claim 12, wherein each complementary polynucleotide sequence is different and only permits annealing to one other complementary sequence within the assembly reaction, wherein each complementary polynucleotide sequence forms a unique binding pair with one other complementary polynucleotide sequence within the assembly reaction, and wherein the total number of unique binding pairs within the assembly reaction is one less than the total number of DSPs in the assembly reaction.

15. The method of claim 12, wherein the first primer that binds at a terminus of the first flanking SSP, and the primer(s) that bind(s) at a terminus of the at least one intervening SSP comprise at least one deoxyuridine nucleotide.

16. The method of claim 12, wherein the at least one intervening SSP and the second flanking SSP comprise at least one deoxyuridine nucleotide, and wherein the deoxyuridine nucleotide is comprised within the complementary polynucleotide sequence.

17. The method of claim 15, wherein the step (iii) of generating a region of single stranded polynucleotide occurs by exposing the DSPs to a Uracil-Specific Excision Reagent (USER) mediated deoxyuridine excision and backbone cleavage reaction.

18. The method of claim 12, wherein the first DSP comprises at least one sequence selected from the group consisting of: a vector sequence; a DNA sequence encoding an antibiotic resistance marker; a DNA sequence encoding a fluorescent protein; a DNA sequence encoding a regulatory protein; a DNA sequence encoding an antibody framework; and a DNA sequence encoding a protein used for the display of binding proteins or peptides.

19. The method of claim 1, wherein at least one of the DSPs comprised within the assembly reaction comprises a degenerate polynucleotide sequence.

20. The method of claim 1, wherein one or more SSPs are covalently linked to a polynucleotide sequence comprising the primer binding at a terminus of the SSP.

* * * * *